United States Patent
Phares et al.

(10) Patent No.: US 11,826,328 B2
(45) Date of Patent: Nov. 28, 2023

(54) STABLE TREPROSTINIL PRODRUGS

(71) Applicant: United Therapeutics Corporation, Silver Spring, MD (US)

(72) Inventors: Kenneth Robert Phares, Hillsborough, NC (US); Hitesh Batra, Herndon, VA (US); Liang Guo, Vienna, VA (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

(21) Appl. No.: 17/549,573

(22) Filed: Dec. 13, 2021

(65) Prior Publication Data

US 2022/0323387 A1    Oct. 13, 2022

Related U.S. Application Data

(60) Provisional application No. 63/125,145, filed on Dec. 14, 2020.

(51) Int. Cl.
*A61K 31/192* (2006.01)
*A61K 9/00* (2006.01)
*A61K 9/08* (2006.01)
*A61K 31/222* (2006.01)
*A61K 31/6615* (2006.01)

(52) U.S. Cl.
CPC .......... *A61K 31/192* (2013.01); *A61K 9/0053* (2013.01); *A61K 9/08* (2013.01); *A61K 31/222* (2013.01); *A61K 31/6615* (2013.01)

(58) Field of Classification Search
CPC .................................................... A61K 31/192
See application file for complete search history.

(56) References Cited

U.S. PATENT DOCUMENTS

| | | | |
|---|---|---|---|
| 4,306,075 A | 12/1981 | Aristoff | |
| 5,153,222 A | 10/1992 | Tadepalli et al. | |
| 5,234,953 A | 8/1993 | Crow et al. | |
| 6,054,486 A | 4/2000 | Crow et al. | |
| 6,441,245 B1 | 8/2002 | Moriarty et al. | |
| 6,521,212 B1 | 2/2003 | Cloutier et al. | |
| 6,528,688 B2 | 3/2003 | Moriarty et al. | |
| 6,700,025 B2 | 3/2004 | Moriarty et al. | |
| 6,756,033 B2 | 6/2004 | Cloutier et al. | |
| 6,756,117 B1 | 6/2004 | Barnes | |
| 6,803,386 B2 | 10/2004 | Shorr et al. | |
| 6,809,223 B2 | 10/2004 | Moriarty et al. | |
| 7,199,157 B2 | 4/2007 | Wade et al. | |
| 7,384,978 B2 | 6/2008 | Phares et al. | |
| 7,417,070 B2 | 8/2008 | Phares et al. | |
| 7,544,713 B2 | 6/2009 | Phares et al. | |
| 7,879,909 B2 | 2/2011 | Wade et al. | |
| 7,999,007 B2 | 8/2011 | Jeffs et al. | |
| 8,232,316 B2 | 7/2012 | Phares et al. | |
| 8,242,305 B2 | 8/2012 | Batra et al. | |
| 8,252,839 B2 | 8/2012 | Phares et al. | |
| 8,349,892 B2 | 1/2013 | Phares | |
| 8,350,079 B2 | 1/2013 | Walsh | |
| 8,410,169 B2 | 4/2013 | Phares et al. | |
| 8,461,393 B2 | 6/2013 | Sharma | |
| 8,481,782 B2 | 7/2013 | Batra et al. | |
| 8,497,393 B2 | 7/2013 | Batra et al. | |
| 8,536,363 B2 | 9/2013 | Phares et al. | |
| 8,563,614 B2 | 10/2013 | Wade et al. | |
| 8,609,728 B2 | 12/2013 | Rothblatt et al. | |
| 8,653,137 B2 | 2/2014 | Jeffs et al. | |
| 8,658,694 B2 | 2/2014 | Jeffs et al. | |
| 8,747,897 B2 | 6/2014 | Kidane et al. | |
| 8,765,813 B2 | 7/2014 | Wade et al. | |
| 8,940,930 B2 | 1/2015 | Batra et al. | |
| 9,029,607 B2 | 5/2015 | Mcgowan et al. | |
| 9,050,311 B2 | 6/2015 | Phares et al. | |
| 9,156,786 B2 | 10/2015 | Batra et al. | |
| 9,199,908 B2 | 12/2015 | Phares et al. | |
| 9,255,064 B2 | 2/2016 | Malinin et al. | |
| 9,278,901 B2 | 3/2016 | Phares et al. | |
| 9,278,902 B2 | 3/2016 | Tang et al. | |
| 9,278,903 B2 | 3/2016 | Tang et al. | |
| 9,339,507 B2 | 5/2016 | Olschewski et al. | |
| 9,346,738 B2 | 5/2016 | Jain et al. | |
| 9,358,240 B2 | 6/2016 | Olschewski et al. | |
| 9,371,264 B2 | 6/2016 | Becker et al. | |
| 9,388,154 B2 | 7/2016 | Yiannikouros et al. | |
| 9,394,227 B1 | 7/2016 | Zhang et al. | |
| 9,422,223 B2 | 8/2016 | Phares et al. | |
| 9,505,737 B2 | 11/2016 | Becker et al. | |
| 9,624,156 B2 | 4/2017 | Phares et al. | |
| 9,643,911 B2 | 5/2017 | Zhang et al. | |
| 9,758,465 B2 | 9/2017 | Laing | |
| 9,878,972 B2 * | 1/2018 | Phares | A61P 9/10 |
| 9,957,220 B2 | 5/2018 | Zhang et al. | |
| 10,464,877 B2 | 11/2019 | Zhang et al. | |
| 10,703,706 B2 | 7/2020 | Zhang et al. | |
| 10,947,177 B2 * | 3/2021 | Phares | A61P 9/12 |
| 11,292,758 B2 * | 4/2022 | Phares | A61K 31/192 |
| 2008/0200449 A1 | 8/2008 | Olschewski et al. | |
| 2008/0280986 A1 | 11/2008 | Wade et al. | |
| 2009/0036465 A1 | 2/2009 | Roscigno et al. | |
| 2009/0124697 A1 | 5/2009 | Cloutier et al. | |
| 2012/0010159 A1 * | 1/2012 | Rothblatt | A61P 29/00 514/567 |
| 2012/0197041 A1 | 8/2012 | Batra et al. | |
| 2013/0184295 A1 | 7/2013 | Sprague et al. | |
| 2013/0331593 A1 | 12/2013 | McGowan et al. | |

(Continued)

FOREIGN PATENT DOCUMENTS

WO    WO-00/57701 A1    10/2000
WO    WO-2005/007081 A2    1/2005

(Continued)

OTHER PUBLICATIONS

Moriarty et al., "The Intramolecular Asymmetric Pauson-Khand Cyclization as a Novel and General Stereoselective Route to Benzindene Prostacyclins: Synthesis of UT-15 (Treprostinil)," J. Org. Chem. 2004, 69, 1890-1902.

(Continued)

*Primary Examiner* — Rei Tsang Shiao
(74) *Attorney, Agent, or Firm* — Foley & Lardner LLP

(57) ABSTRACT

Provided are novel prodrugs of treprostinil, as well as methods of making and methods of using these prodrugs.

10 Claims, 30 Drawing Sheets

(56) References Cited

U.S. PATENT DOCUMENTS

| | | |
|---|---|---|
| 2014/0024856 A1 | 1/2014 | Giust et al. |
| 2014/0275262 A1 | 9/2014 | Phares et al. |
| 2014/0275616 A1 | 9/2014 | Batra et al. |
| 2014/0323567 A1 | 10/2014 | Laing |
| 2015/0148414 A1 | 5/2015 | Malinin et al. |
| 2015/0166503 A1* | 6/2015 | Becker .............. C07D 263/24 549/267 |
| 2015/0299091 A1 | 10/2015 | Batra et al. |
| 2015/0315114 A1 | 11/2015 | Hering et al. |
| 2015/0328232 A1 | 11/2015 | Malinin et al. |
| 2015/0376106 A1 | 12/2015 | Batra et al. |
| 2016/0030355 A1 | 2/2016 | Kidane et al. |
| 2016/0030371 A1 | 2/2016 | Phares et al. |
| 2016/0045470 A1 | 2/2016 | Reddy et al. |
| 2016/0051505 A1 | 2/2016 | Phares et al. |
| 2016/0107973 A1 | 4/2016 | Batra et al. |
| 2016/0129087 A1 | 5/2016 | Christe et al. |
| 2016/0143868 A1 | 5/2016 | Olschewski et al. |
| 2016/0152548 A1 | 6/2016 | Gao et al. |
| 2016/0175319 A1 | 6/2016 | Freissmuth et al. |
| 2017/0095432 A1 | 4/2017 | Phares et al. |
| 2018/0153847 A1 | 6/2018 | Phares et al. |
| 2021/0054009 A1 | 2/2021 | Phares et al. |

FOREIGN PATENT DOCUMENTS

| | | |
|---|---|---|
| WO | WO-2014/110491 A1 | 7/2014 |
| WO | WO-2016/038532 A1 | 3/2016 |
| WO | WO-2016/055819 A1 | 4/2016 |
| WO | WO-2016/081658 A1 | 5/2016 |
| WO | WO-2016/105538 A1 | 6/2016 |
| WO | WO-2016/205202 A1 | 12/2016 |
| WO | WO-2018/058124 A1 | 3/2018 |
| WO | WO-2021/041320 A1 | 3/2021 |

OTHER PUBLICATIONS

Newman, A. Developing Solid Oral Dosage Forms (Second Edition), Pharmaceutical Theory and Practice, 2017, pp. 497-518.

Paudel et al., "Manufacturing of solid dispersions of poorly water soluble drugs by spray drying: Formulation and process considerations," International Journal of Pharmaceutics, 2013, 453:253-284.

Sorbera et al., "UT-15. Treatment of Pulmonary Hypertension Treatment of Peripheral Vascular Disease," Drug of the Future, 2001, 26(4):364-374.

* cited by examiner

Figure 1A

| No. | Compound | Structure | MW |
|---|---|---|---|
| 1 | Cyclopentyl Carbamate of Treprostinil (Prodrug I) | 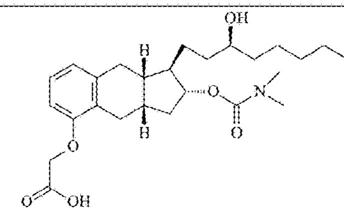 | 461.60 |
| 2 | Side Chain Carbamate of Treprostinil (Prodrug II) | 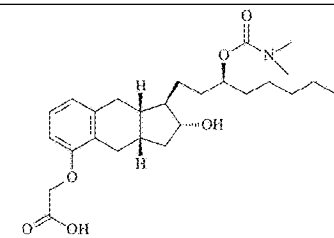 | 461.60 |
| 3 | Glycolamide of Treprostinil (Prodrug VII) | 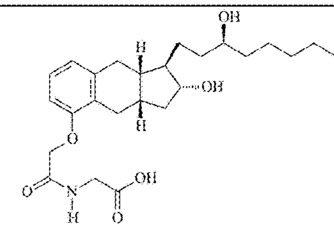 | 447.57 |
| 4 | Treprostinil acetoxy acetic acid prodrug (Prodrug XV) | 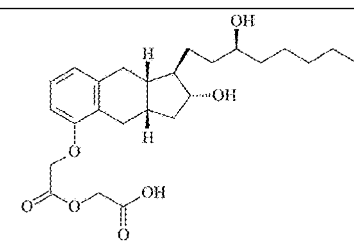 | 448.56 |

Figure 1B

| 5 | Side chain carbonate ester prodrug of treprostinil (Prodrug IV) | | 448.56 |
|---|---|---|---|
| 6 | Cyclopentyl carbonate ester prodrug of treprostinil (Prodrug III) | | 448.56 |
| 7 | Side chain N-methyl carbamate ester prodrug of treprostinil (Prodrug VIII) | | 447.57 |

Figure 1C
| 8 | Treprostinil alanine amide prodrug (Prodrug X) | 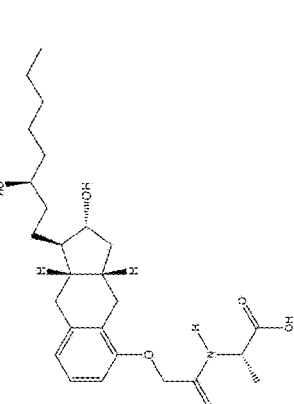 | 461.60 |
| --- | --- | --- | --- |
| 9 | Treprostinil valine amide prodrug (Prodrug XI) | 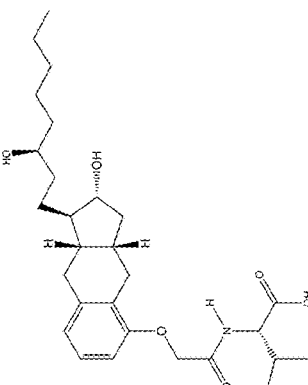 | 489.65 |
| 10 | Treprostinil aspartic acid amide prodrug (Prodrug XII) | 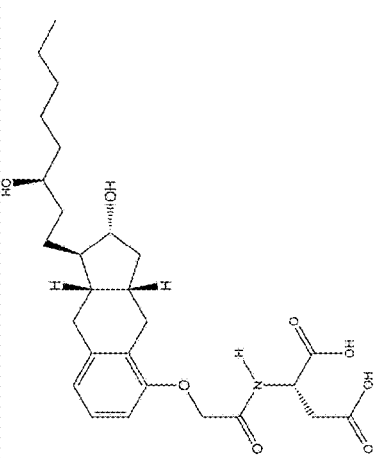 | 505.61 |

Figure 1D
| | | |
|---|---|---|
| 11 | Treprostinil serine amide prodrug <br> (Prodrug XIII) | 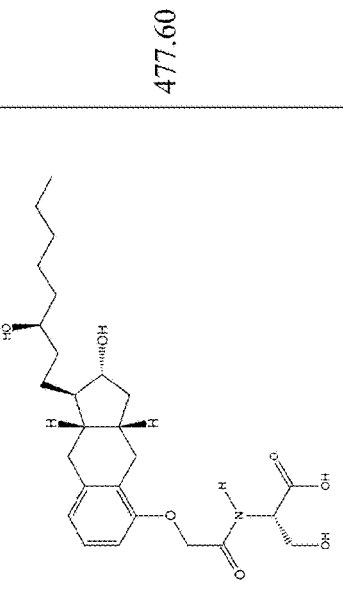 | 477.60 |
| 12 | Treprostinil sulfonamide prodrug <br> (Prodrug XIV) | 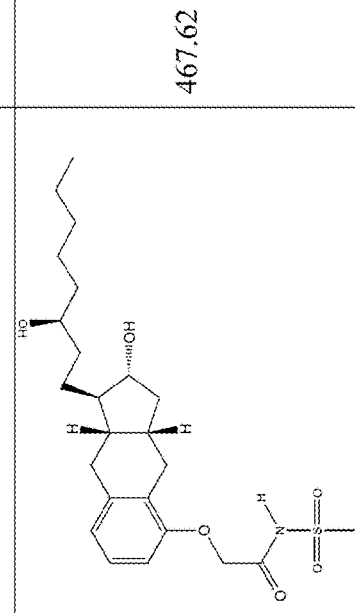 | 467.62 |
| 13 | Treprostinil side chain ethyl carbonate <br> (Prodrug XVI) <br> Chemical Formula: $C_{26}H_{38}O_7$ <br> Molecular Weight: 462.58 | 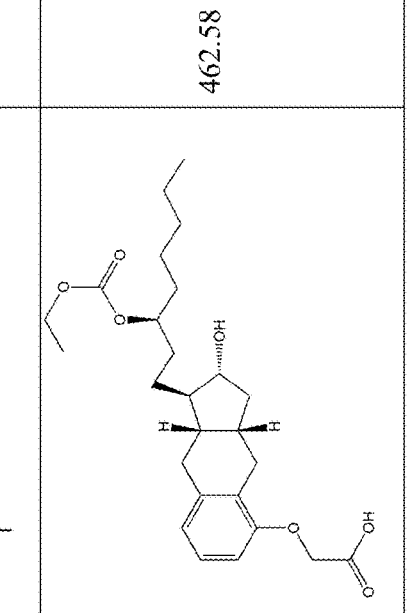 | 462.58 |

Figure 1E
| | | |
|---|---|---|
| 14 | Side Chain Isopropyl Carbonate of Treprostinil<br>(Prodrug XVII)<br>Chemical Formula: $C_{27}H_{40}O_7$<br>Molecular Weight: 476.61 | 476.61 |
| 15 | Treprostinil side-chain phosphate ester<br>(Prodrug VI)<br>Chemical Formula: $C_{23}H_{35}O_8P$<br>Molecular Weight: 470.50 | 470.50 |
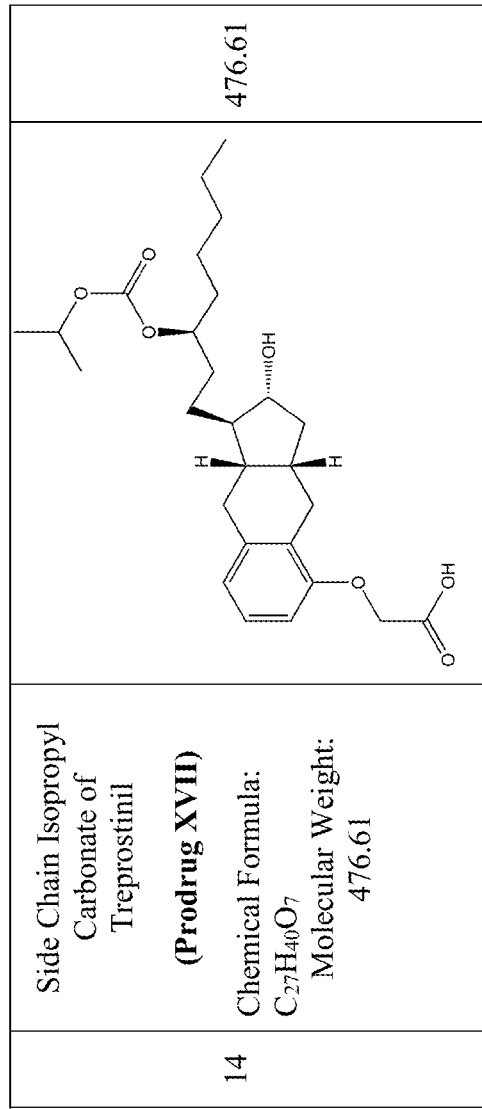
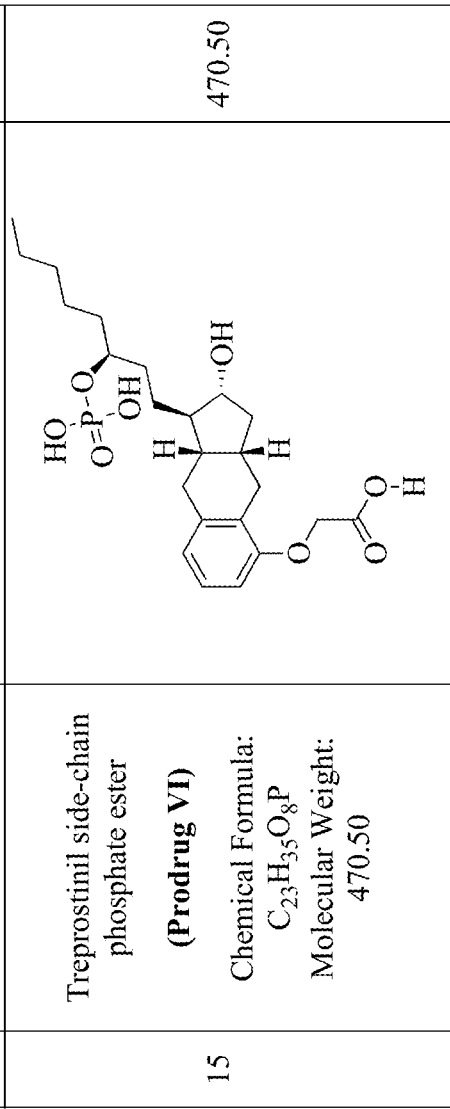

Figure 1F

| | | |
|---|---|---|
| 16 | Phosphonooxy methyl ether of treprostinil<br><br>(Prodrug XVIII)<br><br>Chemical Formula:<br>$C_{24}H_{37}O_9P$<br>Molecular Weight:<br>500.52 | 500.52 |
| 17 | Treprostinil piperidine ester<br><br>(Prodrug XIX)<br><br>Chemical Formula:<br>$C_{29}H_{43}NO_6$<br>Molecular Weight:<br>501.66 | 501.66 |

Figure 1G

| | | | |
|---|---|---|---|
| 18 | Treprostinil hemi-succinate ester (Prodrug XX) Chemical Formula: $C_{27}H_{38}O_8$ Molecular Weight: 490.59 | | 490.59 |
| 19 | Treprostinil phosphonooxyy ethyl ether (Prodrug XXI) Chemical Formula: $C_{25}H_{39}O_9P$ Molecular Weight: 514.55 | | 514.55 |
| 20 | Treprostinil Cyclopentyl Succinate (Prodrug XXII) Chemical Formula: $C_{27}H_{38}O_8$ Molecular Weight: 490.6 | | 490.59 |

Figure 1H
| | | |
|---|---|---|
| Treprostinil Side Chain Bi-piperidine Carbamate (Prodrug XXIII) Chemical Formula: $C_{34}H_{52}N_2O_6$ Molecular Weight: 584.8 | 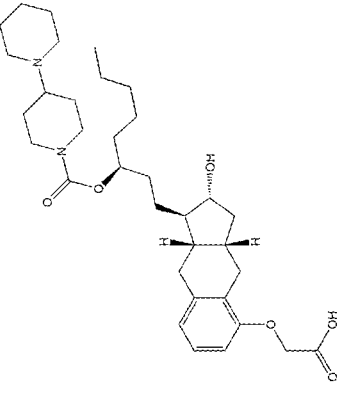 | 584.80 |
| Treprostinil Cyclic Carbonate (Prodrug XXIV) Chemical Formula: $C_{24}H_{32}O_6$ Molecular Weight: 416.51 | 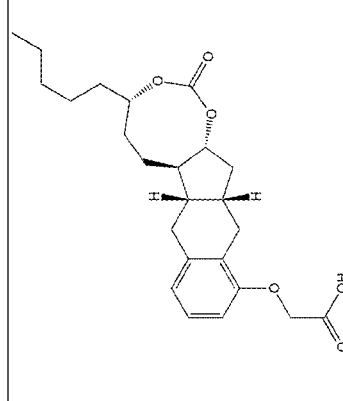 | 416.51 |
| Treprostinil Cyclopentyl Naproxen Ester (Prodrug XXV) | 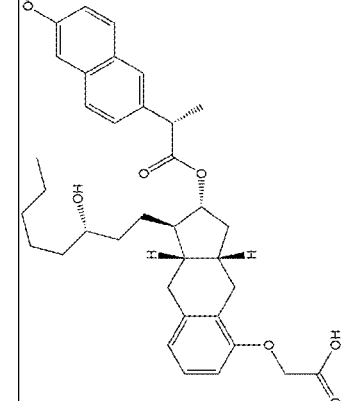 | 602.77 |

Figure 1I
| 24 | Treprostinil Side Chain isobutylphenylpropionic acid Ester<br><br>(Prodrug XXVI)<br><br>(Mix of diastereomers ~1:1)<br><br>Chemical Formula: $C_{36}H_{50}O_6$<br>Molecular Weight: 578.79 | 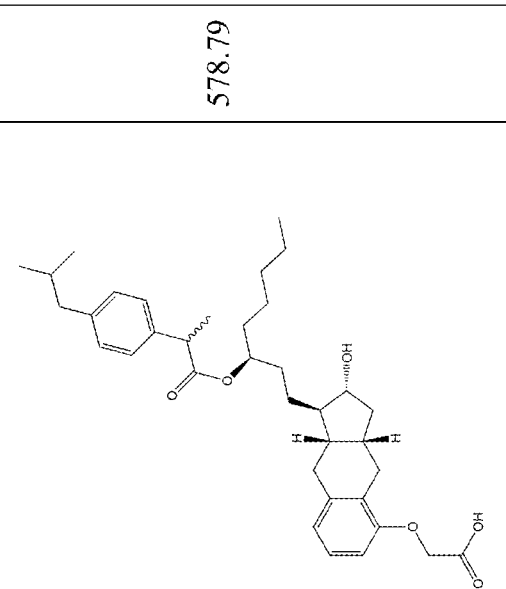 | 578.79 |
| --- | --- | --- | --- |
| 25 | Treprostinil Side Chain (6-methoxynaphthalen-2-yl)propanoic acid Ester<br><br>(Prodrug XXVII)<br><br>Chemical Formula: $C_{37}H_{46}O_7$<br>Molecular Weight: 602.77 | 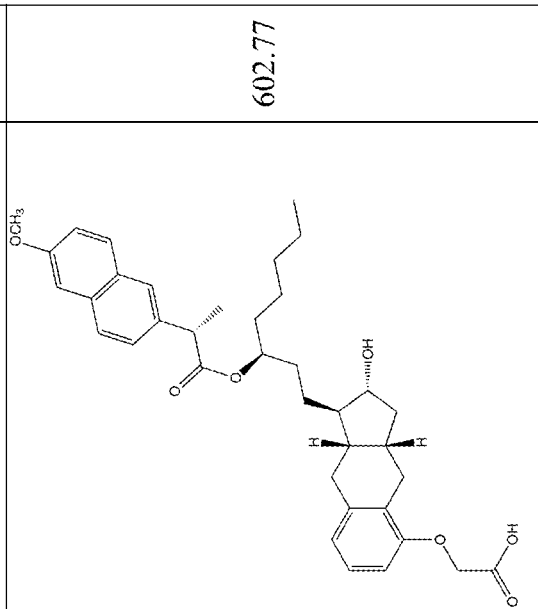 | 602.77 |

Figure 1J

| 26 | Treprostinil Cyclic Phenyl Phosphate-I (Prodrug XXVIII) Chemical Formula: $C_{29}H_{37}O_7P$ | | 528.58 |
|---|---|---|---|
| 27 | Treprostinil Side Chain L-Valine Ester (Prodrug XXIX) Chemical Formula: $C_{28}H_{43}NO_6$ | | 489.65 |

Figure 1L
| | | |
|---|---|---|
| 30 | Treprostinil side chain succinate ester N,N-dimethylamide (Prodrug XXXII) | 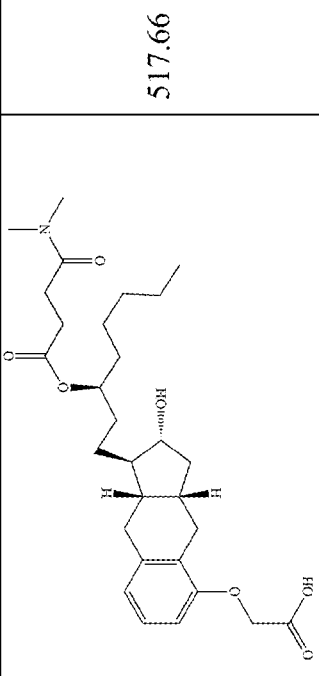 517.66 |
| 31 | Treprostinil side chain succinate ester morpholine amide (Prodrug XXXIII) | 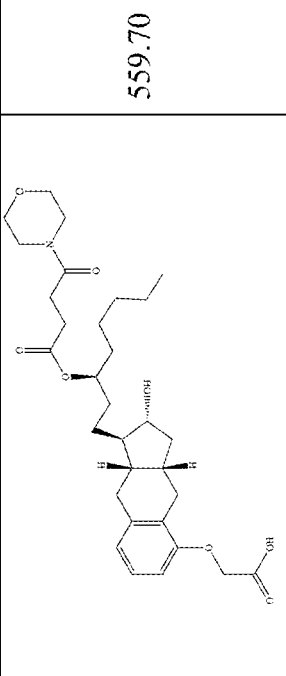 559.70 |
| 32 | Treprostinil side chain succinate ester N-methylpiperazine amide (Prodrug XXXIV) | 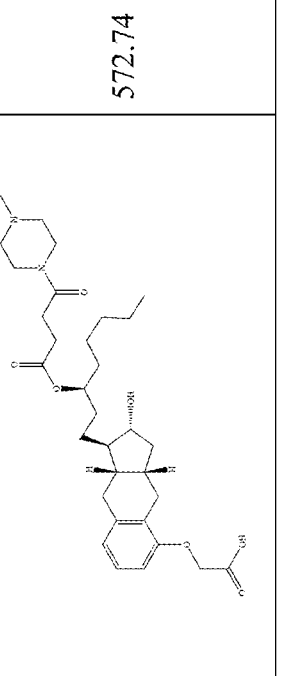 572.74 |

Figure 1M

| | | | |
|---|---|---|---|
| 33 | Treprostinil side chain lysine ester (Prodrug XXXV) | | 518.70 |
| 34 | Treprostinil side chain proline ester (Prodrug XXXVI) | | 487.64 |
| 35 | Treprostinil side chain beta-Alanine ester (Prodrug XXXVII) | | 461.60 |

Figure 1N

| 36 | Treprostinil hemi-succinate carbamate (Prodrug XXXVIII) | | 491.58 |
|---|---|---|---|
| 37 | Treprostinil hemi-succinate carbonate (Prodrug XXXIX) | | 492.57 |
| 38 | Treprostinil mono-mer PEG carbonate (Prodrug XL) | | 492.6 |

Figure 10
| 39 | Treprostinil di-mer PEG carbonate<br>(Prodrug XLI) | 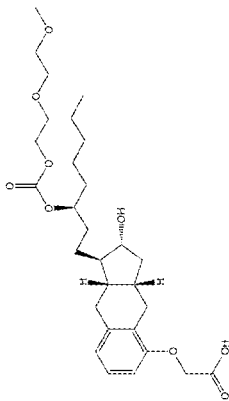 | 536.7 |
|---|---|---|---|
| 40 | Treprostinil carboxamide<br>(Prodrug XLII) | 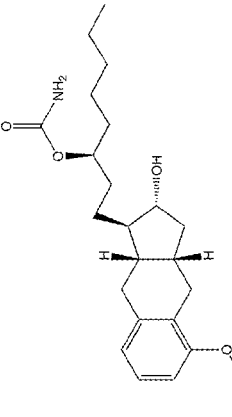 | 433.55 |
| 41 | Treprostinil acetate ester<br>(Prodrug XLIII) | 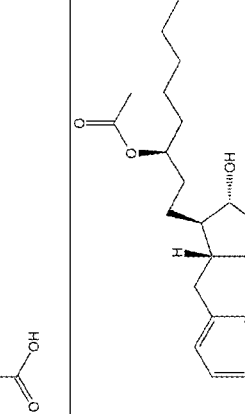 | 432.56 |

Figure 1P

| | | | |
|---|---|---|---|
| 42 | Treprostinil hydroxymethyl acetate ester (Prodrug XLIV) | | 448.56 |
| 43 | Treprostinil methyl ether (Prodrug XLV) | | 404.55 |
| 44 | Treprostinil propyl ether (Prodrug XLVI) | | 432.60 |

Figure 1Q

| | | |
|---|---|---|
| 45 | Treprostinil ethyl ether (Prodrug XLVII) | 418.57 |
| 46 | Treprostinil 4-toluate ester (Prodrug XLVIII) | 508.66 |
| 47 | Treprostinil pivaldehyde (Prodrug XLIX) | 474.64 |

Figure 1R

| 48 | Treprostinil morpholinoethyl ether (Prodrug L) | | 503.68 |
|---|---|---|---|
| 49 | Treprostinil medoxomil ether (Prodrug LI) | | 502.60 |
| 50 | Treprostinil pivoxil ether (Prodrug LII) | | 504.66 |

Figure 1S

| 51 | Treprostinil ring methyl ether (Prodrug LIII) | | 404.55 |
|---|---|---|---|
| 52 | Treprostinil phenol ether hydroxymethyl acetate ester (Prodrug LIV) | | 540.65 |
| 53 | Treprostinil proprionic ester (Prodrug LV) | | 446.58 |

Figure 1T

| 54 | Treprostinil benzoic acid ether (Prodrug LVI) | (structure) | 510.63 |
| 55 | Treprostinil acetic acid ether (Prodrug LVII) | (structure) | 448.56 |
| 56 | Treprostinil SC 4-hydroxypiperidine carbamate (Prodrug LVIII) | (structure) | 517.66 |

Figure 1U
| | | |
|---|---|---|
| 57 | Treprostinil SC ethanol carbamate (Prodrug LIX) 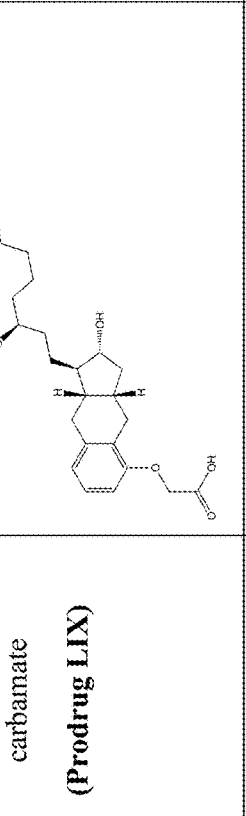 | 477.60 |
| 58 | Treprostinil SC m-hydroxy benzoic ester (Prodrug LX) 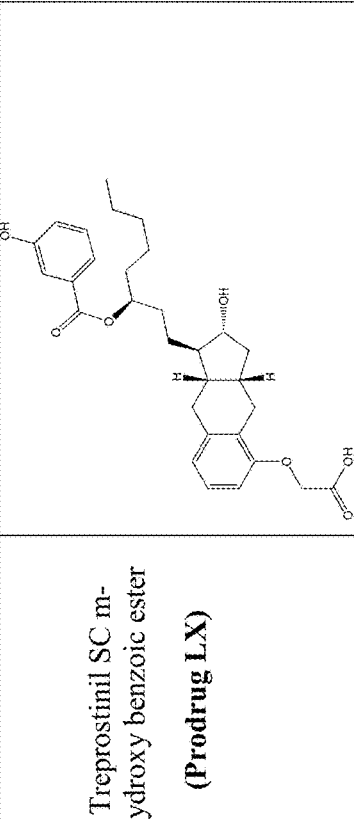 | 510.63 |
| 59 | Treprostinil SC o-hydroxy benzoic ester (Prodrug LXI) 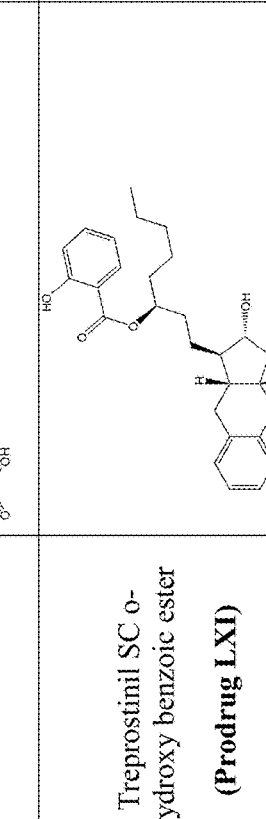 | 510.63 |

Figure 1V

| 60 | Treprostinil SC p-trifluoromethyl benzoic ester<br>(Prodrug LXII) | | 562.63 |
|---|---|---|---|
| 61 | Treprostinil SC p-trifluoromethoxybenzoic ester<br>(Prodrug LXIII) | | 578.63 |
| 62 | Treprostinil SC p-trifluoromethoxy phenoxyacetate ester<br>(Prodrug LXIV) | | 608.65 |

Figure 1W
| | | | |
|---|---|---|---|
| 63 | Treprostinil SC phenoxyacetate ester (Prodrug LXV) | 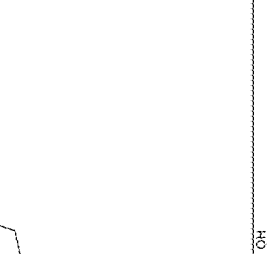 | 524.65 |
| 64 | Treprostinil SC 3,4 dihydroxy benzoic ester (Prodrug LXVI) |  | 526.63 |
| 65 | Treprostinil isobutyric ester (Prodrug LXVII) | 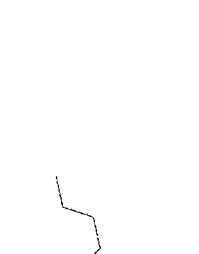 | 460.61 |

Figure 1X
| 66 | Treprostinil SC p-hydroxy benzoic ester (Prodrug LXVIII) | 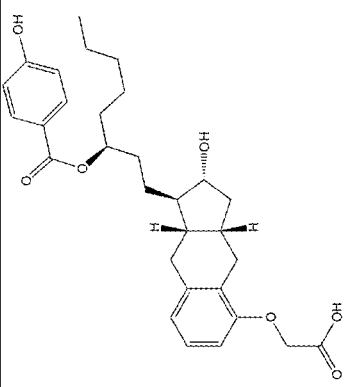 | 510.63 |
|---|---|---|---|
| 67 | Treprostinil SC adamantane ester (Prodrug LXIX) | 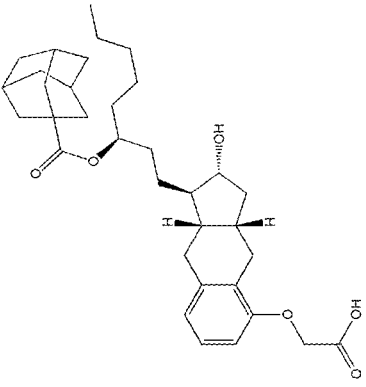 | 552.75 |
| 68 | Treprostinil diproprionic ester (Prodrug LXX) | 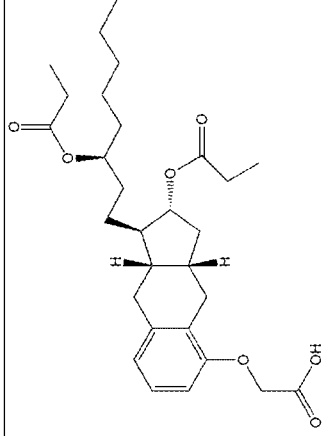 | 502.65 |

Figure 1Y

| | | | |
|---|---|---|---|
| 69 | Treprostinil dicarbonate ester (Prodrug LXXI) | [structure] | 506.59 |
| 70 | Treprostinil diacetate ester (Prodrug LXXII) | [structure] | 474.59 |
| 71 | Treprostinil diphosphate ester (Prodrug LXXIII) | [structure] | 550.48 |

STABLE TREPROSTINIL PRODRUGS

CROSS-REFERENCE TO RELATED APPLICATIONS

This application claims priority to U.S. Provisional Application No. 63/125,145, filed Dec. 14, 2020, the entire contents of which are incorporated herein by reference.

FIELD

The present application generally relates to prostacyclins and more particularly, to prodrugs of treprostinil and to methods of making and using such prodrugs.

BACKGROUND

Pulmonary hypertension is a progressive and life-threatening disease characterized by increased pressure in the pulmonary vasculature that can lead to, inter alia, heart failure.

Pulmonary hypertension (PH) has been previously classified as primary (idiopathic) or secondary. The World Health Organization (WHO) has classified pulmonary hypertension into five groups:

Group 1: pulmonary arterial hypertension (PAH);
Group 1': Pulmonary veno-occlusive disease (PVOD) and/or pulmonary capillary haemangiomatosis (PCH)
Group 2: PH with left heart disease;
Group 3: PH with lung disease and/or hypoxemia;
Group 4: PH due to chronic thrombotic and/or embolic disease; and
Group 5: miscellaneous conditions; unclear multifactorial mechanisms (e.g., sarcoidosis, histiocytosis X, lymphangiomatosis and compression of pulmonary vessels).

There are currently a number of approved products for certain types of pulmonary hypertension, including Group 1 (PAH). Those products include products containing treprostinil as the active ingredient, such as Remodulin® (treprostinil) injection. Treprostinil, however, is commonly associated with site pain when administered subcutaneously. In some cases, patients must discontinue use of subcutaneous treprostinil because the site pain is too severe. Thus, a need exists for administering treprostinil without causing site pain.

Once treprostinil is absorbed, regardless of the route of administration, its half-life is short, about 1 hour. Therefore, a need exists to prolong the half-life of treprostinil.

Another challenge associated with oral delivery of treprostinil is the high first-pass effect for treprostinil. It has been measured in animal studies to be approximately 60%. Thus, there is a need to increase the bioavailability of treprostinil, such as by modifying the first pass effect.

SUMMARY

In one embodiment, a method of treating a disease or condition comprises administering to a subject in need thereof an effective amount of a treprostinil prodrug, wherein said prodrug remains stable in a plasma of the subject 120 minutes.

In another embodiments, a method of treating a disease or condition comprises administering to a subject in need thereof an effective amount of a treprostinil prodrug, wherein said prodrug has a liver half-time of 15 minutes or less.

Yet in another embodiment, a method of treating a disease or condition comprises administering to a subject in need thereof an effective amount of a treprostinil prodrug, wherein said prodrug remains stable in a gastric and/or an intestinal fluid of greater than 120 minutes.

Yet in another embodiment, a method of treating a disease or condition comprises administering to a subject in need thereof a solution comprising an effective amount of a treprostinil prodrug, wherein said solution having pH ranging 5 to 9 and said solution after being stored for at least 1 week at a temperature from 30 C to 45 C has a treprostinil per se concentration of less than 0.5%.

In some embodiments, the disease or condition is one or more selected from the group consisting of pulmonary hypertension, congestive heart failure, peripheral vascular disease, Raynaud's phenomenon, Scleroderma, renal insufficiency, peripheral neuropathy, digital ulcers, intermittent claudication, ischemic limb disease, peripheral ischemic lesions, pulmonary fibrosis and asthma.

DETAILED DESCRIPTION

Figure 1K:
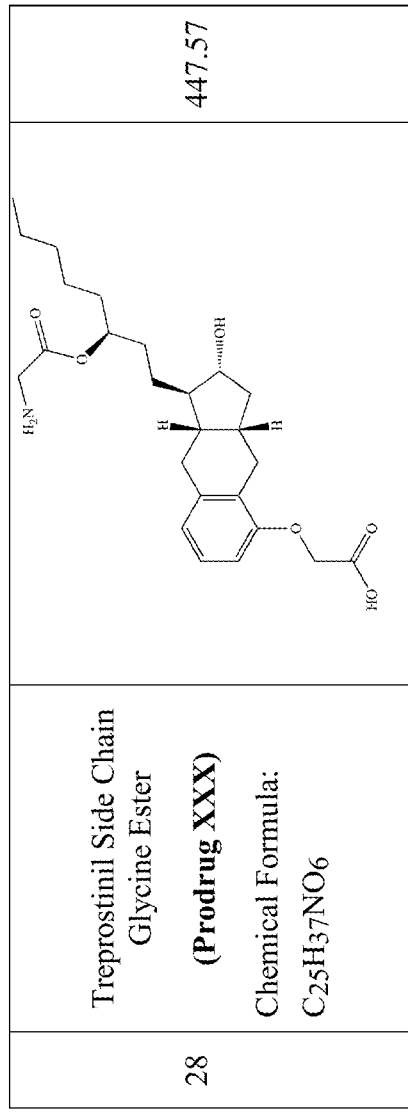
FIGS. 1A-Y show selected prodrugs.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Thus, unless context indicates otherwise, the word "or" means any one member of a particular list and also includes any combination of members of that list. Other than in the operating examples, or where otherwise indicated, all numbers expressing quantities of ingredients or reaction conditions used herein should be understood as modified in all instances by the term "about."

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims. In order that the present disclosure can be more readily understood, certain terms are first defined. Additional definitions are set forth throughout the detailed description.

All numerical designations, e.g., pH, temperature, time, concentration, and molecular weight, including ranges, are approximations which are varied (+) or (−) by increments of 0.05%, 1%, 2%, 5%, 10% or 20%. It is to be understood, although not always explicitly stated that all numerical designations are preceded by the term "about." It also is to be understood, although not always explicitly stated, that the reagents described herein are merely exemplary and that equivalents of such are known in the art.

"HPLC" refers to high-performance liquid chromatography.

"NMR" refers to nuclear magnetic resonance.

"$EC_{50}$" refers to a half maximal effective concentration of a drug or prodrug, i.e. the concentration of the drug or prodrug required to obtain a 50% effect.

As used herein, $C_m$-$C_n$, such as $C_1$-$C_{12}$, $C_1$-$C_8$, or $C_1$-$C_6$ when used before a group refers to that group containing m to n carbon atoms.

"Optionally substituted" refers to a group selected from that group and a substituted form of that group. Substituents may include any of the groups defined below. In one embodiment, substituents are selected from $C_1$-$C_{10}$ or $C_1$-$C_6$ alkyl, substituted $C_1$-$C_{10}$ or $C_1$-$C_6$ alkyl, $C_2$-$C_6$ alkenyl, $C_2$-$C_6$ alkynyl, $C_6$-$C_{10}$ aryl, $C_3$-$C_8$ cycloalkyl, $C_2$-$C_{10}$ heterocyclyl, $C_1$-$C_{10}$ heteroaryl, substituted $C_2$-$C_6$ alkenyl, substituted $C_2$-$C_6$ alkynyl, substituted $C_6$-$C_{10}$ aryl, substituted $C_3$-$C_8$ cycloalkyl, substituted $C_2$-$C_{10}$ heterocyclyl, substituted $C_1$-$C_{10}$ heteroaryl, halo, nitro, cyano, —$CO_2H$ or a $C_1$-$C_6$ alkyl ester thereof.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$), and neopentyl (($CH_3)_3CCH_2$—).

"Alkenyl" refers to monovalent straight or branched hydrocarbyl groups having from 2 to 10 carbon atoms and preferably 2 to 6 carbon atoms or preferably 2 to 4 carbon atoms and having at least 1 and preferably from 1 to 2 sites of vinyl (>C═C<) unsaturation. Such groups are exemplified, for example, by vinyl, allyl, and but 3-en-1-yl. Included within this term are the cis and trans isomers or mixtures of these isomers.

"Alkynyl" refers to straight or branched monovalent hydrocarbyl groups having from 2 to 10 carbon atoms and preferably 2 to 6 carbon atoms or preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH2C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Heteroalkyl" refers to an alkyl group one or more carbons is replaced with —O—, —S—, $SO_2$, a P containing moiety as provided herein, —$NR^Q$—,

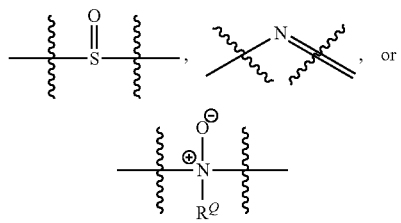

moieties where $R^Q$ is H or $C_1$-$C_6$ alkyl. Substituted heteroalkyl refers to a heteroalkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxyl, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein and with the proviso that any hydroxyl or thiol substitution is not attached to a vinyl (unsaturated) carbon atom.

"Heteroalkenyl" refers to an alkenyl group one or more carbons is replaced with —O—, —S—, SO$_2$, a P containing moiety as provided herein, —NR$^Q$—,

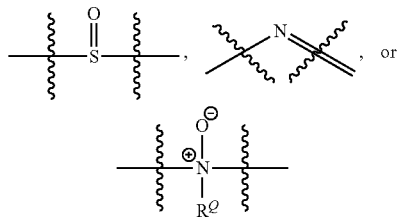

moieties where R$^Q$ is H or C$_1$-C$_6$ alkyl. Substituted heteroalkenyl refers to a heteroalkenyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Heteroalkynyl" refers to an alkynyl group one or more carbons is replaced with —O—, —S—, SO$_2$, a P containing moiety as provided herein, —NRQ-,

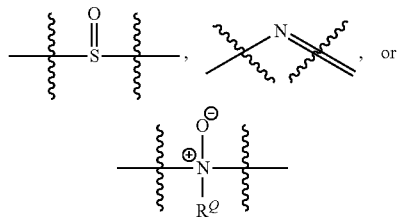

moieties where R$^Q$ is H or C$_1$-C$_6$ alkyl. Substituted heteroalkynyl refers to a heteroalkynyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Alkylene" refers to divalent saturated aliphatic hydrocarbyl groups having from 1 to 10 carbon atoms, preferably having from 1 to 6 and more preferably 1 to 3 carbon atoms that are either straight chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)— or —CH(CH$_3$)CH$_2$—), butylene (—CH$_2$CH$_2$CH$_2$CH$_2$—), isobutylene (—CH$_2$CH (CH$_3$—)CH$_2$—), sec-butylene (—CH$_2$CH$_2$(CH$_3$—)CH—), and the like. Similarly, "alkenylene" and "alkynylene" refer to an alkylene moiety containing respective 1 or 2 carbon carbon double bonds or a carbon carbon triple bond.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some embodiments, the alkylene has 1 to 2 of the aforementioned groups, or having from 1-3 carbon atoms replaced with —O—, —S—, or —NRQ- moieties where R$^Q$ is H or C$_1$-C$_6$ alkyl. It is to be noted that when the alkylene is substituted by an oxo group, 2 hydrogens attached to the same carbon of the alkylene group are replaced by "═O".

"Substituted alkenylene" and "substituted alkynylene" refer to alkenylene and substituted alkynylene moieties substituted with substituents as described for substituted alkylene.

"Alkynylene" refers to straight or branched divalent hydrocarbyl groups having from 2 to 10 carbon atoms and preferably 2 to 6 carbon atoms or preferably 2 to 3 carbon atoms and having at least 1 and preferably from 1 to 2 sites of acetylenic (—C≡C—) unsaturation. Examples of such alkynylene groups include C≡C— and CH$_2$C≡C—.

"Substituted alkynylene" refers to alkynylene groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Heteroalkylene" refers to an alkylene group wherein one or more carbons is replaced with —O—, —S—, SO$_2$, a P containing moiety as provided herein, —NR$^Q$—,

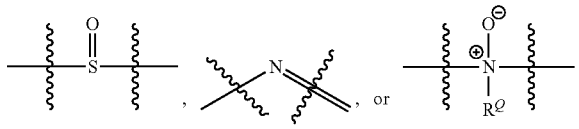

moieties where R$^Q$ is H or C$_1$-C$_6$ alkyl. "Substituted heteroalkylene" refers to heteroalkynylene groups having from 1 to 3 substituents, and preferably 1 to 2 substituents, selected from the substituents disclosed for substituted alkylene.

"Heteroalkenylene" refers to an alkenylene group wherein one or more carbons is replaced with —O—, —S—, SO$_2$, a P containing moiety as provided herein, —NR$^Q$—,

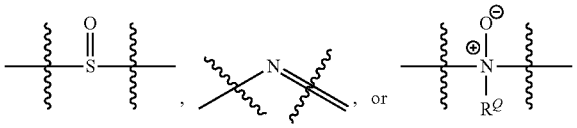

moieties where R$^Q$ is H or C$_1$-C$_6$ alkyl. "Substituted heteroalkenylene" refers to heteroalkynylene groups having from 1 to 3 substituents, and preferably 1 to 2 substituents, selected from the substituents disclosed for substituted alkenylene.

"Heteroalkynylene" refers to an alkynylene group wherein one or more carbons is replaced with —O—, —S—, SO$_2$, a P containing moiety as provided herein, —NR$^Q$—,

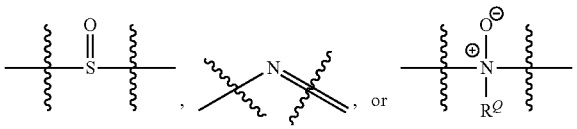

moieties where R$^Q$ is H or C$_1$-C$_6$ alkyl. "Substituted heteroalkynylene" refers to heteroalkynylene groups having from 1 to 3 substituents, and preferably 1 to 2 substituents, selected from the substituents disclosed for substituted alkynylene.

"Alkoxy" refers to the group O alkyl wherein alkyl is defined herein. Alkoxy includes, by way of example, methoxy, ethoxy, n propoxy, isopropoxy, n butoxy, t butoxy, sec butoxy, and n pentoxy.

"Substituted alkoxy" refers to the group O (substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group CH$_3$C(O)—.

"Acylamino" refers to the groups —NR$^{47}$C(O)alkyl, —NR$^{47}$C(O) substituted alkyl, —NR$^{47}$C(O)cycloalkyl, —NR$^{47}$C(O) substituted cycloalkyl, —NR$^{47}$C(O)cycloalkenyl, —NR$^{47}$C(O) substituted cycloalkenyl, —NR$^{47}$C(O) alkenyl, —NR$^{47}$C(O) substituted alkenyl, —NR$^{47}$C(O) alkynyl, —NR$^{47}$C(O) substituted alkynyl, —NR$^{47}$C(O)aryl, —NR$^{47}$C(O) substituted aryl, —NR$^{47}$C(O)heteroaryl, —NR$^{47}$C(O) substituted heteroaryl, —NR$^{47}$C(O)heterocyclic, and NR$^{47}$C(O) substituted heterocyclic wherein R$^{47}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl —C(O)O, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group $NH_2$.

"Substituted amino" refers to the group $-NR^{48}R^{49}$ where $R^{48}$ and $R^{49}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, $SO_2$ a-lkyl, $-SO_2$-substituted alkyl, $-SO_2$-alkenyl, $-SO_2$-substituted alkenyl, $-SO_2$-cycloalkyl, $-SO_2$-substituted cycloalkyl, $-SO_2$-cycloalkenyl, $-SO_2$-substituted cylcoalkenyl, $-SO_2$-aryl, $-SO_2$-substituted aryl, $-SO_2$-heteroaryl, $-SO_2$-substituted heteroaryl, $-SO_2$-heterocyclic, and $-SO_2$-substituted heterocyclic and wherein $R^{48}$ and $R^{49}$ are optionally joined, together with the nitrogen bound thereto to form a heterocyclic or substituted heterocyclic group, provided that $R^{48}$ and $R^{49}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^{48}$ is hydrogen and $R^{49}$ is alkyl, the substituted amino group is sometimes referred to herein as alkylamino. When $R^{48}$ and $R^{49}$ are alkyl, the substituted amino group is sometimes referred to herein as dialkylamino. When referring to a monosubstituted amino, it is meant that either $R^{48}$ or $R^{49}$ is hydrogen but not both. When referring to a disubstituted amino, it is meant that neither $R^{48}$ nor $R^{49}$ are hydrogen.

"Aminocarbonyl" refers to the group $-C(O)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group $-C(S)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group $-NR^{47}C(O)NR^{50}R^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group $-NR^{47}C(S)NR^{50}R^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group $-O-C(O)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group $-SO_2NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group $-O-SO_2NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^{47}$SO$_2$NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^{52}$)NR$^{50}$R$^{51}$ where R$^{50}$, R$^{51}$, and R$^{52}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2 benzoxazolinone, 2H 1,4 benzoxazin 3(4H) one 7 yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Arylene" refers to a divalent aromatic carbocyclic group of from 6 to 14 carbon atoms having a single ring or multiple condensed rings. "Substituted arylene" refers to an arylene having from 1 to 5, preferably 1 to 3, or more preferably 1 to 2 substituents as defined for aryl groups.

"Heteroarylene" refers to a divalent aromatic group of from 1 to 10 carbon atoms and 1 to 4 heteroatoms selected from the group consisting of oxygen, nitrogen and sulfur within the ring. "Substituted heteroarylene" refers to heteroarylene groups that are substituted with from 1 to 5, preferably 1 to 3, or more preferably 1 to 2 substituents selected from the group consisting of the same group of substituents defined for substituted aryl.

"Aryloxy" refers to the group —O-aryl, where aryl is as defined herein, that includes, by way of example, phenoxy and naphthoxy.

"Substituted aryloxy" refers to the group —O— (substituted aryl) where substituted aryl is as defined herein.

"Arylthio" refers to the group —S-aryl, where aryl is as defined herein.

"Substituted arylthio" refers to the group S (substituted aryl), where substituted aryl is as defined herein.

"Carbonyl" refers to the divalent group —C(O)— which is equivalent to —C(=O)—.

"Carboxyl" or "carboxy" refers to COOH or salts thereof.

"Carboxyl ester" or "carboxy ester" refers to the group —C(O)(O)-alkyl, —C(O)(O)-substituted alkyl, —C(O)O-alkenyl, —C(O)(O)-substituted alkenyl, —C(O)(O)-alkynyl, —C(O)(O)-substituted alkynyl, —C(O)(O)-aryl, —C(O)(O)-substituted-aryl, —C(O)(O)-cycloalkyl, —C(O)(O)-substituted cycloalkyl, —C(O)(O)-cycloalkenyl, —C(O)(O)-substituted cycloalkenyl, —C(O)(O)-heteroaryl, —C(O)(O)-substituted heteroaryl, —C(O)(O)-heterocyclic, and —C(O)(O)-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino refers to the group —NR$^{47}$C(O)(O)-alkyl, —NR$^{47}$C(O)(O)-substituted alkyl, —NR$^{47}$C(O)O-alkenyl, —NR$^{47}$C(O)(O)-substituted alkenyl, —NR$^{47}$C(O)(O)-alkynyl, —NR$^{47}$C(O)(O)-substituted alkynyl, —NR$^{47}$C(O)(O)-aryl, —NR$^{47}$C(O)(O)-substituted-aryl, —NR$^{47}$C(O)(O)-cycloalkyl, —NR$^{47}$C(O)(O)-substituted cycloalkyl, —NR$^{47}$C(O)(O)-cycloalkenyl, —NR$^{47}$C(O)(O)-substituted cycloalkenyl, —NR$^{47}$C(O)(O)-heteroaryl, —NR$^{47}$C(O)(O)-substituted heteroaryl, —NR$^{47}$C(O)(O)-heterocyclic, and —NR$^{47}$C(O)(O)-substituted heterocyclic wherein R$^{47}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)(O)-substituted alkynyl, —O—C(O)O-aryl, —O—C(O)O-substituted-aryl, —O—C(O)O-cycloalkyl, —O—C(O)O— substituted cycloalkyl, —O—C(O)O-cycloalkenyl, —O—C(O)O-substituted cycloalkenyl, —O—C(O)O— heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group CN.

"Cycloalkyl" refers to cyclic alkyl groups of from 3 to 10 carbon atoms having single or multiple cyclic rings including fused, bridged, and spiro ring systems. The fused ring can be an aryl ring provided that the non aryl part is joined to the rest of the molecule. Examples of suitable cycloalkyl groups include, for instance, adamantyl, cyclopropyl, cyclobutyl, cyclopentyl, and cyclooctyl.

"Cycloalkenyl" refers to non aromatic cyclic alkyl groups of from 3 to 10 carbon atoms having single or multiple cyclic rings and having at least one >C=C<ring unsaturation and preferably from 1 to 2 sites of >C=C<ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Cyclopropano" refers to:

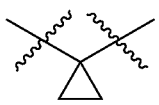

"Cyclobutano" refers to:

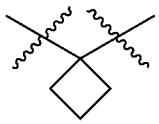

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{53}$C(=NR$^{53}$)N(R$^{53}$)$_2$ where each R$^{53}$ is independently selected from the group consisting of hydrogen, alkyl, substituted alkyl, aryl, substituted aryl, heteroaryl, substituted heteroaryl, cycloalkyl, substituted cycloalkyl, heterocyclic, and substituted heterocyclic and two R$^{53}$ groups attached to a common guanidino nitrogen atom are optionally joined together with the nitrogen bound thereto to form a heterocyclic or substituted heterocyclic group, provided that at least one R$^{53}$ is not hydrogen, and wherein said substituents are as defined herein.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N oxide (N→O), sulfinyl, or sulfonyl moieties. Certain non-limiting examples include pyridinyl, pyrrolyl, indolyl, thiophenyl, oxazolyl, thizolyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more of the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, furan, thiophene, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4 tetrahydroisoquinoline, 4,5,6,7 tetrahydrobenzo[b]thiophene, thiazole, thiazolidine, thiophene, benzo[b]thiophene, morpholinyl, thiomorpholinyl (also referred to as thiamorpholinyl), 1,1 dioxothiomorpholinyl, piperidinyl, pyrrolidine, and tetrahydrofuranyl.

"Nitro" refers to the group —NO$_2$.

"Oxo" refers to the atom (=O).

Phenylene refers to a divalent aryl ring, where the ring contains 6 carbon atoms.

Substituted phenylene refers to phenylenes which are substituted with 1 to 4, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Spirocycloalkyl" and "spiro ring systems" refers to divalent cyclic groups from 3 to 10 carbon atoms having a cycloalkyl or heterocycloalkyl ring with a spiro union (the union formed by a single atom which is the only common member of the rings) as exemplified by the following structure:

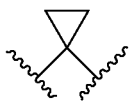

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl —SO$_2$—, phenyl —SO$_2$—, and 4-methylphenyl-SO$_2$—.

"Substituted sulfonyloxy" refers to the group —OSO$_2$-alkyl, —OSO$_2$-substituted alkyl, —OSO$_2$-alkenyl, —OSO$_2$-substituted alkenyl, OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group SH.

"Thiocarbonyl" refers to the divalent group —C(S)— which is equivalent to —C(=S)—.

"Thioxo" refers to the atom (=S).

"Alkylthio" refers to the group S-alkyl wherein alkyl is as defined herein.

"Substituted alkylthio" refers to the group —S-(substituted alkyl) wherein substituted alkyl is as defined herein.

A substituted ring can be substituted with one or more fused and/or spiro cycles. Such fused cycles include a fused cycloalkyl, a fused heterocyclyl, a fused aryl, a fused heteroaryl ring, each of which rings can be unsubstituted or substituted. Such spiro cycles include a fused cycloalkyl and a fused heterocyclyl, each of which rings can be unsubstituted or substituted.

It is understood that the above definitions are not intended to include impermissible substitution patterns (e.g., methyl substituted with 5 fluoro groups). Such impermissible substitution patterns are well known to the skilled artisan.

It is understood that the above definitions are not intended to include impermissible substitution patterns (e.g., methyl substituted with 5 fluoro groups). Such impermissible substitution patterns are well known to the skilled artisan.

"Pharmaceutically acceptable salt" refers to salts of a compound, which salts are suitable for pharmaceutical use and are derived from a variety of organic and inorganic counter ions well known in the art and include, when the compound contains an acidic functionality, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate (see Stahl and Wermuth, eds., "Handbook of Pharmaceutically Acceptable Salts," (2002), Verlag Helvetica Chimica Acta, Zurich, Switzerland), for a discussion of pharmaceutical salts, their selection, preparation, and use.

"Pulmonary hypertension" refers to all forms of pulmonary hypertension, WHO Groups 1-5. Pulmonary arterial hypertension, also referred to as PAH, refers to WHO Group 1 pulmonary hypertension. PAH includes idiopathic, heritable, drug- or toxin-induced, and persistent pulmonary hypertension of the newborn (PPHN).

Generally, pharmaceutically acceptable salts are those salts that retain substantially one or more of the desired pharmacological activities of the parent compound and which are suitable for in vivo administration. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like.

Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4 chlorobenzenesulfonic acid, 2-naphthalenesulfonic acid, 4-toluenesulfonic acid, camphorsulfonic acid, etc.), glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or by an ammonium ion (e.g., an ammonium ion derived from an organic base, such as, ethanolamine, diethanolamine, triethanolamine, morpholine, piperidine, dimethylamine, diethylamine, triethylamine, and ammonia).

Treprostinil, the active ingredient in Remodulin® (treprostinil) Injection, Tyvaso® (treprostinil) Inhalation Solution, and Orenitram® (treprostinil) Extended Release Tablets, was described in U.S. Pat. No. 4,306,075. Methods of making treprostinil and other prostacyclin derivatives are described, for example, in Moriarty, et al., *J. Org. Chem.* 2004, 69, 1890-1902, *Drug of the Future*, 2001, 26(4), 364-374, U.S. Pat. Nos. 6,441,245, 6,528,688, 6,700,025, 6,809,223, 6,756,117, 8,461,393, 8,481,782; 8,242,305, 8,497,393, 8,940,930, 9,029,607, 9,156,786 and 9,388,154 9,346,738; U.S. Published Patent Application Nos. 2012-0197041, 2013-0331593, 2014-0024856, 2015-0299091, 2015-0376106, 2016-0107973, 2015-0315114, 2016-0152548, and 2016-0175319; PCT Publication No. WO2016/0055819 and WO2016/081658.

Various uses and/or various forms of treprostinil are disclosed, for examples, in U.S. Pat. Nos. 5,153,222, 5,234, 953, 6,521,212, 6,756,033, 6,803,386, 7,199,157, 6,054,486, 7,417,070, 7,384,978, 7,879,909, 8,563,614, 8,252,839, 8,536,363, 8,410,169, 8,232,316, 8,609,728, 8,350,079, 8,349,892, 7,999,007, 8,658,694, 8,653,137, 9,029,607, 8,765,813, 9,050,311, 9,199,908, 9,278,901, 8,747,897, 9,358,240, 9,339,507, 9,255,064, 9,278,902, 9,278,903, 9,758,465; 9,422,223; 9,878,972; 9,624,156; U.S. Published Patent Application Nos. 2009-0036465, 2008-0200449, 2008-0280986, 2009-0124697, 2014-0275616, 2014-0275262, 2013-0184295, 2014-0323567, 2016-0030371, 2016-0051505, 2016-0030355, 2016-0143868, 2015-0328232, 2015-0148414, 2016-0045470, 2016-0129087, 2017-0095432; 2018-0153847 and PCT Publications Nos. WO00/57701, WO20160105538, WO2016038532, WO2018/058124.

Treprostinil has the following chemical formula:

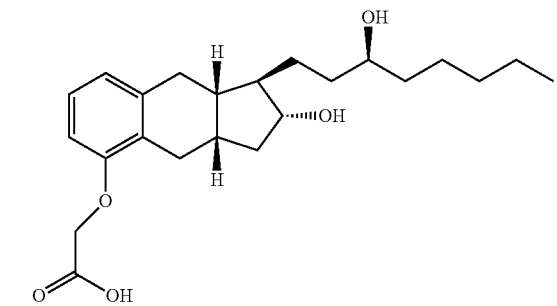 [SMILES: CCCCC[C@H](O)CC[C@@H]1[C@H]2Cc3cccc(OCC(=O)O)c3C[C@H]2C[C@H]1O]

The term "effective amount" may mean an amount of a treprostinil prodrug, which may be necessary to treat the disease or condition. In some embodiments, an effective amount of treprostinil prodrug may be the same or similar to an effective amount of treprostinil for treating the same disease or condition. In some embodiments, an effective amount of treprostinil prodrug may be different from an effective amount of treprostinil for treating the same disease or condition. A person of ordinary skill in the art would be able to determine and "effective amount" of the treprostinil prodrug based, for example, on the relevant disease or condition, the amount of treprostinil known to treat, ameliorate, or prevent the disease or condition, and the rate at which the prodrug converts to treprostinil in vivo.

In some embodiments, the prodrug may be a prodrug disclosed in U.S. Pat. Nos. 7,384,978, 7,417,070, 7,544,713, 8,252,839, 8,410,169, 8,536,363, 9,050,311, 9,199,908, 9,278,901, 9,422,223 and 9,624,156, each of which is incorporated herein by reference in their entirety.

In some embodiments, the prodrug may be a prodrug disclosed in U.S. Pat. Nos. 9,371,264, 9,394,227, 9,505,737, and 9,643,911, each of which is incorporated herein by reference in their entirety.

In some embodiments, the prodrug may be a prodrug disclosed in U.S. Patent Application Publication 2018-0153847, which incorporated by reference in its entirety.

In some embodiments, the prodrug may be a prodrug disclosed in U.S. application Ser. No. 17/001,123 and/or U.S. Provisional Patent Applications Nos. 62/890,839 and 62/976,183, each of which is incorporated herein by reference in their entirety.

In some embodiments, the prodrug may be one of prodrugs discussed below.

Prodrug Compounds

In one aspect, a compound having the following formula:

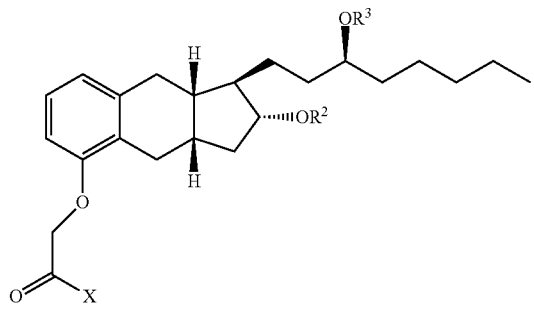

or pharmaceutically acceptable salt thereof, is provided wherein:

X is $OR^{14}$, $-NR^1_2R^1$, $-NR^1CO_2H$,

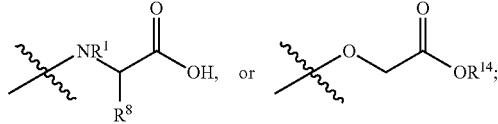

wherein:
  each $R^1$ is independently H or $C_1$-$C_4$ alkyl and $R^8$ is optionally substituted $C_1$-$C_6$ alkyl or the side group of an amino acid, or $R^1$ and $R^8$ together form 4-7 membered heterocycle;
  $R^{14}$ is a H, optionally substituted $C_1$-$C_6$ alkyl, a first drug moiety, or:

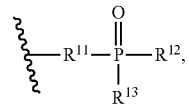

wherein $R^{11}$ is absent, an optionally substituted $C_1$-$C_6$ alkylene, or $-Q^1-O-$ wherein $Q^1$ is optionally substituted $C_1$-$C_6$ alkylene; and each of $R^{12}$ and $R^{13}$ are independently selected from H, OH, optionally substituted $C_1$-$C_6$ alkoxy, optionally substituted $C_1$-$C_6$ alkyl, optionally substituted $C_1$-$C_6$ alkenyl, optionally substituted $C_1$-$C_8$ cycloalkyl, optionally substituted $C_1$-$C_{10}$ aryl;

each of $R^2$ and $R^3$ independently is a second drug moiety or a third drug moiety, H, a phosphorous containing group, $-C(O)R^6$, or an -A-B-C substituent, wherein:
  A is optionally substituted $C_1$-$C_6$ alkylene, $-NR^6-$, $-C(O)-$, $-C(O)O-$, or $-C(O)NR^6-$;
  B is a bond, optionally substituted $C_1$-$C_6$ alkylene, $-C(O)-$, $-O-$, $-S-$, heterocyclyl; and
  C is optionally substituted heterocyclyl, optionally substituted heteroaryl, optionally substituted aryl, optionally substituted cycloalkyl, $-(OCH_2CH_2)_q-OR^6$, $-C(O)N(R^6)_2$, $-C(O)N(R^{18})_2$, $-C(O)R^6$, $-CO_2H$, $-OR^6$, $-N(R^{18})_2$, $-N(R^6)_2$, or

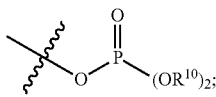

wherein:
  both $R^{18}$ together form an optionally substituted 3-8 membered heterocyclyl;
  each $R^6$ is independently H, optionally substituted $C_1$-$C_6$ alkyl, optionally substituted heteroaryl, optionally substituted aryl, or both of $R^6$ together form an 4 to 8 membered optionally substituted heterocyclyl or a 5 membered optionally substituted heteroaryl;
  or $R^2$ and $R^3$ are joined together to form $-C(O)-$, $-SO_2-$,

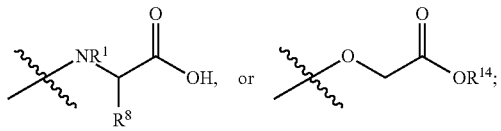

in an 8-12 membered heterocyclyl, wherein
  each $R^{10}$ is H, optionally substituted $C_1$-$C_6$ alkyl, optionally substituted $C_1$-$C_6$ alkenyl, optionally substituted cycloalkyl, optionally substituted heteroaryl, or optionally substituted aryl; and
  q is 0, 1, 2, 3, 4, 5 or 6;
provided that:
  when A is $-C(O)-$ B is not a bond and C is not $-N(R^6)_2$;
  when A is $-C(O)-$ B is not a bond and C is not $-OR^6$;
  $R^{14}$, $R^2$ and $R^3$ are not H
  when X is OH, $R^2$ and $R^3$ are not H;
  when $R^8$ is H then at least one of $R^2$ and $R^3$ is not H.

In one aspect, a compound having the following formula:

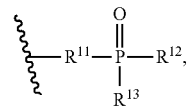

or pharmaceutically acceptable salt thereof, is provided wherein:

X is $OR^{14}$, $-NR^1SO_2R^1$, $-NR^1CO_2H$,

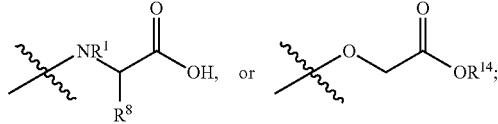

wherein:
  each $R^1$ is independently H or $C_1$-$C_4$ alkyl and $R^8$ is $C_1$-$C_6$ alkyl or the side group of an amino acid, or $R^1$ and $R^8$ together form 4-7 membered heterocycle;
  $R^{14}$ is a H, $C_1$-$C_6$ alkyl, a first drug moiety, or:

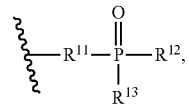

wherein $R^{11}$ is absent, a $C_1$-$C_6$ alkylene, or $-Q^1-O-$ wherein $Q^1$ is $C_1$-$C_6$ alkylene; and each of $R^{12}$ and $R^{13}$ are independently selected from H, OH, $C_1$-$C_6$ alkoxy, $C_1$-$C_6$ alkyl, $C_1$-$C_6$ alkenyl, $C_1$-$C_8$ cycloalkyl, $C_1$-$C_{10}$ aryl;

each of $R^2$ and $R^3$ independently is a second drug moiety or a third drug moiety, H, a phosphorous containing group, $-C(O)R^6$, or an -A-B-C substituent, wherein:
  A is $C_1$-$C_6$ alkylene, $-NR^6-$, $-C(O)-$, $-C(O)O-$, or $-C(O)NR^6-$;

B is a bond, $C_1$-$C_6$ alkylene, —C(O)—, —O—, —S—, heterocyclyl; and

C is heterocyclyl, heteroaryl, aryl, cycloalkyl, —(OCH$_2$CH$_2$)$_q$—OR$^6$, —C(O)N(R$^6$)$_2$, —C(O)N(R$^{18}$)$_2$, —C(O)R$^6$, —CO$_2$H, —OR$^6$, —N(R$^{18}$)$_2$, —N(R$^6$)$_2$, or

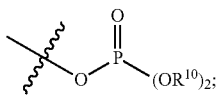

wherein:
both R$^{18}$ together form an 3-8 membered heterocyclyl;
each R$^6$ is independently H, $C_1$-$C_6$ alkyl, heteroaryl, aryl, or both of R$^6$ together form an 4 to 8 membered heterocyclyl or a 5 membered heteroaryl;
or R$^2$ and R$^3$ are joined together to form —C(O)—, —SO$_2$—,

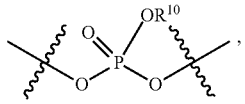

in an 8-12 membered heterocyclyl, wherein
each R$^{10}$ is H, $C_1$-$C_6$ alkyl, $C_1$-$C_6$ alkenyl, cycloalkyl, heteroaryl, or aryl; and
q is 0, 1, 2, 3, 4, 5 or 6;
provided that:
when A is —C(O)— B is not a bond and C is not —N(R$^6$)$_2$;
when A is —C(O)— B is not a bond and C is not —OR$^6$;
R$^4$, R$^2$ and R$^3$ are not H
when X is OH, R$^2$ and R$^3$ are not H;
when R$^8$ is H then at least one of R$^2$ and R$^3$ is not H.

In some embodiments, X is OR$^{14}$, R$^{14}$ is H or a first drug moiety, R$^2$ is H or a second drug moiety, and R$^3$ is H or a third drug moiety, with a proviso that each of R$^4$, R$^2$ and R$^3$ is not H.

In some embodiments, R$^{14}$ is H, one of R$^2$ and R$^3$ is H and the other of R$^2$ and R$^3$ is a drug moiety. In some embodiments, R$^2$ is H and R$^3$ is a third drug moiety. In some embodiments, R$^2$ is a second drug moiety and R$^3$ is a third drug moiety. In some embodiments, each of R$^{12}$, R$^{13}$, R$^2$ and R$^3$ are each H, and R$^{11}$ is $C_1$-$C_4$ alkylene.

In some embodiments, R$^{14}$ is $C_1$-$C_4$ alkyl, which may be optionally substituted with a terminal hydroxyl or carboxy group. When R$^{14}$ is $C_1$-$C_4$ alkyl is substituted with a terminal carboxy group, R$^1$ may be carboxymethyl, carboxyethyl, carboxypropyl, 4-carboxybutyl, 2-methyl-3-carboxy propyl.

Each drug moiety (first, second, and third) may be independently selected. In some embodiments, the drug moiety is a pain relief drug moiety. In some embodiments, the drug moiety is a nonsteroidal anti-inflammatory drug (NSAID) moiety. The drug moiety may be selected from any pain relief or NSAID drug known in the art conjugated to the compound. Conjugation may include direct covalent attachment or attachment by way of a linker group. Linkers may include optionally substituted alkylene groups, optionally substituted arylene or heteroarylene groups, peptides, or other linkers known in the art of drug conjugation. Exemplary pain relief drugs include, but are not limited to opioids (e.g. morphine, hydrocodone, oxycodone, oxymorphone, hydromorphone, fentanyl, thiofentanyl, tapentadol, methadone or meperidine); local anesthetics (e.g. lidocaine, prilocaine, tetracaine, articaine, benzocaine, chloroprocaine, cocaine, cyclomethycaine, dimethocaine, piperocaine, propoxycaine, proparacaine, saxitoxin, neosaxitoxin, tetrodotoxin, menthol, eugenol, and spilanthol); and acetaminophen. Non-limiting examples of non-steroidal anti-inflammatory drugs (NSAIDS) include aspirin, ibuprofen, celecoxib or any COX1 or COX2 inhibitor, or naproxen.

The second drug moiety may form an ester bond with a carboxylic group of treprostinil and/or one or both hydroxyl groups (e.g. R$^2$ or R$^3$ is H) of treprostinil. For example, when the second drug moiety comprises a hydroxyl group, it may form an ester bond with the carboxylic group of treprostinil. When the second drug moiety comprises a carboxylic group, it may form an ester bond with one of hydroxyl groups of treprostinil.

In some embodiments, only one of R$^2$ and R$^3$ is a phosphorous containing group. In some embodiments, both R$^2$ and R$^3$ are a phosphorous containing group. In some embodiments, each phosphorous containing group independently has the formula:

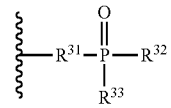

wherein R$^{31}$ is absent, optionally substituted $C_1$-$C_6$ alkylene, or -Q-O— wherein Q is optionally substituted $C_1$-$C_6$alkylene; and
each of R$^{32}$ and R$^{33}$ are independently selected from H, optionally substituted $C_1$-$C_6$ alkoxy, optionally substituted $C_1$-$C_6$ alkenyloxy, optionally substituted $C_1$-$C_6$ cycloalkoxy, and optionally substituted aryloxy. In some embodiments, the phosphorous containing group has the formula

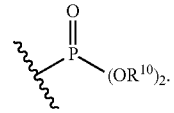

In some embodiments, R$^{31}$ is $C_1$-$C_6$ alkylene and each of R$^{32}$ and R$^{33}$ are H. In some embodiments, X is OH, —OCH$_2$OPO$_3$H$_2$,

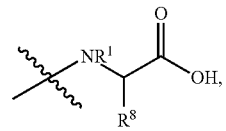

or —NHSO$_2$CH$_3$; wherein R$^8$ is $C_1$-$C_2$ alkyl optionally substituted with OH or —CO$_2$H. In some embodiments, X is

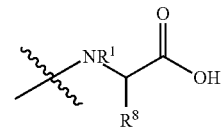

wherein R⁸ is methyl. In some embodiments, R⁸ is methyl substituted with OH. In some embodiments, R⁸ is methyl substituted with —CO₂H. In some embodiments, R⁸ is the side group of an amino acid as defined herein. In some embodiments, R¹ and R⁸ together form a pyrrolidine, piperidine, aziridine, azepane, or azetidine. In some embodiments R¹ and R⁸ together form a pyrrolidine.

In some embodiments, R² is —C(O)R¹⁷, —OPO₃H₂ or -A-B—C wherein:
  A is —C(O)—, —C(O)O—, CH₂, or —C(O)NR⁶—;
  B is —CHR¹⁶— or —(CH₂)$_q$—; and
  C is C₁-C₃ alkoxy, heterocyclyl, OR⁶, OPO₃H₂, CO₂H, OH, NH₂, —C(O)R⁶, —C(O)N(R¹⁸)₂, or —C(O)N(R⁶)₂; wherein:
    R¹⁶ is H or C₁-C₃ alkyl;
    R¹⁷ is C₁-C₃ alkyl, optionally substituted aryl or optionally substituted heteroaryl; and
    q is 0, 1, or 2.

In some embodiments, R³ is —C(O)R¹⁷, —OPO₃H₂ or -A-B—C wherein:
  A is —C(O)—, —C(O)O—, CH₂, or —C(O)NR⁶—;
  B is —CHR¹⁶— or —(CH₂)$_q$—; and
  C is heterocyclyl, OR⁶, OPO₃H₂, CO₂H, OH, NH₂, —C(O)R⁶, —C(O)N(R¹⁸)₂, or —C(O)N(R⁶)₂; wherein:
    R¹⁶ is H or C₁-C₃ alkyl;
    R¹⁷ is C₁-C₃ alkyl, optionally substituted aryl or optionally substituted heteroaryl; and
    q is 0, 1, or 2.

In some embodiments, R² and/or R³ is —C(O)—CHR¹⁹—N(R⁶)₂, wherein each R¹⁹ and R⁶ are independently selected and R¹⁹ is the side group of an amino acid or its enantiomer, for example, methyl (in the case of alanine), isopropyl, (in the case of valine), etc. Exemplary amino acids whose side groups may be employed include, arginine, histidine, lysine, aspartic acid, glutamic acid, serine, threonine, asparagine, glutamine, cysteine, glycine, proline, alanine, valine, isoleucine, leucine, methionine, phenylalanine, tyrosine, and tryptophan. In some embodiments, the amino acid is alanine, valine or glycine. In some embodiments, only one of R² and R³ is —C(O)—CHR¹⁹—N(R⁶)₂ while the other one of R² and R³ is H. In some embodiments R¹⁹ is not H.

In some embodiments, R⁸ is the side group of an amino acid or its enantiomer, for example, methyl (in the case of alanine), isopropyl, (in the case of valine), etc. Exemplary amino acids whose side groups may be employed include, arginine, histidine, lysine, aspartic acid, glutamic acid, serine, threonine, asparagine, glutamine, cysteine, glycine, proline, alanine, valine, isoleucine, leucine, methionine, phenylalanine, tyrosine, and tryptophan. In some embodiments, the amino acid is alanine, valine or glycine. In some embodiments R⁸ is not H.

"Amino acid" may refer to a D-isomer amino acid or an L-isomer amino acid. In certain embodiments, an amino acid may be a naturally occurring amino acid. Yet, in some embodiments, an amino acid may be an artificial amino acid. Specific side groups of the above named amino acids include —CH₃ (alanine), —(CH₂)₃HCNH₂NH (arginine), —CH₂CONH₂ (asparagine), —CH₂COOH (aspartic acid,), —CH₂SH (cysteine), —(CH₂)₂CONH₂ (glutamine), —(CH₂)₂COOH (glutamic acid), —H (glycine), —CHCH₃CH₂CH₃ (isoleucine), —CH₂CH(CH₃)₂ (leucine), —(CH₂)₄NH₂ (lysine), —(CH₂)₂SCH₃ (methionine), —CH₂Ph (phenylalanine), —CH₂OH (serine), —CHOHCH₃ (threonine), —CH(CH₃)₂ (valine),

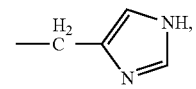
(histidine)

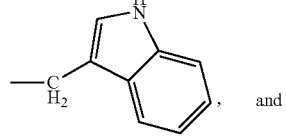
(tryptophan)

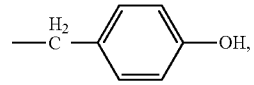
(tyrosine)

—(CH₂)₃NHCONH₂ (citrulline) or —(CH₂)₃NH₂ (ornithine). Ph designates a phenyl group.

In some embodiments, R² is an A-B—C moiety wherein:
  A and B are each CH₂; and
  C is CO₂H, amino, C(O)N(R¹⁸)₂, or —C(O)N(R⁶)₂.

In some embodiments, R³ is an A-B—C moiety wherein:
  A and B are each CH₂; and
  C is CO₂H, amino, C(O)N(R¹⁸)₂, or —C(O)N(R⁶)₂.

In some embodiments, R² is an A-B—C moiety of formula —C(O)—C wherein: C is optionally substituted aryl, or optionally substituted heteroaryl. In some embodiments, C is optionally substituted phenyl, optionally substituted piperidinyl, optionally substituted morpholino, optionally substituted azepanyl, optionally substituted aziridinyl, optionally substituted azetidinyl, optionally substituted pyrrolidinyl, or optionally substituted piperazinyl. In some embodiments, C is phenyl, piperidinyl, morpholino, azepanyl, aziridinyl, azetidinyl, pyrrolidinyl, or piperazinyl.

In some embodiments, R³ is an A-B—C moiety of formula —C(O)—C wherein: C is optionally substituted aryl, or optionally substituted heteroaryl. In some embodiments, C is optionally substituted phenyl, optionally substituted piperidinyl, optionally substituted morpholino, optionally substituted azepanyl, optionally substituted aziridinyl, optionally substituted azetidinyl, optionally substituted pyrrolidinyl, or optionally substituted piperazinyl. In some embodiments, C is phenyl, piperidinyl, morpholino, azepanyl, aziridinyl, azetidinyl, pyrrolidinyl, or piperazinyl.

In some embodiments, R² is an A-B—C moiety of formula —C(O)—CHCH₃—C wherein C is optionally substituted aryl or optionally substituted heteroaryl. In some embodiments, C is optionally substituted phenyl or optionally substituted napthyl. In some embodiments, C is phenyl optionally substituted with C₁-C₄ alkyl or napthyl optionally substituted with methoxy.

In some embodiments, R³ is an A-B—C moiety of formula —C(O)—CHCH₃—C wherein C is optionally substituted aryl or optionally substituted heteroaryl. In some embodiments, C is optionally substituted phenyl or optionally substituted napthyl. In some embodiments, C is phenyl optionally substituted with C₁-C₄ alkyl or napthyl optionally substituted with methoxy.

In some embodiments, R² is —C(O)—X—CH₂CO₂H, wherein X is O or NR¹. In some embodiments, R³ is —C(O)—X—CH₂CO₂H, wherein X is O or NR¹. In some embodiments, $R^2$ is —C(O)—(OCH$_2$CH$_2$)$_q$—OR$^6$, wherein $R^6$ is a C$_1$-C$_6$ alkyl. In some embodiments $R^6$ is a methyl. In some embodiments, q is 1.

In some embodiments, $R^3$ is —C(O)—X—CH$_2$CO$_2$H, wherein X is O or NR$^1$. In some embodiments, $R^3$ is —C(O)—X—CH$_2$CO$_2$H, wherein X is O or NR$^1$. In some embodiments, $R^3$ is —C(O)—(OCH$_2$CH$_2$)$_q$—OR$^6$, wherein $R^6$ is a C$_1$-C$_6$ alkyl. In some embodiments $R^6$ is a methyl. In some embodiments, q is 1.

In some embodiments, $R^2$ is —C(O)—(CH$_2$)$_2$CO$_2$H or —C(O)—(CHCH$_3$)—C, wherein C is optionally substituted aryl or optionally substituted heteroaryl. In some embodiments, $R^3$ is —C(O)—(CH$_2$)$_2$CO$_2$H or C(O)—(CHCH$_3$)—C, wherein C is optionally substituted aryl or optionally substituted heteroaryl. In some embodiments, the optionally substituted aryl is phenyl or napthyl. In some embodiments, the optionally substituted phenyl or napthyl is substituted with C$_1$-C$_6$ alkyl or C$_1$-C$_6$ alkoxy. In some embodiments, the optionally substituted phenyl or napthyl is substituted with methoxy.

In some embodiments, X is OH, and $R^2$ and $R^3$ form together a carbonyl containing group or a phosphorous containing group. In some embodiments, $R^2$ and $R^3$ are joined together to form —C(O)—, —SO$_2$—,

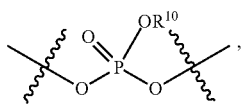

in an 8-12 membered heterocyclyl. In some embodiments, the compound is of formula:

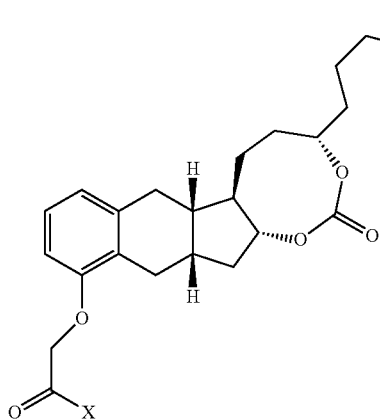

or

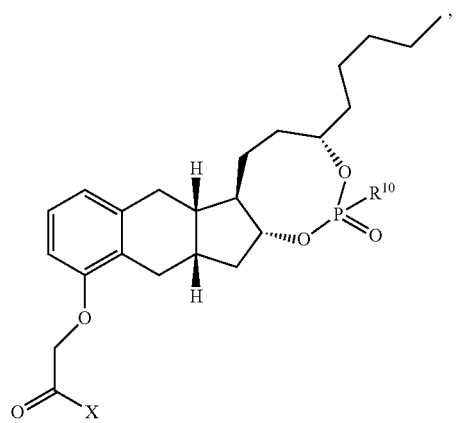

or a pharmaceutically acceptable salt thereof.

In another aspect, a compound of one of the following formulas is provided:

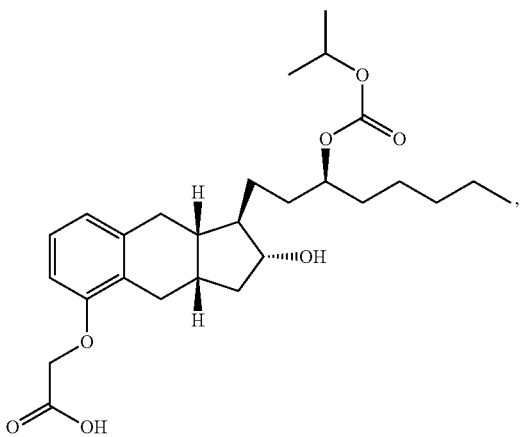

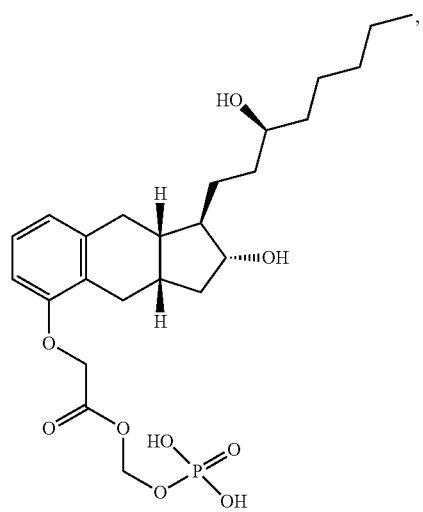

27
-continued
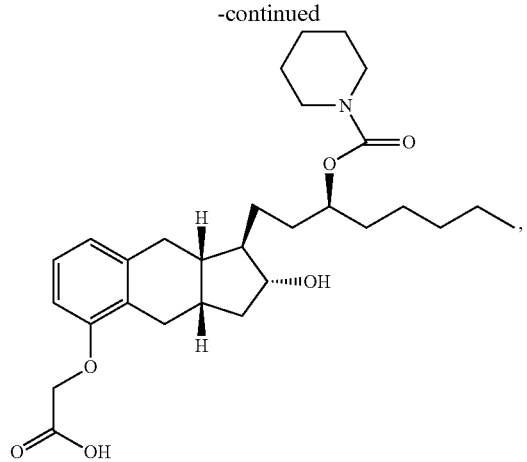
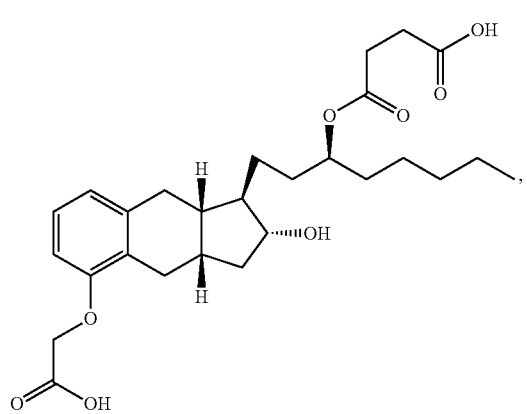
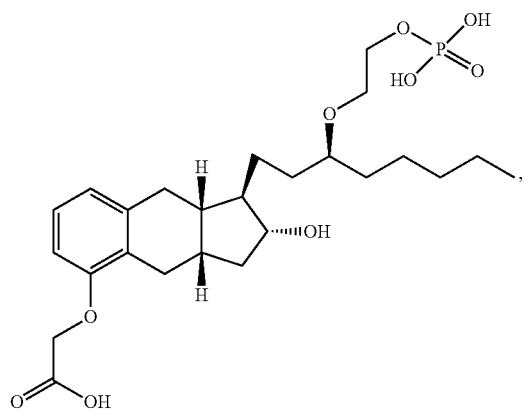
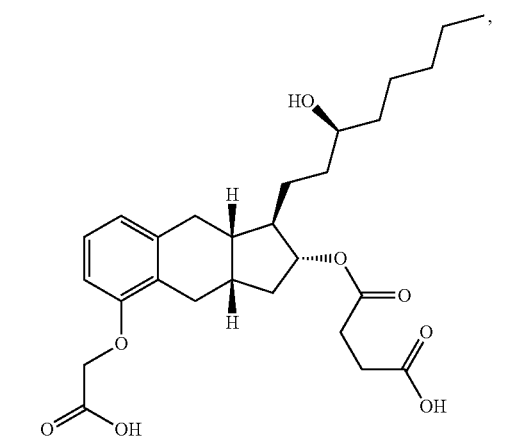
28
-continued
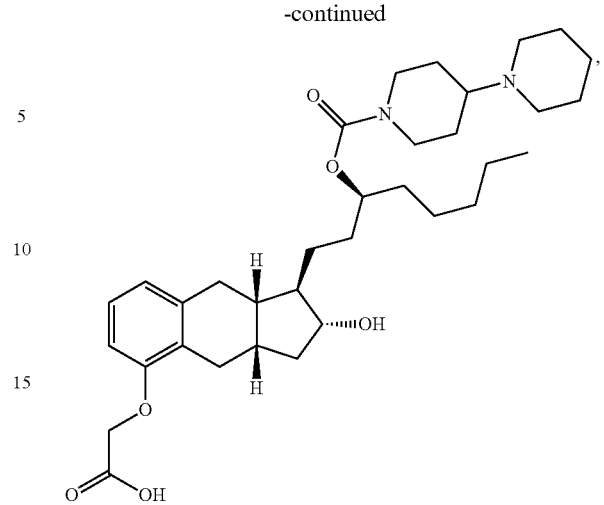
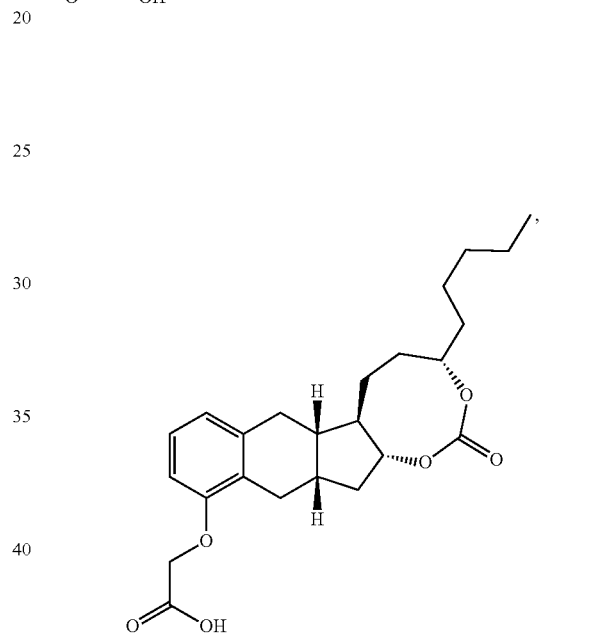
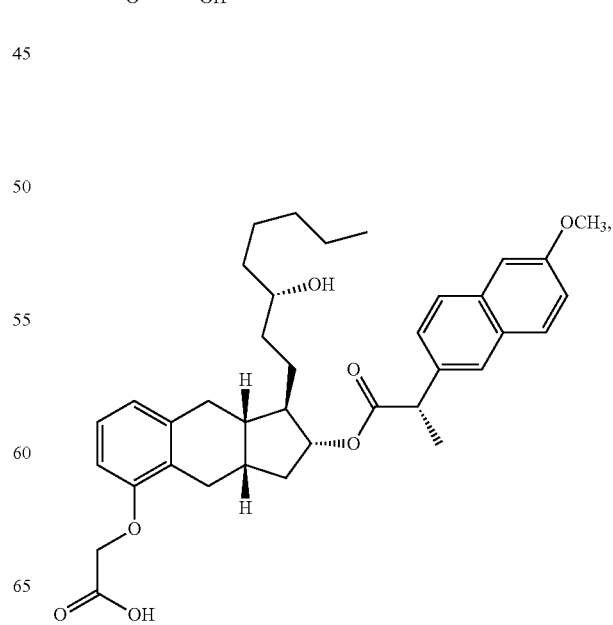

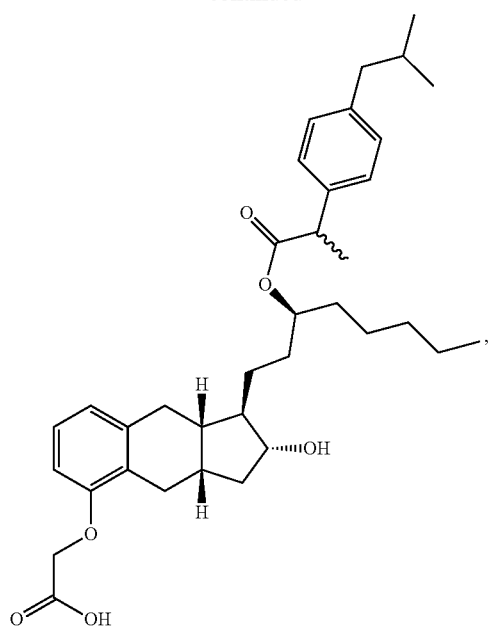
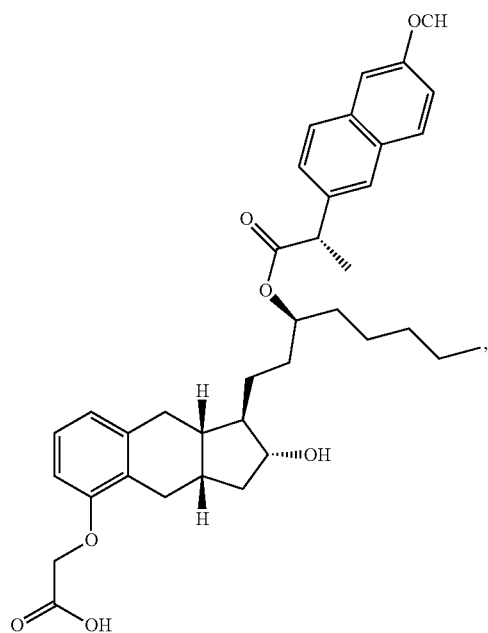
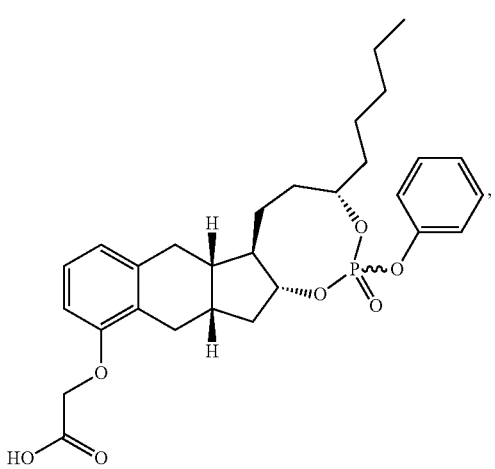
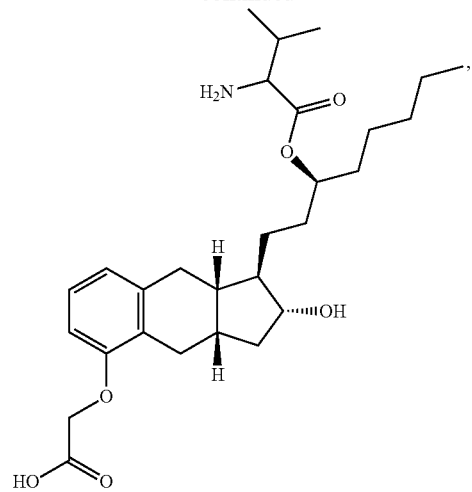
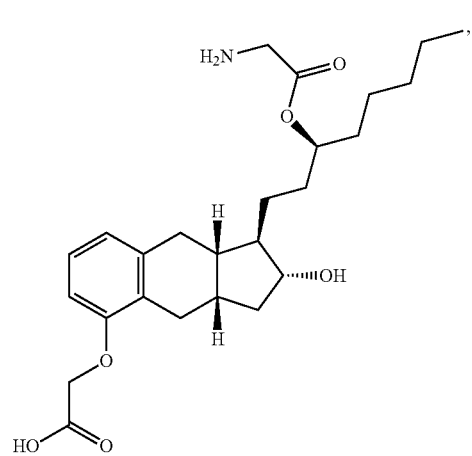
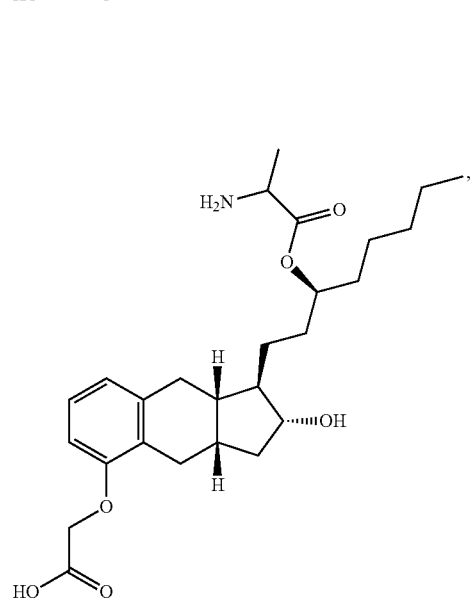

31
-continued
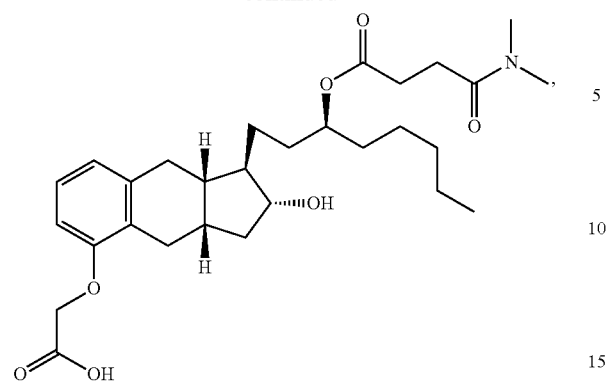
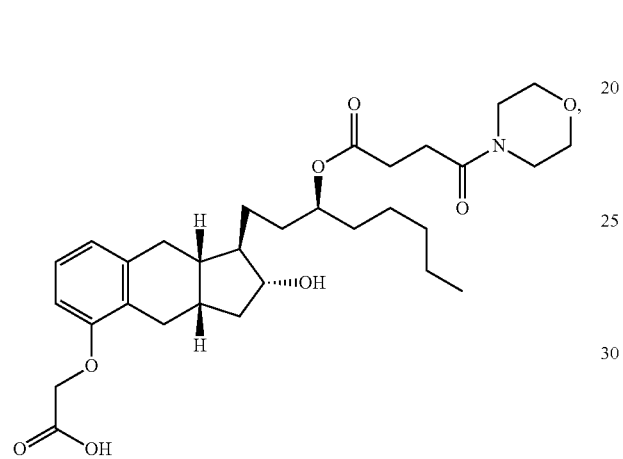
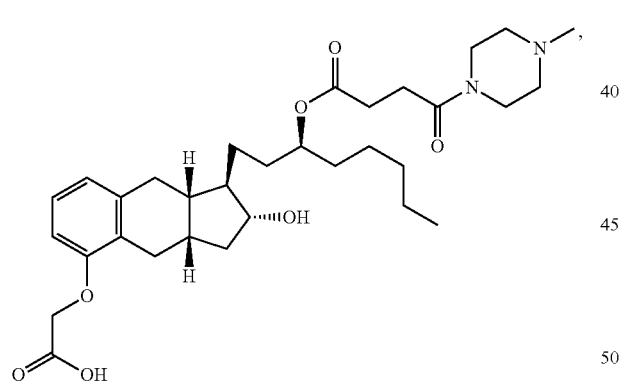
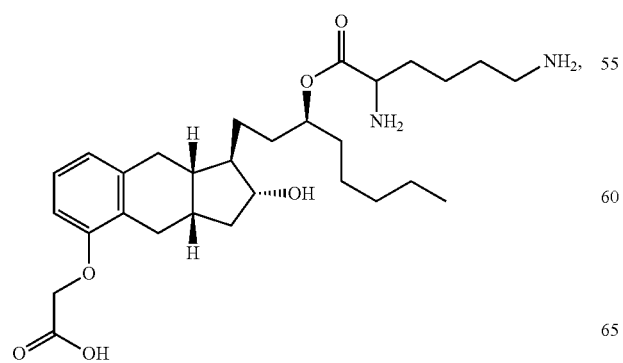
32
-continued
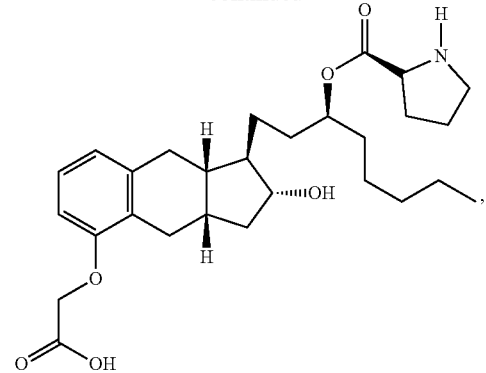
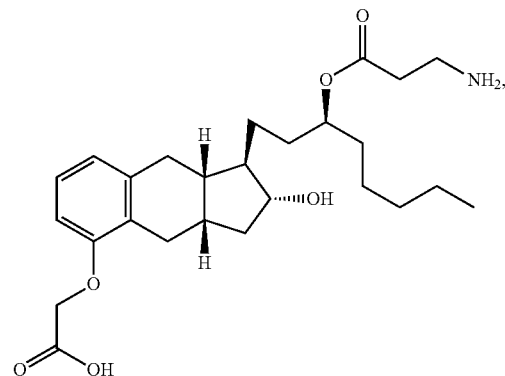
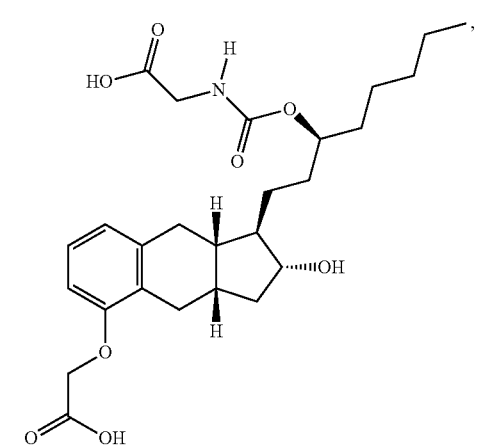
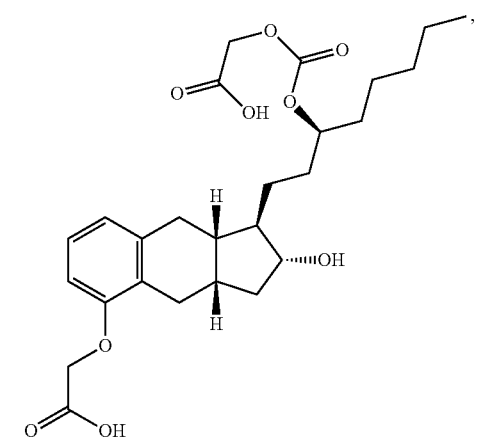

33
-continued
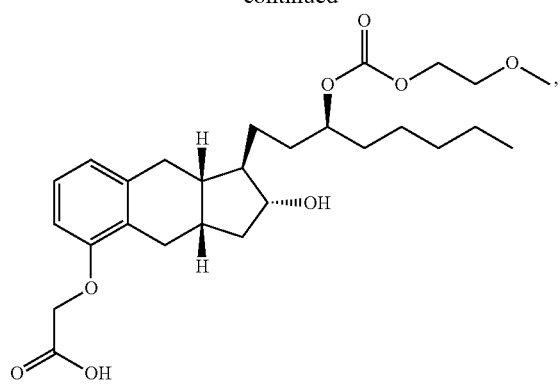
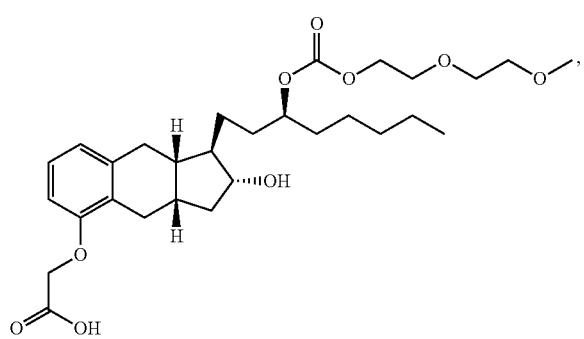
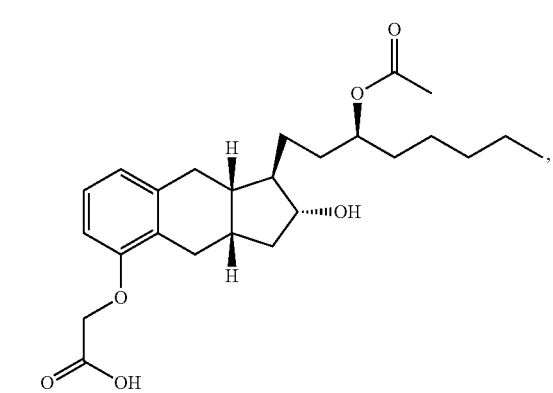
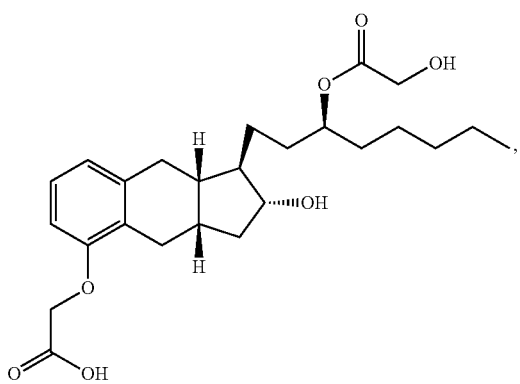
34
-continued
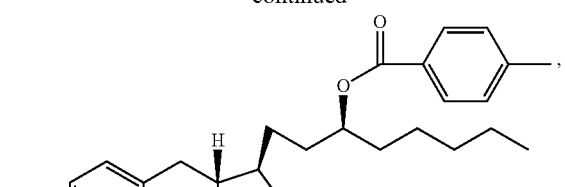
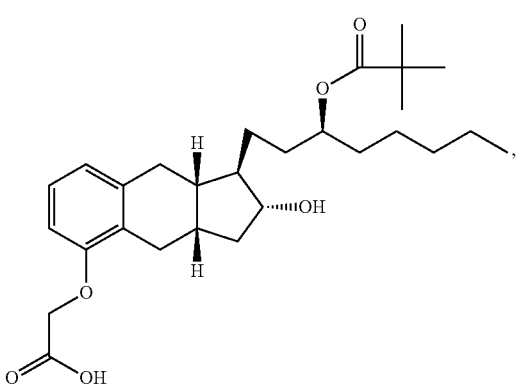
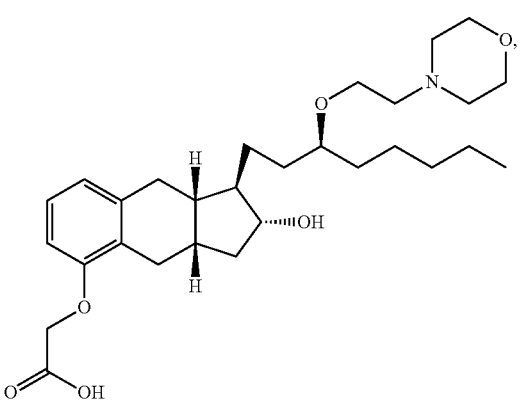
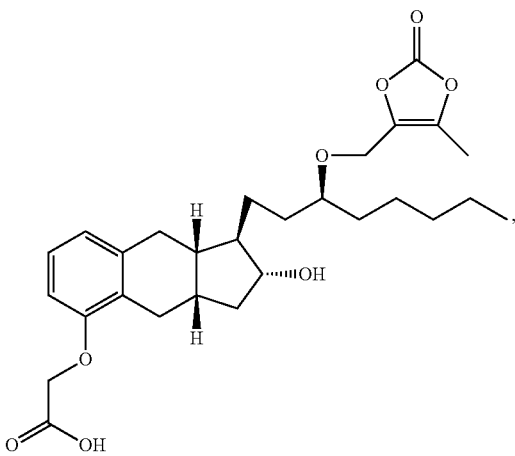

35
-continued
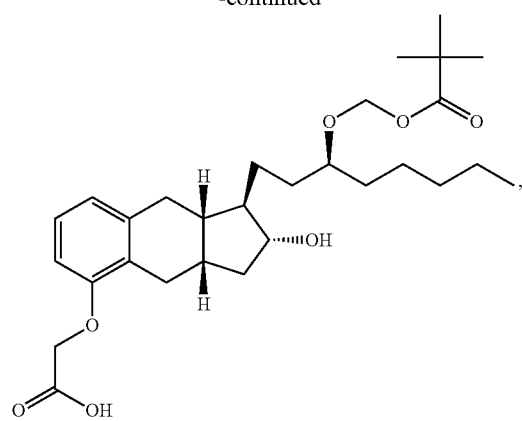
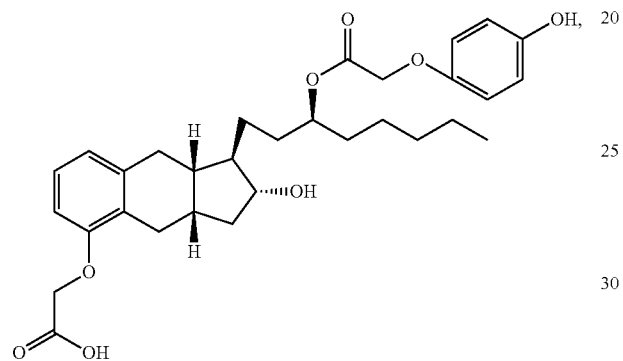
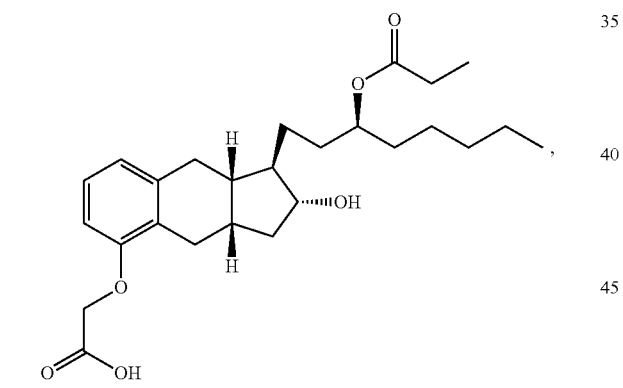
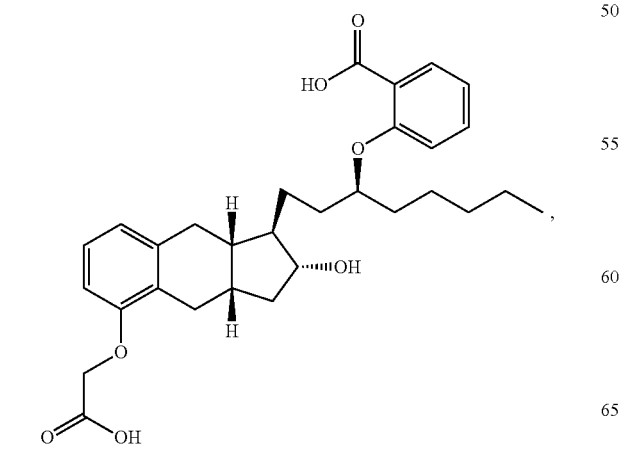
36
-continued
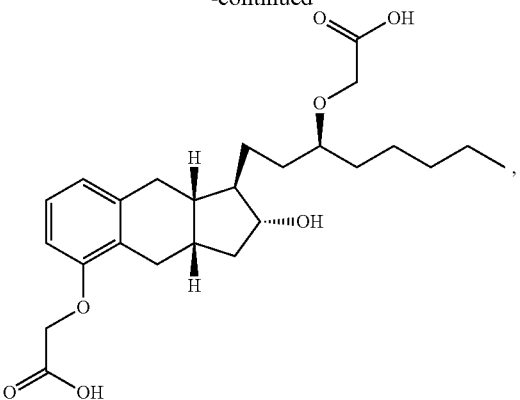
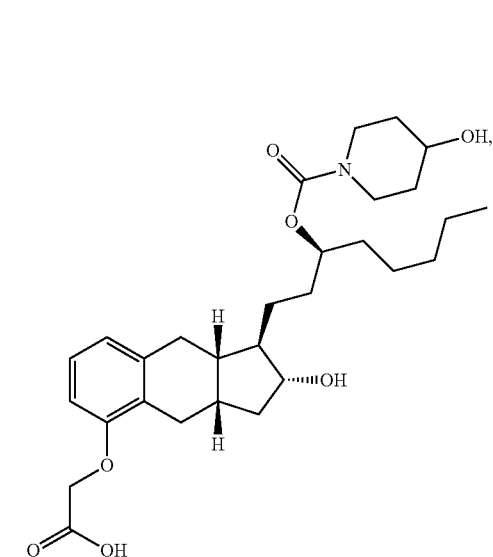
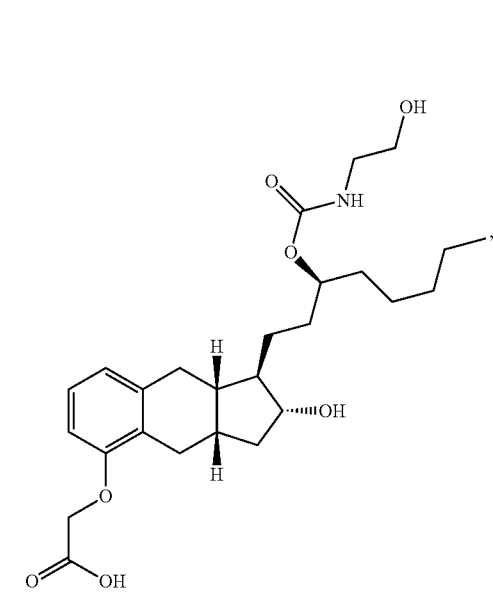

37
-continued
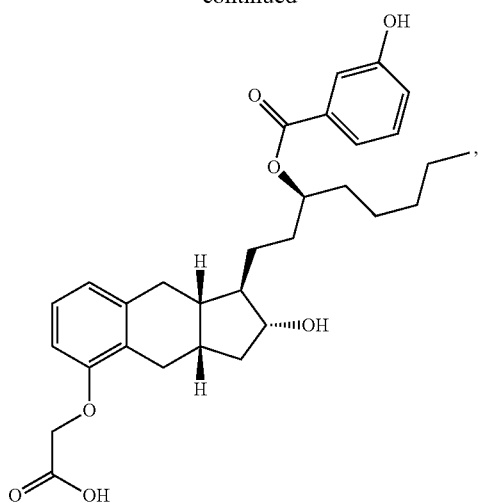
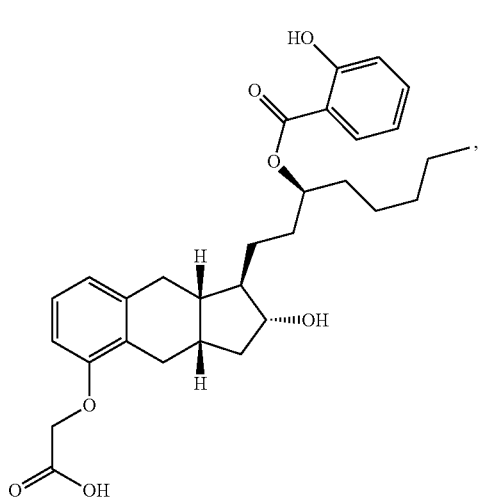
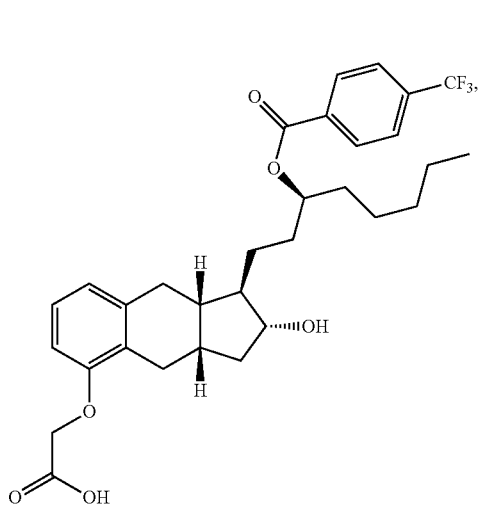
38
-continued
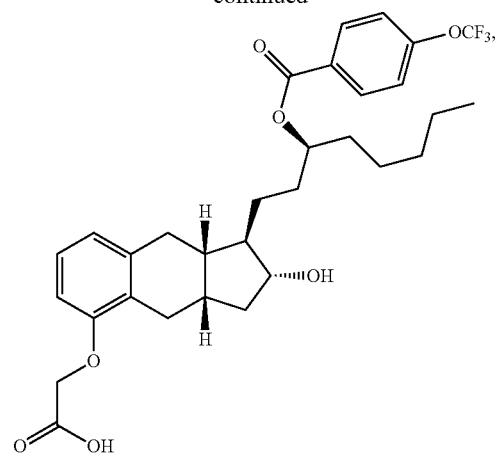
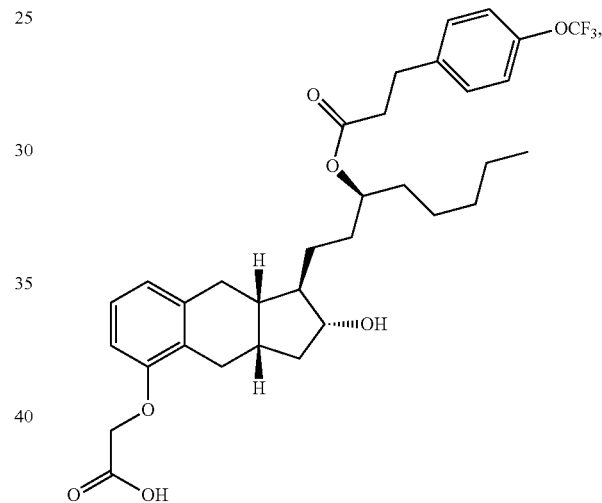
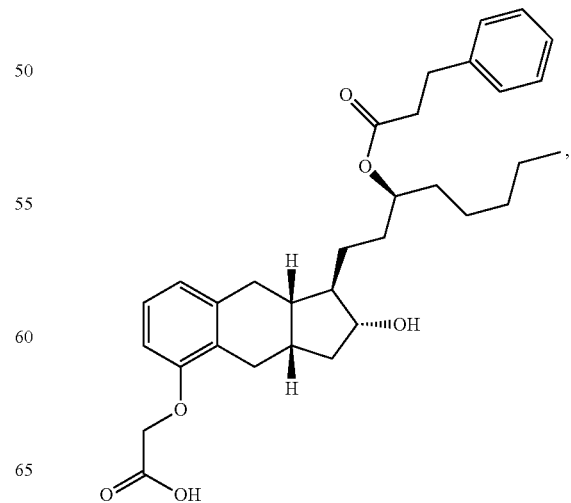

39
-continued
40
-continued
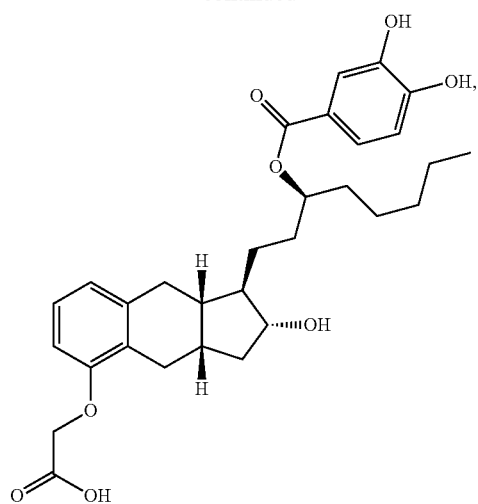
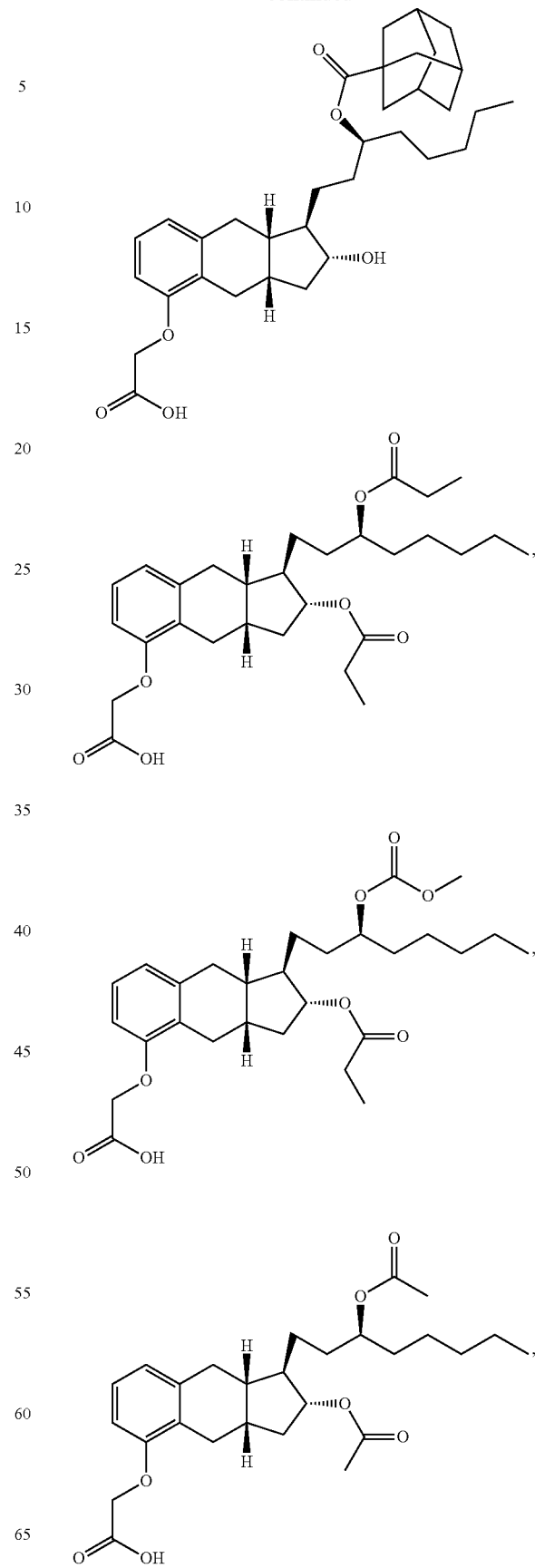

-continued

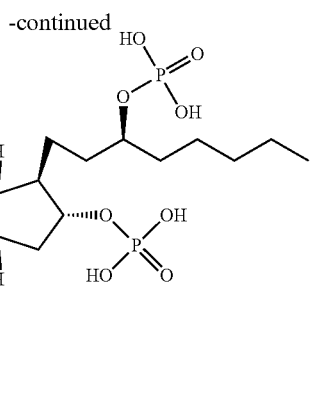

or a pharmaceutically acceptable salt thereof.

In some embodiments, the prodrug may be a disubstituted prodrug, i.e. a prodrug such that both $R^2$ and $R^3$ are not H. For example, $R^2$ and $R^3$ may be independently selected from a phosphorous containing group, $C(O)R^6$ or an A-B—C substituent as discussed above. In some embodiments, $R^2$ and $R^3$ may be independently selected from a phosphorous containing group, such as phosphate, and $C(O)R^6$. For example, in some embodiments, $R^2$ and $R^3$ may be independently selected from a phosphorous containing group, such as phosphate. Yet in some embodiments, In some embodiments, $R^2$ and $R^3$ may be independently selected from $C(O)R^6$.

In some embodiments, in a disubstituted prodrug, X may be OH.

In some embodiments, in the disubstituted prodrugs, $R^2$ and $R^3$ may be different. Yet in some embodiments, $R^2$ and $R^3$ may be the same. Examples of such prodrugs are prodrugs LXX, LXXI, LXXII and LXXIII.

In some embodiments, these prodrugs may have one or more advantages compared to treprostinil in addition to or alternative to reduction in site pain compared to administration of treprostinil or a salt thereof. For example, some of these prodrugs may have improved stability or greater tolerance in at least some patient populations.

In some embodiments, at least some of these prodrugs may have half-life in plasma, such as human plasma, rat plasma or dog plasma, of less than 150 minutes or less than 120 minutes or less than 90 minutes or less than 60 minutes or less than 50 minutes or less than 45 minutes or less than 40 minutes or less than 30 minutes or less than 20 minutes or less than 15 minutes or less than 12 minutes or about 10 minutes.

In some embodiments, at least some of these prodrugs may be stable, i.e remains intact or essentially intact, in plasma, such as human plasma, rat plasma or dog plasma, greater than 100 minutes or greater 120 minutes or greater than 150 minutes. For example, in some embodiments, at least some of these prodrugs may remain stable in plasma, such as human plasma, rat plasma or dog plasma, from 120 minutes to 240 minutes or 120 minutes to 180 minutes or 120 minutes to 150 minutes. Stability of a prodrug in plasma, such as human plasma, rat plasma or dog plasma, may be evaluated as described in the examples below. The stability of a prodrug in plasma may allow for the prodrug to reach a liver and/or to get in contact in liver microsomes and/or hepatocytes in In some embodiments, at least some of these prodrugs may be such that they remain intact or essentially intact they reach a liver of a subject upon administering. For example, when a prodrug is administered parenterally, such as via an injection, which may be for example, an intravenous or subcutaneous injection, the prodrug may remain intact or essentially intact in plasma of the subject before the prodrug reaches the liver of the subject and/or gets in contact with liver microsomes and/or hepatocytes. When a prodrug is administered orally, the prodrug may remain intact or essentially intact in fluids of a gastro-intestinal tract, such as a gastric fluid and/or intestinal fluid, of the subject before the prodrug reaches the liver of the subject and/or gets in contact with liver microsomes and/or hepatocytes. In certain embodiments, at least 90% or at least 92% or at least 94% or at least 95% or at least 96% or at least 97% or at least 98% or at least 99% of a prodrug remains intact, i.e. does not convert to treprostinil, before the prodrug reaches the liver of the subject and/or gets in contact with liver microsomes and/or hepatocytes.

In some embodiments, at least some of these prodrugs may have a half-time in liver, such as human liver, rat liver or dog liver, less than 30 minutes or less 20 minutes or greater than 15 minutes or less than 10 minutes or less than 9 minutes or less than 8 minutes or less than 7 minutes or less than 6 minutes or less than 5 minutes or less than 4 minutes or less than 3 minutes or any values or subranges within these ranges. A half-time in liver refer to a stability time of a prodrug in hepatocytes and/or liver microsomes and can be evaluated as described in the examples below. Preferably, a prodrug is such that it essentially completely converts into treprostinil when in the liver of the subject. For example, at least 99% of the prodrug or at least 99.2% or at least 99.4% or at least 99.5% or at least 99.6% or at least 99.7% or at least 99.8% or at least 99.9% may convert to treprostinil in the liver of the subject.

In some embodiments, at least some of these prodrugs may remain stable, which may mean remains intact or essentially intact, in a gastric fluid and/or an intestinal fluid, such as that of human, rat or dog, greater than 100 minutes or greater 120 minutes or greater than 150 minutes. For example, in some embodiments, at least some of these prodrugs remain stable in a gastric fluid and/or an intestinal fluid, such as that of human, rat or dog, from 120 minutes to 240 minutes or 120 minutes to 180 minutes or 120 minutes to 150 minutes. Prodrugs with longer stability time in gastric fluid and/or intestinal fluid may be particularly useful for oral administration. A stability time of a prodrug in a gastric fluid and/or an intestinal fluid can be evaluated as described in the examples below.

In some embodiments, at least some of these prodrugs may be such so that at least 85% or at least 88% or at least 90% or at least 91% or at least 92% or at least 93% or at least 94% or at least 95% or at least 96% or at least 97% or at least 98% or at least 99% of the prodrug remains intact, i.e. does not convert to treprostinil, after 120 minutes exposure to a skin homogenate. Such prodrugs may be particularly useful for parenteral administration, including administration by injection, such as subcutaneous injection, including continuous subcutaneous injection.

In some embodiments, at least some of these prodrugs may have plasma half times upon oral administration of at least 3 hours or at least 3.5 hours or at least 4 hours or at least 4.5 hours or at least 5 hours or at least 6 hours or at least 7 hours or at least 8 hours or at least 9 hours or at least 10 hours or at least 11 hours or at least 12 hours or at least 13 hours or at least 14 hours or at least 15 hours or at least 16 hours or at least 17 hours or at least 18 hours or at least 19 hours or at least 20 hours or at least 21 hours or at least 22 hours or at least 23 hours or at least 24 hours.

In some embodiments, at least some of these prodrugs may be such that its $EC_{50}$ value for at least one or at least two or at least three of IP, EP1, EP2 and DP1 receptors is at least 50 times or at least 100 times or at least 150 times or at least 200 times greater than that of treprotstinil. For example, in some embodiments, at least some of these prodrugs may be such that its EC50 value for IP receptor is at least 50 times or at least 100 times or at least 150 times or at least 200 times greater than that of treprostinil. In some embodiments, at least some of these prodrugs may be such that its EC50 values for each IP, EP1, EP2 and DP1 receptors is at least 50 times or at least 100 times or at least 150 times or at least 200 times greater than that of treprostinil. In some embodiments, at least some of these prodrugs may be such that its EC50 values for at least one or at least two or at least three or at least four of IP, EP1, EP2 and DP1 receptors is so large that it is undetectable, which may indicate a total inactivity against a particular receptor.

In some embodiments, at least some of these prodrugs may have oral bioavailability of at least 15% or at least 15% or at least 20% or at least 22% or at least 24% or at least 30% or at least 35% or at least 40% or at least 45% or at least 50% or at least 55% or at least 60% or at least 65% or at least 70% or at least 75% or at least 80%.

In some embodiments, at least for some prodrugs, $C_{max}$ and $AUC_{0-24\ hrs}$ upon oral administration may increase in a dose proportional manner.

In some embodiments, the prodrug may be such that it does not convert to treprostinil before being administered to a subject, such as a human being. For example, the prodrug may be such that it does not convert to treprostinil during its storage. Furthermore, the prodrug may be such that it does not convert into treprostinil in a pharmaceutical formulation, such as an injection formulation, e.g. a subcutaneous formulation, prior to administering the formulation to the subject. The prodrug may be such that it does not convert to treprostinil when it contacts a subcutaneous tissue of the subject upon an injection, such as a subcutaneous injection, of a pharmaceutical formulation comprising the prodrug to the subject. The prodrug may be such that it converts to treprostinil only when it reaches blood and/or liver of the subject. For example, a prodrug formulation, such as a subcutaneous prodrug formulation, may contain essentially no treprostinil per se prior to administering. In other words, a concentration of treprostinil per se in a prodrug formulation, such as a parenteral prodrug formulation, which may be a subcutaneous prodrug formulation, prior to administering may be less than 0.5% or less than 0.3% or less than 0.2% or less than 0.1% or less than 0.05% or less than 0.03% or less than 0.02% or less than 0.01% or less than 0.005% or less than 0.003% or less than 0.002% or less than 0.001%. Preferably, a concentration of treprostinil per se in a prodrug formulation, such as a parenteral prodrug formulation, which may be a subcutaneous prodrug formulation, prior to administering is undetectable by High Performance Liquid Chromatography (HPLC).

In some embodiments, the prodrug may be such that it does not convert to treprostinil when stored at pH ranging from 5 to 9 or 5.5 to 8.5 or from 6 to 8 for at least 1 week or at least 2 weeks or at least 3 weeks or at least 4 weeks at a temperature from 30 C to 45 C or from 35 C to 45 C or 37 C to 43 C or about 40 C. For example, a prodrug formulation, such as a subcutaneous prodrug formulation, may contain essentially no treprostinil per se after said storage. In other words, a concentration of treprostinil per se in a prodrug formulation, such as a parenteral prodrug formulation, which may be a subcutaneous prodrug formulation, after the storage may be less than 0.5% or less than 0.3% or less than 0.2% or less than 0.1% or less than 0.05% or less than 0.03% or less than 0.02% or less than 0.01% or less than 0.005% or less than 0.003% or less than 0.002% or less than 0.001%. Preferably, a concentration of treprostinil per se in a prodrug formulation, such as a parenteral prodrug formulation, which may be a subcutaneous prodrug formulation, after the storage is undetectable by High Performance Liquid Chromatography (HPLC).

In some embodiments, the prodrug may be such that no prodrug may be detected in blood or plasma of the subject upon administering the prodrug to the subject, which may be, for example, oral administration or injection, such as, intravenous or subcutaneous injection. For example, a plasma concentration of the prodrug may be below 2 ng/ml or below 1 ng/ml or below 0.7 ng/ml or below 0.5 ng/ml or below 0.3 ng/ml or below 0.2 ng/ml or below 0.1 ng/ml at any time after administering the prodrug.

In certain embodiments, the prodrug may be such that a metabolic product of in vivo conversion of the prodrug consists essentially of treprostinil, which may mean that treprostinil constitutes at least 90% or at least 95% or at least 98% or at least 99% or at least 99.5% or at least 99.8% or at least 99.9% of the metabolic product. In certain embodiments, the prodrug may be such that no metabolic product of the in vivo conversion of the prodrug, other than treprostinil, may be detected in blood or plasma of the subject. For example, a plasma concentration of non-treprostinil product(s) of the in vivo conversion of the prodrug may be below 2 ng/ml or below 1 ng/ml or below 0.7 ng/ml or below 0.5 ng/ml or below 0.3 ng/ml or below 0.2 ng/ml or below 0.1 ng/ml at any time after administering the prodrug.

In some embodiments, the prodrug may be such that plasma concentration of treprostinil may be detectable at least 24 hours after orally administering the prodrug. For example, plasma concentration of treprostinil 24 hours after orally administering the prodrug may at 1 ng/ml or at least 1.5 ng/ml or at least 2 ng/ml or at least 3 ng/ml or at least 4 ng/ml or at least 5 ng/ml or at least 6 ng/ml or at least 7 ng/ml or at least 8 ng/ml or at least 9 ng/ml or at least 10 ng/ml.

In some embodiments, the prodrug may be such that plasma concentration of treprostinil may be detectable at least 24 hours after orally administering the prodrug. For example, plasma concentration of treprostinil 24 hours after orally administering the prodrug may at 1 ng/ml or at least 1.5 ng/ml or at least 2 ng/ml or at least 3 ng/ml or at least 4 ng/ml or at least 5 ng/ml or at least 6 ng/ml or at least 7 ng/ml or at least 8 ng/ml or at least 9 ng/ml or at least 10 ng/ml.

In some embodiments, the prodrug may be such that plasma concentration of treprostinil may be detectable at least 24 hours or at least 30 hours after parenterally administering the prodrug, such as subcutaneously administering the prodrug. For example, plasma concentration of treprostinil 24 hours or 30 hours after such administering the prodrug may at 1 ng/ml or at least 1.5 ng/ml or at least 2 ng/ml or at least 3 ng/ml or at least 4 ng/ml or at least 5 ng/ml or at least 6 ng/ml or at least 7 ng/ml or at least 8 ng/ml or at least 9 ng/ml or at least 10 ng/ml.

In certain embodiments, a prodrug of treprostinil may have equilibrium water solubility of at least 1 mg/ml, or at least 2 mg/ml or at least 3 mg/ml, or at least 4 mg/ml, or at least 5 mg/ml, or at least 6 mg/ml. In certain embodiments, a prodrug of treprostinil may have equilibrium water solubility from 3 to 40 mg/ml or from 3 to 35 mg/ml or from 5 to 15 mg/ml or any value or subrange within these ranges.

The solubility of the prodrug may be greater if pH is increased in a vehicle used in solubility measurement and/or if one or more salts are removed from the vehicle.

In certain embodiments, a prodrug may have equilibrium water solubility of at least 7 mg/ml, or at least 8 mg/ml, or at least 9 mg/ml, or at least 10 mg/ml, or at least 20 mg/ml, or at least 30 mg/ml, or at least 50 mg/ml, or at least 70 mg/ml, or at least 100 mg/ml, or at least 200 mg/ml, or at least 300 mg/ml. Higher solubility prodrugs may be preferred for oral administration.

In some embodiments, a prodrug may comprise a low water solubility prodrug having an equilibrium water solubility no more than 1 mg/ml or no more than 0.5 mg/ml or no more than 0.2 mg/ml or no more than 0.1 mg/ml or no more than 0.05 mg/ml or no more than 0.02 mg/ml or no more than 0.01 mg/ml or no more than 0.005 mg/ml or no more than 0.002 mg/ml or more than 0.001 mg/ml. In some embodiments, the low water solubility prodrug may be formulated by making a solid dispersion, such as an amorphous solid dispersion. Methods of making solid dispersions, such as amorphous solid dispersions, of low water solubility compounds are disclosed, for example, in Newman, Developing Solid Oral Dosage Forms (Second Edition), Pharmaceutical Theory and Practice, 2017, Pages 497-518 and Paudel et al, International Journal of Pharmaceutics 453 (2013) 253-284, each of which is incorporated herein by reference in its entirety. In some embodiments, the low water solubility prodrug may be used in a salt form, which may allow increasing of the water solubility.

Pharmaceutical Compositions

Treprostinil prodrugs may be provided in a form of a pharmaceutical composition, which may also comprise a pharmaceutically acceptable carrier, excipient, binder, diluent or the like. Such pharmaceutical composition may be manufactured by methods known in the art such as granulating, mixing, dissolving, encapsulating, lyophilizing, emulsifying or levigating processes, among others. The composition may be in the form of, for example, granules, powders, tablets, capsules, syrup, suppositories, injections, emulsions, elixirs, suspensions and solutions. The composition may be formulated for a number of different administration routes, such as, for oral administration, transmucosal administration, rectal administration, transdermal or subcutaneous administration, as well as intrathecal, intravenous, intramuscular, intraperitoneal, intranasal, intraocular or intraventricular injection. The treprostinil prodrug may be administered by any of the above routes, for example in a local rather than a systemic administration, including as an injection or as a sustained release formulation.

In one embodiment, the pharmaceutical composition can compromise a prodrug of treprostinil and a carrier, such as sterile water. In some embodiments, the prodrug of treprostinil is formulated for subcutaneous administration, and such formulation may or may not include m-cresol or another preservative.

The treprostinil prodrugs described herein can be used to treat pulmonary hypertension. In some embodiments, the treprostinil prodrugs can be used to treat PAH. In some embodiments, the treprostinil prodrugs can be used to treat one or more of WHO Groups 1-5 pulmonary hypertension. Likewise, the treprostinil prodrugs described herein can be used to treat any disease or condition for which treprostinil is indicated or useful. The treprostinil prodrugs can be administered as the sole therapeutic agent or in addition to other active agents, including treprostinil.

For oral, buccal, and sublingual administration, powders, suspensions, granules, tablets, pills, capsules, gelcaps, and caplets may be acceptable as solid dosage forms. These can be prepared, for example, by mixing one or more treprostinil prodrugs, or pharmaceutically acceptable salts thereof, with at least one additive or excipient such as a starch or other additive. Suitable additives or excipients may be sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms may contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers. Besides those representative dosage forms described above, pharmaceutically acceptable excipients and carriers are generally known to those skilled in the art and can be employed. Such excipients and carriers are described, for example, in "Remingtons Pharmaceutical Sciences" Mack Pub. Co., New Jersey (1991), which is incorporated herein by reference.

A treprostinil prodrug may be formulated in a formulation suitable for parenteral administration that may comprise sterile aqueous preparations of a treprostinil prodrug, or a pharmaceutically acceptable salt thereof, where the preparations may be isotonic with the blood of the intended recipient. These preparations may be administered by means of subcutaneous injection, although administration may also be effected intravenously or by means of intramuscular or intradermal injection. Such preparations may conveniently be prepared by admixing the compound with water or a glycine or citrate buffer and rendering the resulting solution sterile and isotonic with the blood. Injectable formulations may contain from 0.1 to 5% w/v based on weight of treprostinil in the prodrug and may be administered at a rate of 0.1 ml/min/kg. Alternatively, the prodrug may be administered at a rate of 0.625 to 50 ng/kg/min based on weight of treprostinil in the prodrug. Alternatively, the prodrug may be administered at a rate of 10 to 15 ng/kg/min based on weight of treprostinil in the prodrug.

In some embodiments, a concentration of a treprostinil prodrug in a formulation for parenteral administration, such as intravenous infusion or subcutaneous infusion (including continuous subcutaneous infusion), may be from 0.0005 to 30 mg/mL or from 0.0007 to 50 mg/mL or from 0.001 to 15 mg/mL or any value or subrange within these ranges. Exemplary concentrations may include 0.1 mg/mL, 1 mg/mL, 2.5 mg/mL, 5 mg/mL or 10 mg/mL.

In some embodiments, a formulation of a treprostinil prodrug for parenteral administration, such as intravenous infusion or subcutaneous infusion (including continuous subcutaneous infusion), may be prepared by admixing the prodrug with a vehicle, such as a buffer. In certain embodiments, the vehicle may be a phosphate containing vehicle, i.e. at least one phosphate salt, which may be for example, dibasic phosphate, such as sodium dibasic phosphate or potassium dibasic phosphate, or tribasic phosphate, such as sodium tribasic phosphate or potassium phosphate. In certain embodiments, the vehicle may also contain a halogen salt, such as a chloride salt, which may be, for example, sodium chloride or potassium chloride. The halogen salt, such as sodium chloride may be used to adjust tonicity of the vehicle. In certain embodiments, it may be preferred that a phosphate and a halogen salt have the same cation. For example, when a phosphate is sodium phosphate, such as sodium tribasic phosphate or sodium tribasic phosphate, a halogen salt may a sodium halogen salt such as sodium chloride. Similarly, when a phosphate is potassium phosphate, such as potassium tribasic phosphate or potassium tribasic phosphate, a halogen salt may a potassium halogen salt such as potassium chloride. A solvent in the vehicle may contain water. In certain embodiments, water may be the only solvent in the vehicle. Yet in certain embodiments, the vehicle may contain one or more additional solvent in addition to water. In some embodiments, an additional solvent may be a preservative, such as m-cresol.

Preferably, the vehicle is isotonic with blood of a patient, such as a human being. The term isotonic may mean that the osmolarity and ion concentrations of the vehicle match those of the patient, such as human being. Non-limiting example of vehicles include phosphate-buffered saline, which is a water-based salt solution containing disodium hydrogen phosphate, sodium chloride and, in some formulations, potassium chloride and potassium dihydrogen phosphate. Other examples may include a vehicle containing 20 mM disbasic sodium phosphate with 125 mM sodium chloride and a vehicle containing 15 mM sodium phosphate tribasic, 125 mM sodium chloride and 0.3% w/w m-cresol.

Methods of Treatment

In some embodiments, a method of treating a disease or condition is provided, the method comprising administering to a subject a compound (e.g. a prodrug) or composition disclosed herein. In some embodiments, the disease or condition is one or more selected from the group consisting of pulmonary hypertension, congestive heart failure, peripheral vascular disease, Raynaud's phenomenon, Scleroderma, renal insufficiency, peripheral neuropathy, digital ulcers, intermittent claudication, ischemic limb disease, peripheral ischemic lesions, pulmonary fibrosis and asthma. In some embodiments, the disease is pulmonary hypertension.

In some embodiments, the subject has detectable treprostinil plasma levels for at least 24 hours upon said administering. In some embodiments, the subject has detectable treprostinil plasma levels for at least 30 hours upon said administering. In some embodiments, the subject has detectable treprostinil plasma levels for at least 36 hours upon said administering. In some embodiments, the subject has detectable treprostinil plasma levels for at least 42 hours upon said administering. In some embodiments, the subject has detectable treprostinil plasma levels for at least 48 hours upon said administering.

Administration may be performed via a route described above, or, for example, orally, intravenously, intra-arterial, intramuscularly, intranasally, rectally, vaginally, or subcutaneously. In some embodiments, the composition is administered by an injection. In some embodiments, the administering is performed orally. In some embodiments, the administering is performed subcutaneously.

In some embodiments, said administering results in no or less pain at a site of the injection compared to administering treprostinil. Pain, or the reduction thereof, may be assessed by any medically recognized method known in the art, for example, numerical rating scale (NRS), visual analog scale (VAS, i.e. Wong-Baker Pain Scale), the FLACC scale, the CRIES Scale, the COMFORT Scale, the McGill Pain Scale, the Manoski Scale, or other categorical scales. In comparison to injection of treprostinil, the pain upon injection of the prodrug results in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% less pain, as measured by a medically recognized method.

The subject treated may be a human, canine, feline, aves, non-human primate, bovine, or equine. In some embodiments, the subject is a human. In some embodiments, the subject is a human uncooperative or fearful of injections, for example, a pediatric or demented geriatric subject.

In some embodiments, a method of treating a disease or condition is provided, the method comprising administering to a subject a prodrug of treprostinil, wherein upon said administering said prodrug converts to a metabolic product, which consists essentially of treprostinil. The prodrug may be any of the compounds disclosed herein. In some embodiments, the metabolic product consists of treprostinil.

Embodiments described herein are further illustrated by, though in no way limited to, the following working examples.

Example 1

1. Plasma Stability

1.1. Experimental Procedure

Studies were carried out in mixed-gender human plasma male Sprague-Dawley rat plasma, and male Beagle dog plasma. All plasma was obtained from Bioreclamation and collected on K2EDTA. Plasma was adjusted to pH 7.4 prior to initiating the experiments. DMSO stocks were first prepared for the test articles. Aliquots of the DMSO solutions were dosed into 1.5 mL of plasma, which had been pre-warmed to 37° C., at a final test article concentration of 1 µM. The vials were kept in a benchtop Thermomixer® for the duration of the experiment. Aliquots (200 µL) were taken at each time point (0, 15, 30, 60, and 120 minutes) and added to 96-well plates which had been pre-filled with 400 µL of acetonitrile (ACN). Samples were stored at 4° C. until the end of the experiment. After the final time point was sampled, the plate was mixed and then centrifuged at 3000 rpm for 10 minutes. Aliquots of the supernatant were removed, diluted 1:1 into distilled water containing internal standard, and analyzed by LC-MS/MS against calibration standards prepared in a matched matrix. All samples were analyzed for the dosed prodrugs as well as the drug, treprostinil. The test article concentration was compared to the concentration at time 0 to determine the percent of test article remaining at each time point. Half-lives were calculated using GraphPad software, fitting to a single-phase exponential decay equation.

1.2. Experimental Results

TABLE 1

Stability of Prodrugs in Plasma

| Test Article | Species | Percent Remaining | | | | | Half-Life[a] |
| --- | --- | --- | --- | --- | --- | --- | --- |
| | | 0 min | 15 min | 30 min | 60 min | 120 min | (min) |
| Prodrug LXX | Human | 100 | 92.4 | 102 | 93.3 | 103 | >120 |
| | Rat | 100 | 98.3 | 80.3 | 69.3 | 45.0 | 102 |
| | Dog | 100 | 103 | 116 | 97.4 | 91.4 | >120 |
| Prodrug LXXI | Human | 100 | 114 | 108 | 99.1 | 95.3 | >120 |
| | Rat | 100 | 0 | 0 | 0 | 0 | <15 |
| | Dog | 100 | 102 | 92.0 | 97.6 | 81.6 | >120 |
| Prodrug LXXII | Human | 100 | 106 | 106 | 102 | 86.5 | >120 |
| | Rat | 100 | 107 | 107 | 83.6 | 79.7 | >120 |
| | Dog | 100 | 96.7 | 102 | 107 | 82.9 | >120 |

[a]When the calculated half-life is longer than the duration of the experiment, the half-life is expressed as > the longest incubation time. Then, if the calculated half-life is <2x the duration of the experiment, the calculated half-life is listed in parentheses. Similarly, when the calculated half-life is < the first non-zero timepoint, the half-life is listed as <15, with the calculated half-life also listed in parentheses, if applicable

TABLE 2

Formation of Treprostinil in Plasma

| Test Article Dosed | Species | Concentration (µM) | | | | |
| --- | --- | --- | --- | --- | --- | --- |
| | | 0 min | 15 min | 30 min | 60 min | 120 min |
| Prodrug LXX | Human | 0 | 0 | 0 | 0 | 0 |
| | Rat | 0 | 0.00392 | 0.0101 | 0.0331 | 0.0768 |
| | Dog | 0 | 0 | 0 | 0 | 0 |
| Prodrug LXXI | Human | 0 | 0 | 0 | 0 | 0 |
| | Rat | 0 | 0.860 | 1.04 | 1.14 | 1.00 |
| | Dog | 0 | 0 | 0 | 0 | 0 |
| Prodrug LXXII | Human | 0 | 0 | 0 | 0 | 0 |
| | Rat | 0 | 0 | 0 | 0.00595 | 0.0151 |
| | Dog | 0 | 0 | 0 | 0 | 0 |
| Prodrug LXXIII | Human | 0 | 0 | 0 | 0 | 0 |
| | Rat | 0 | 0 | 0 | 0 | 0 |
| | Dog | 0 | 0 | 0 | 0 | 0 |

2. Stability in Liver Microsomes

2.1. Experimental Procedure

Mixed-gender human liver microsomes, male Sprague-Dawley rat liver microsomes, and male Beagle dog liver microsomes were purchased from XenoTech. The reaction mixture, minus NADPH, was prepared as described below. In duplicate, the test article was added into the reaction mixture at a final concentration of 1 µM. The control compound, testosterone, was run simultaneously with the test article in a separate reaction. An aliquot of the reaction mixture (without cofactor) was equilibrated in a shaking water bath at 37° C. for 5 minutes. The reaction was initiated by the addition of cofactor, and the mixture was incubated in a shaking water bath at 37° C. Aliquots (200 µL) were withdrawn at 0, 10, 20, 30, and 60 minutes. Test article samples were immediately combined with 400 µL of ice-cold acetonitrile (ACN) to terminate the reaction. Testosterone samples were immediately combined with 400 µL of ice-cold 50/50 ACN/H2O containing 0.1% formic acid and internal standard to terminate the reaction. The samples were then mixed and centrifuged to precipitate proteins. Aliquots of the supernatant were removed, diluted 1:1 into distilled water containing internal standard, and analyzed by LC-MS/MS against calibration standards prepared in a matched matrix. All samples were analyzed for the dosed prodrugs as well as the drug, treprostinil. The test article concentration was compared to the concentration at time 0 to determine the percent of test article remaining at each time point. Half-lives and clearance were calculated using GraphPad software, fitting to a single-phase exponential decay equation.

2.2 Reaction Composition

Liver Microsomes 0.5 mg/mL
NADPH (cofactor) 1 mM
Potassium Phosphate, pH 7.4 100 mM
Magnesium Chloride 5 mM
Test Article 1 µM

2.3. Experimental Results

TABLE 3

Stability of Prodrugs in Liver Microsomes

| Test Article | Species | \multicolumn{5}{c}{Percent Remaining (AVG, n = 2)} | Half-life[a] (min) | $CL_{int}^{b}$ (mL/min/mg protein) |
| --- | --- | --- | --- | --- | --- | --- | --- | --- |
|  |  | 0 min | 10 min | 20 min | 30 min | 60 min |  |  |
| Prodrug LXX | Human | 100* | <1.00 | <1.00 | <1.00 | <1.00 | <10 | >0.139 |
|  | Rat | 100 | 31.7 | 3.50 | 1.24 | <1.00 | <10(5.53) | >0.139(0.250) |
|  | Dog | —* | — | — | — | — | <10 | >0.139 |
| Prodrug LXXI | Human | 100 | 43.5 | 9.48 | 5.78 | 1.69 | <10(7.32) | >0.139(0.189) |
|  | Rat | 100* | 5.68 | <1.00 | <1.00 | <1.00 | <10(2.41) | >0.139(0.575) |
|  | Dog | 100* | 10.6 | <1.00 | <1.00 | <1.00 | <10(3.05) | >0.139(0.454) |
| Prodrug LXXII | Human | —* | — | — | — | — | <10 | >0.139 |
|  | Rat | 100 | 55.6 | 18.5 | 10.4 | 3.66 | <10(9.65) | >0.139(0.144) |
|  | Dog | —* | — | — | — | — | <10 | >0.139 |

[a] When the calculated half-life is longer than the duration of the experiment, the half-life is expressed as > the longest incubation time. Then, if the calculated half-life is <2x the duration of the experiment, the calculated half-life is listed in parentheses. Similarly, when the calculated half-life is < the first non-zero timepoint, the half-life is listed as <10, with the calculated half-life also listed in parentheses.
[b] Intrinsic clearance ($CL_{int}$) was calculated based on $CL_{int}$ = k/P, where k is the elimination rate constant and P is the protein concentration in the incubation.
*Little to no prodrug was present in the time zero sample. It is likely this test article underwent non-CYP mediated degradation during the 5 minute pre-incubation period. Stability results should be interpreted with caution for these experiments.

TABLE 4

Formation of Treprostinil in Liver Microsomes

| Test Article Dosed | Species | \multicolumn{5}{c}{Concentration (µM) (AVG, n = 2)} |
| --- | --- | --- | --- | --- | --- | --- |
|  |  | 0 min | 10 min | 20 min | 30 min | 60 min |
| Prodrug LXX | Human | 1.18 | 0.903 | 0.602 | 0.538 | 0.381 |
|  | Rat | 0.336 | 0.595 | 0.764 | 0.653 | 0.699 |
|  | Dog | 1.24 | 1.26 | 1.24 | 1.23 | 1.07 |
| Prodrug LXXI | Human | 0.0646 | 0.124 | 0.194 | 0.209 | 0.192 |
|  | Rat | 0.301 | 0.490 | 0.638 | 0.590 | 0.595 |
|  | Dog | 0.875 | 0.985 | 0.979 | 0.970 | 0.853 |
| Prodrug LXXII | Human | 0.989 | 0.829 | 0.543 | 0.485 | 0.349 |
|  | Rat | 0.0413 | 0.0950 | 0.182 | 0.190 | 0.216 |
|  | Dog | 1.07 | 1.07 | 1.04 | 1.05 | 0.897 |
| Prodrug LXXIII | Human | 0 | 0.00471 | 0.00629 | 0.00835 | 0.00762 |
|  | Rat | 0.00 | 0.00495 | 0.00898 | 0.0117 | 0.0171 |
|  | Dog | 0.00 | 0.00908 | 0.0186 | 0.0236 | 0.0294 |

TABLE 5

Half-life of Testosterone in Liver Microsomes

| Control Compound | Species | Half-life (min) | $CL_{int}$ (mL/min/mg protein) | Acceptable Range (t½, min) |
| --- | --- | --- | --- | --- |
| Testosterone | Human | 29.2 | 0.0475 | ≤40 |
|  | Rat | 1.71 | 0.809 | ≤15 |
|  | Dog | 37.7 | 0.0368 | ≤41 |

3. Stability in Hepatocytes

3.1. Experimental Procedure

Mixed-gender human cryopreserved hepatocytes, male Sprague-Dawley rat cryopreserved hepatocytes, and male Beagle dog cryopreserved hepatocytes were purchased from XenoTech. The hepatocytes were thawed and prepared according to the vendor's instructions, pooled into Krebs Henseleit buffer (KHB, pH 7.4), and kept on ice prior to the experiments. The hepatocyte suspension was equilibrated in a shaking water bath at 37° C. for 3 minutes, and then the reaction was initiated by spiking the test article (in duplicate) into the hepatocyte suspension ($1.5 \times 10^6$ cells/mL) at a final test article concentration of 1 µM. The final DMSO content in the incubation mixture was ≤0.1%. The reaction mixture was incubated in a shaking water bath at 37° C. Positive controls, testosterone (1 µM) and 7-hydroxycoumarin (7-HC) (100 µM), were performed in parallel to confirm the activity of the hepatocytes. Aliquots of the test article were withdrawn (n=1) at 0, 15, 30, 60, and 120 minutes. Aliquots of testosterone were withdrawn (n=1) at 0, 5, 15, 30, 60, and 120 minutes. Aliquots of 7-HC were withdrawn (n=1) at 0 and 15 minutes. The reaction was immediately terminated by adding two volumes of ice-cold acetonitrile (ACN) to the test article samples and three volumes of ACN containing internal standard to the positive control samples. The samples were then mixed and centrifuged to precipitate proteins. An aliquot of the supernatant was then diluted with water and analyzed by LC-MS/MS against calibration standards prepared in a matched matrix. Testosterone samples were analyzed without calibration standards. All test article samples were analyzed for the dosed prodrugs as well as the drug, treprostinil.. The test article concentration was compared to the concentration at time 0 to determine the percent of test article remaining at each time point. Half-lives and clearance values were calculated using GraphPad software, fitting to a single-phase exponential decay equation.

3.2. Experimental Results

TABLE 6

Stability of Prodrugs in Cryopreserved Hepatocytes

| Test Article | Species | Percent Remaining (AVG, n = 2) | | | | | Half-life[a] (min) | $CL_{int}$[b] (mL/min/mg protein) |
| --- | --- | --- | --- | --- | --- | --- | --- | --- |
| | | 0 min | 15 min | 30 min | 60 min | 120 min | | |
| Prodrug LXX | Human | 100 | 1.57 | <1.00 | <1.00 | <1.00 | <15(2.50) | >0.0308(0.185) |
| | Rat | 100 | 7.28 | <1.00 | <1.00 | <1.00 | <15(3.97) | >0.0308(0.116) |
| | Dog | 100 | <1.00 | <1.00 | <1.00 | <1.00 | <15 | >0.0308 |
| Prodrug LXXI | Human | 100 | 32.5 | 8.06 | <1.00 | <1.00 | <15(8.96) | >0.0308(0.0516) |
| | Rat | 100 | <1.00 | <1.00 | <1.00 | <1.00 | <15(1.56) | >0.0308(0.295) |
| | Dog | 100 | 1.50 | <1.00 | <1.00 | <1.00 | <15(2.47) | >0.0308(0.187) |
| Prodrug LXXII | Human | 100 | <1.00 | <1.00 | <1.00 | <1.00 | <15(1.67) | >0.0308(0.276) |
| | Rat | 100 | 21.3 | 3.42 | <1.00 | <1.00 | <15(6.63) | >0.0308(0.0697) |
| | Dog | 100 | <1.00 | <1.00 | <1.00 | <1.00 | <15 | >0.0308 |

[a]When the calculated half-life is longer than the duration of the experiment, the half-life is expressed as > the longest incubation time. Then, if the calculated half-life is <2x the duration of the experiment, the calculated half-life is listed in parentheses. Similarly, when the calculated half-life is < the first non-zero timepoint, the half-life is listed as <15, with the calculated half-life also listed in parentheses if applicable.
[b]Intrinsic clearance ($CL_{int}$) was calculated based on $CL_{int}$ = k/P, where k is the elimination rate constant and P is the cell concentration in the incubation.

TABLE 7

Formation of Treprostinil in Cryopreserved Hepatocytes

| Test Article Dosed | Species | Concentration (μM) (AVG, n = 2) | | | | |
| --- | --- | --- | --- | --- | --- | --- |
| | | 0 min | 15 min | 30 min | 60 min | 120 min |
| Prodrug LXX | Human | 0.00542 | 0.638 | 0.556 | 0.482 | 0.413 |
| | Rat | 0 | 0.606 | 0.579 | 0.484 | 0.405 |
| | Dog | 0.0959 | 0.736 | 0.597 | 0.511 | 0.445 |
| Prodrug LXXI | Human | 0 | 0.118 | 0.211 | 0.273 | 0.259 |
| | Rat | 0 | 0.422 | 0.403 | 0.347 | 0.292 |
| | Dog | 0.00293 | 0.501 | 0.408 | 0.348 | 0.303 |
| Prodrug LXXII | Human | 0.00458 | 0.562 | 0.491 | 0.433 | 0.364 |
| | Rat | 0 | 0.240 | 0.301 | 0.298 | 0.274 |
| | Dog | 0.0636 | 0.671 | 0.541 | 0.465 | 0.401 |
| Prodrug LXXIII | Human | 0 | 0.0163 | 0.0399 | 0.0848 | 0.158 |
| | Rat | 0 | 0.00970 | 0.0208 | 0.0431 | 0.0925 |
| | Dog | 0 | 0.0506 | 0.112 | 0.195 | 0.272 |

TABLE 8

Half-life of Testosterone in Cryopreserved Hepatocytes

| Species | Half-life (min) | Clint (mL/min/10⁶ cells) | Half-life Acceptance Criteria |
| --- | --- | --- | --- |
| Human | 4.82 | 0.0959 | ≤5.0 |
| Rat | 1.03 | 0.448 | ≤5.0 |
| Dog | 6.50 | 0.0711 | ≤10.0 |

TABLE 9

Rates of Formation of Glucuronide and Sulfate of 7-Hydroxycoumarin in Cryopreserved Hepatocytes

| Species | Analyte | Formation Rate (pmol/min/10⁶ cells) | Acceptable Range (pmol/min/10⁶ cells) |
| --- | --- | --- | --- |
| Human | 7-HC-G | 97.7 | ≥50 |
| | 7-HC-S | 10.8 | ≥1.0 |
| Rat | 7-HC-G | 91.4 | ≥25 |
| | 7-HC-S | 24.7 | ≥5.0 |
| Dog | 7-HC-G | 114 | ≥50 |
| | 7-HC-S | 35.9 | ≥5.0 |

7-HC-G: 7-hydroxycoumarin glucuronide;
7-HC-S: 7 hydroxycoumarin sulfate

6.4. Stability in Simulated Intestinal Fluid

6.4.1. Experimental Procedure

Studies were carried out in simulated intestinal fluid (SIF). SIF was prepared by dissolving 6.8 g of $KH_2PO_4$ in 250 mL of water, mixing, and then adding 77 mL of 0.2 N NaOH and 750 mL of water. Pancreatin (10 g) was added, mixed, and the pH was adjusted to pH 6.8 with 10 N NaOH. DMSO stocks were first prepared for the test articles. Aliquots of the DMSO solutions were dosed into 0.4 mL of matrix, which had been pre-warmed to 37° C., at a final test article concentration of 1 μM. The vials were kept in a benchtop Thermomixer® for the duration of the experiment. A separate tube was dosed for each time point in each matrix. At the appropriate times (0, 15, 30, 60, and 120 minutes), 0.8 mL of acetonitrile (ACN) containing 1% formic acid and internal standard was added directly to a single tube. Samples were mixed and then immediately stored at 4° C. until the end of the experiment. After the final time point was sampled, the plate was mixed and then centrifuged at 3000 rpm for 10 minutes. Aliquots of the supernatant were removed, diluted 1:1 into distilled water containing internal standard, and analyzed by LC-MS/MS against calibration standards prepared in a matched matrix. All samples were analyzed for the dosed prodrugs as well as the drug, treprostinil. The test article concentration was compared to the concentration at time 0 to determine the percent of test article remaining at each time point. Half-lives were calculated using GraphPad software, fitting to a single-phase exponential decay equation.

TABLE 10

Stability of Prodrugs in Simulated Intestinal Fluid

| Test Article | Matrix | Percent Remaining | | | | | Half-Life[a] |
| | | 0 min | 15 min | 30 min | 60 min | 120 min | (min) |
| --- | --- | --- | --- | --- | --- | --- | --- |
| Prodrug LXX | SIF | 100 | 97.2 | 104 | 93.6 | 86.2 | >120 |
| Prodrug LXXI | SIF | 100 | 96.2 | 100 | 91.9 | 83.5 | >120 |
| Prodrug LXXII | SIF | 100 | 111 | 107 | 108 | 109 | >120 |

[a]When the calculated half-life is longer than the duration of the experiment, the half-life is expressed as > the longest incubation time. Then, if the calculated half-life is <2x the duration of the experiment, the calculated half-life is listed in parentheses.

TABLE 11

Formation of Treprostinil in Simulated Fluid

| Test Article Dosed | Matrix | Concentration (µM) | | | | |
| | | 0 min | 15 min | 30 min | 60 min | 120 min |
| --- | --- | --- | --- | --- | --- | --- |
| Prodrug LXX | SIF | 0 | 0 | 0 | 0.00415 | 0.0720 |
| Prodrug LXXI | SIF | 0 | 0 | 0 | 0 | 0.0121 |
| Prodrug LXXII | SIF | 0 | 0 | 0 | 0 | 0.0126 |
| Prodrug LXXIII | SIF | 0 | 0 | 0 | 0 | 0 |

5. Stability in Human Subcutaneous Skin Homogenate

The objective of this study was to determine the stability of seven test articles in human subcutaneous skin homogenate.

5.1. Experimental Procedure

The stability of calcein-AM and test articles (Prodrugs IV, LXIV, LXVII, LXX, LXXI, LXXII and LXXIII) was assessed in subcutaneous skin homogenate (BioIVT, Lot information in Table 12). The pool of skin homogenate was prepared by combining equal volumes of three lots that were tested in the initial skin homogenate lot assessment experiments.

A stock solution of calcein-AM was first prepared at 5 mM in DMSO, followed by a serial dilution into methanol at a concentration of 100 µM. 495 µL of skin homogenate was thawed and warmed to 37° C. A 5 µL aliquot of the 100 µM calcein-AM solution was spiked into the skin homogenate, for a final calcein-AM dosing concentration of 1 µM. After briefly mixing, 150 µL aliquots were removed in triplicate and transferred to 96-well Falcon plates. The plates were placed onto a Thermomixer and maintained at 37° C., with gentle shaking for the duration of the experiment. At each time point (0, 15, 30, 60, and 120 minutes), the plate was removed from the Thermomixer and transferred to a FLUOstar® plate reader, and the formation of calcein (Sigma) was monitored by fluorescence (490/515 nm). Calibration standards of calcein were prepared in distilled water by serial dilutions of a calcein DMSO stock at final concentrations ranging from 1 µM to 1 nM. All samples and standards were read concurrently (Table 13).

For each of the test articles, 495 µL of skin homogenate was added to triplicate centrifuge tubes. To each tube, 5 µL of a 100 µM solution of test article was added, for a final test article dosing concentration of 1 µM. The tubes were placed onto a Thermomixer and maintained at 37° C. with gentle shaking for the duration of the experiment. At each time point (0, 30, 60, and 120 minutes), a 100 µL aliquot was removed from each tube and combined with 200 µL of acetonitrile to stop the stability reaction. The tubes were mixed and centrifuged at 3000 rpm for 10 minutes. Aliquots of supernatant were removed and diluted 1:1 with distilled water containing internal standard (2 µM treprostinil-d4). Calibration standards for the treprostinil analysis were prepared for each test article in a surrogate matrix (supernatant from a mixture of 1:2 human plasma:acetonitrile), at concentrations ranging from 1 µM to 1 nM. Calibration standards were also diluted 1:1 with distilled water containing internal standard. The disappearance of each individual test article was monitored, as well as the formation of treprostinil (Table 14 and Table 15).

TABLE 12

Skin Homogenate Lot Information

| Fraction | Gender | Age | Race |
| --- | --- | --- | --- |
| Subcutaneous | Female | 43 | Hispanic |
| Subcutaneous | Female | 31 | African American |
| Subcutaneous | Female | 37 | Caucasian |

5.2. Experimental Results

TABLE 13

Formation of Calcein in Pooled Human Skin Homogenate

| Test Article Dosed | Calcein Concentration (µM) (Avg, n = 3) | | | | |
| | 0 min | 15 min | 30 min | 60 min | 120 min |
| --- | --- | --- | --- | --- | --- |
| Calcein-AM | 0.00340 | 0.0243 | 0.0953 | 0.261 | 0.419 |

TABLE 14

Stability of Test Articles in Pooled Human Skin Homogenate

| Test Article | Percent Remaining (Avg, n = 3) | | | |
| | 0 min | 30 min | 60 min | 120 min |
| --- | --- | --- | --- | --- |
| Prodrug IV | 100 | 90.4 | 86.3 | 78.1 |
| Prodrug LXIV | 100 | 93.6 | 88.3 | 72.6 |
| Prodrug LXVII | 100 | 79.2 | 61.6 | 35.0 |
| Prodrug LXX | 100 | 99.4 | 105 | 96.3 |
| Prodrug LXXI | 100 | 97.1 | 92.5 | 90.8 |
| Prodrug LXXIII | 100 | 86.2 | 71.2 | 64.0 |

TABLE 15

Measured Concentration of Treprostinil in Pooled Human Skin Homogenate

| Test Article | Measured Concentration (μM) (Avg, n = 3) | | | |
|---|---|---|---|---|
| Dosed | 0 min | 30 min | 60 min | 120 min |
| Prodrug IV | 0 | 0.0395 | 0.0771 | 0.153 |
| Prodrug LXIV | 0 | 0.0793 | 0.155 | 0.283 |
| Prodrug LXVII | 0 | 0.224 | 0.408 | 0.657 |
| Prodrug LXX | 0 | 0.0179 | 0.0411 | 0.0972 |
| Prodrug LXXI | 0 | 0 | 0.00262 | 0.00643 |
| Prodrug LXXII | 0 | 0.0200 | 0.0556 | 0.147 |
| Prodrug LXXIII | 0 | 0.00817 | 0.0216 | 0.0509 |

6. An In Vitro Assessment of the Pharmacology of Disubstituted Treprostinil Prodrugs LXX-LXXIII

6.1. Summary of Findings

Comparing the disubstituted prodrugs to treprostinil:
(A) Prodrugs LXX, LXXI and LXXII are inactive, and Prodrug LXXIII is approximately 200-fold less active at the prostaglandin I2 (PGI2) receptor (IP);
(B) Prodrugs LXX, LXXI and LXXIII are inactive, and Prodrug LXXII exhibits a non-traditional dose response curve at the prostaglandin E2 (PGE2) receptor 2 (EP2);
(C) Each of Prodrugs LXX-LXXIII exhibits a non-traditional dose-response curve, with Prodrugs LXX, LXXII and LXXIII being several hundred-fold less active and Prodrug LXXI approximately 2000-fold less active at the prostaglandin D2 (PGD2) receptor 1 (DP1);
(D) Each of Prodrugs LXX-LXXIII is inactive at the PGE2 receptor 1 (EP1).

6.2. Materials

Cells and control agonists: Cells and control agonists used in the study are summarized in the table below.

TABLE 16

Cell Lines and Control Agonists Used in the Study

| Species | Target | Parental | Assays | Control agonist |
|---|---|---|---|---|
| Human | DP1 | HEK293T | cAMP | PGD2 |
| Human | EP2 | HEK293T | cAMP | Iloprost |
| Human | IP1 | CHO-K1 | cAMP | Iloprost |
| Human | EP1 | HEK293T | Calcium | Iloprost |

TABLE 17

Compounds

| # | Compound ID | Mode |
|---|---|---|
| 1 | Treprostinil | Agonist |
| 2 | Prodrug LXX (Treprostinil diproprionic ester) | Agonist |
| 3 | Prodrug LXXI (Treprostinil dicarbonate ester) | Agonist |
| 4 | Prodrug LXXII (Treprostinil diacetate ester) | Agonist |
| 5 | Prodrug LXXIII (Treprostinil diphosphate ester) | Agonist |

Cyclic AMP assay kit: Multiscreen™ TR-FRET cAMP 1.0 No Wash Assay Kit (Multispan, Inc.,)

Calcium assay kit: Multiscreen™ Calcium 1.0 No Wash Kit (Multispan, Inc., Cat #MSCA01-1)

Assay Buffer:
EP1 Calcium and DP1 cAMP Assays: HBSS plus 20 mM HEPES
EP2 and IP1 cAMP Assays: 1 mM IBMX in HBSS plus 20 mM HEPES
Instruments: FlexStation III (Molecular Devices) and FLIPR 384 (Molecular Devices)

6.3 Methods

Cells were thawed from frozen cells and resuspended in assay buffer at desired concentrations. cAMP or Calcium assays were performed according to the manufacturer's protocol using Multiscreen™ TR-FRET cAMP 1.0 No Wash Assay Kit or Multiscreen™ Calcium 1.0 No Wash Kit.

Gas Cyclic AMP (cAMP) Assay: In agonist mode testing, cells were seeded in a 384-well plate at an appropriate density and then were treated with compounds and incubated at 37° C. for 20 minutes. The reaction was terminated by sequentially adding sequentially adding trFluor™ Eu-labeled cAMP and trFluor™ 650-labeled anti-cAMP antibody in lysis buffer. The plate was then incubated at room temperature for 30 minutes before reading fluorescent emissions at 620 nm and 665 with excitation at 314 nm on FlexStation III (Molecular Devices). All testing wells contained 0.1% DMSO in the final concentrations.

Calcium Assay: Cells were seeded in a 384-well plate at an appropriate density. The calcium assay was conducted according to the manufacturer's protocols (Multiscreen Calcium 1.0 No Wash Assay Kit). The calcium dye loading buffer was added to the cells and incubated for 1 hour at 37° C. For agonist mode, cells were injected with Iloprost control agonist or test compound by FLIPR and calcium mobilization was monitored for 180 seconds with compound injected into the wells at the 19th second. Fluorescent emissions were read at 525 nm with excitation at 490 nm in a FLIPR 384 instrument (Molecular Devices).

6.4. Data Analysis

Cyclic AMP (cAMP) assays: Cyclic AMP assay results are shown as "Ratio 665/620×10,000" (ratio of fluorescence at 665 nm and 620 nm×10,000). Data in graphs are represented in Mean±SD. Dose-dependent responses were fitted with sigmoidal dose-response curves allowing variable slopes using GraphPad Prism version 6 (Graphpad Prism).

Calcium Assay: Calcium assay results are expressed as "RFU" as defined in figure below. Data are represented in Mean±SEM. Dose-response curves were fitted using "Sigmoidal dose-response (variable slope)" function in GraphPad Prism 6. EC50 values were calculated based on the fitted curves.

6.5. Results

Prostaglandin receptor activity assessments with treprostinil and treprostinil analogues have been conducted, and a historical, positive control agonist for these receptors, iloprost (for IP, EP2 and EP1) or PGD2 (for DP1), was also included. These studies used cell lines overexpressing either human IP, EP2 or DP1, or EP1 receptors, and following incubation with varying concentrations of compounds, cAMP levels were measured using Fluorescence Resonance Energy Transfer (FRET). The 665/620 (acceptor/donor emission signals) ratio is inversely proportional to the concentration of cAMP.

Figure 4:
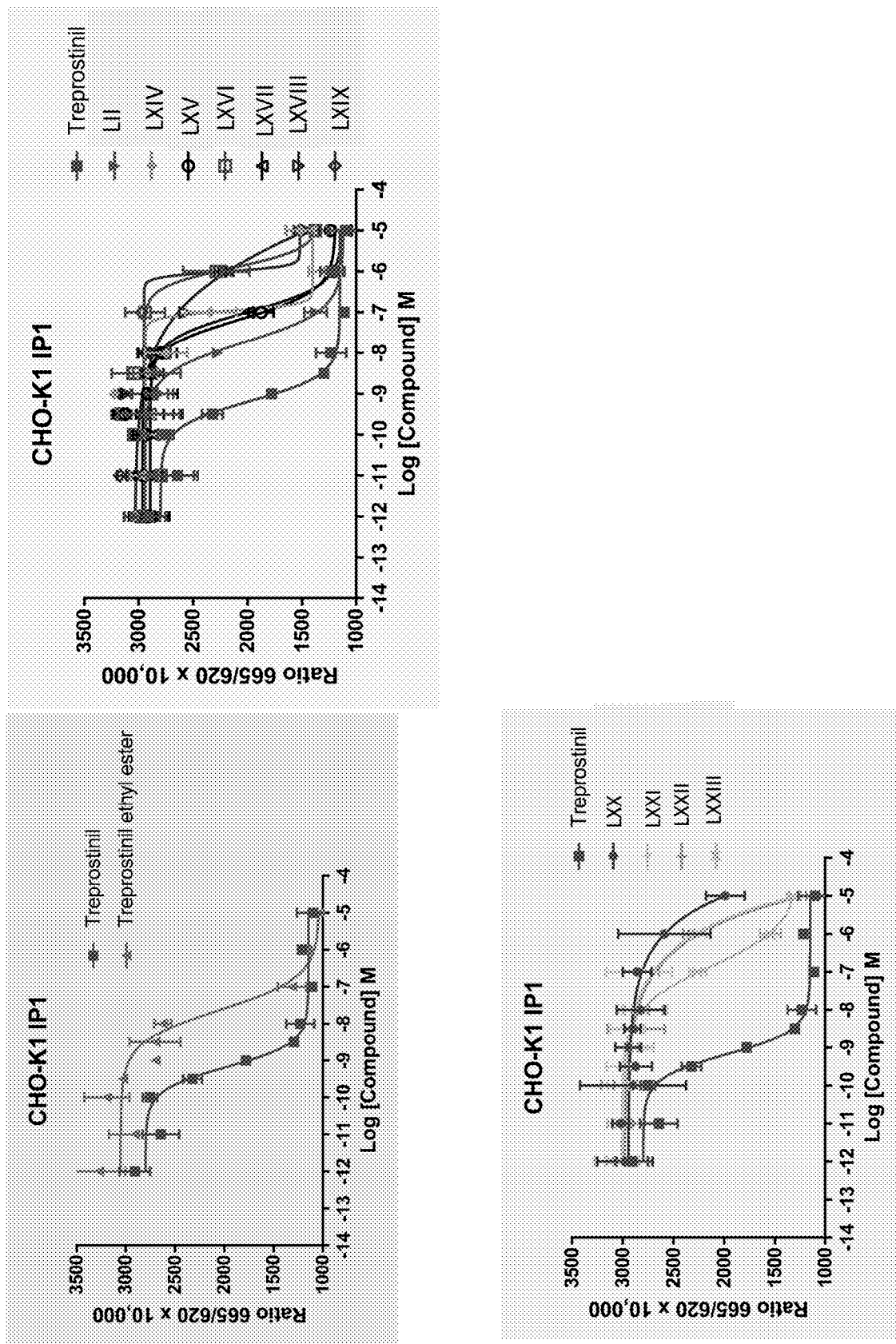
FIG. 4 presents plots comparing activities of selected treprostinil prodrugs against IP 1 receptor with that of treprostinil.
Figure 5:
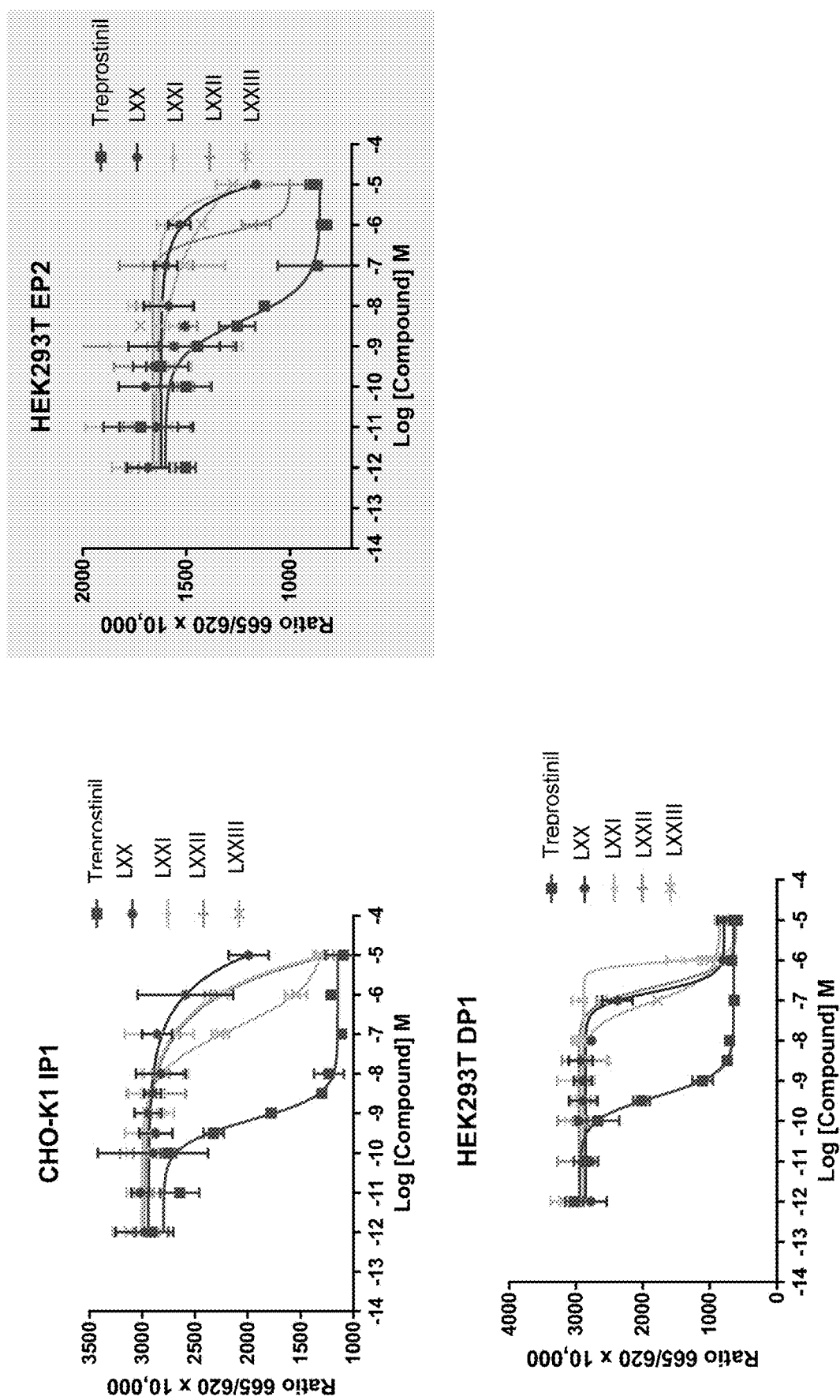
FIG. 5 presents plots comparing activities of selected treprostinil prodrugs against IP1, EP2 and DP1 receptors with those of treprostinil.

Results for treprostinil and its relative difference from the positive controls (iloprost and PGD2) were consistent with previous assessments. As shown below Tables 18 and 22-23 as well as in FIGS. 4 and 5 compared to treprostinil, the disubstituted analogs have lower activity and very different pharmacologic profiles as compared with treprostinil.

TABLE 18

EC50 Values in IP, EP2, DP1 and EP1 Receptor cAMP Assays

| Compound | $EC_{50}$ Fold Different from Treprostinil | | | |
|---|---|---|---|---|
| | IP Receptor | EP2 Receptor | DP1 Receptor | EP1 Receptor |
| Prodrug LXX | NC | NC | 410x* | NC |
| Prodrug LXXI | NC | NC | 2181x* | NC |
| Prodrug LXXII | NC | 133x* | 561x* | NC |
| Prodrug LXIII | 208x | NC | 217x* | NC |

DP1, PGD2 receptor 1; EC50, concentration that gives a half-maximal response; EP2, PGE2 receptor 2; EP1, PGE2 receptor 1; IP, PGI2 receptor
*Partial agonists or odd dose-response curves; NC = too inactive to realistically calculate.

Figure 2:
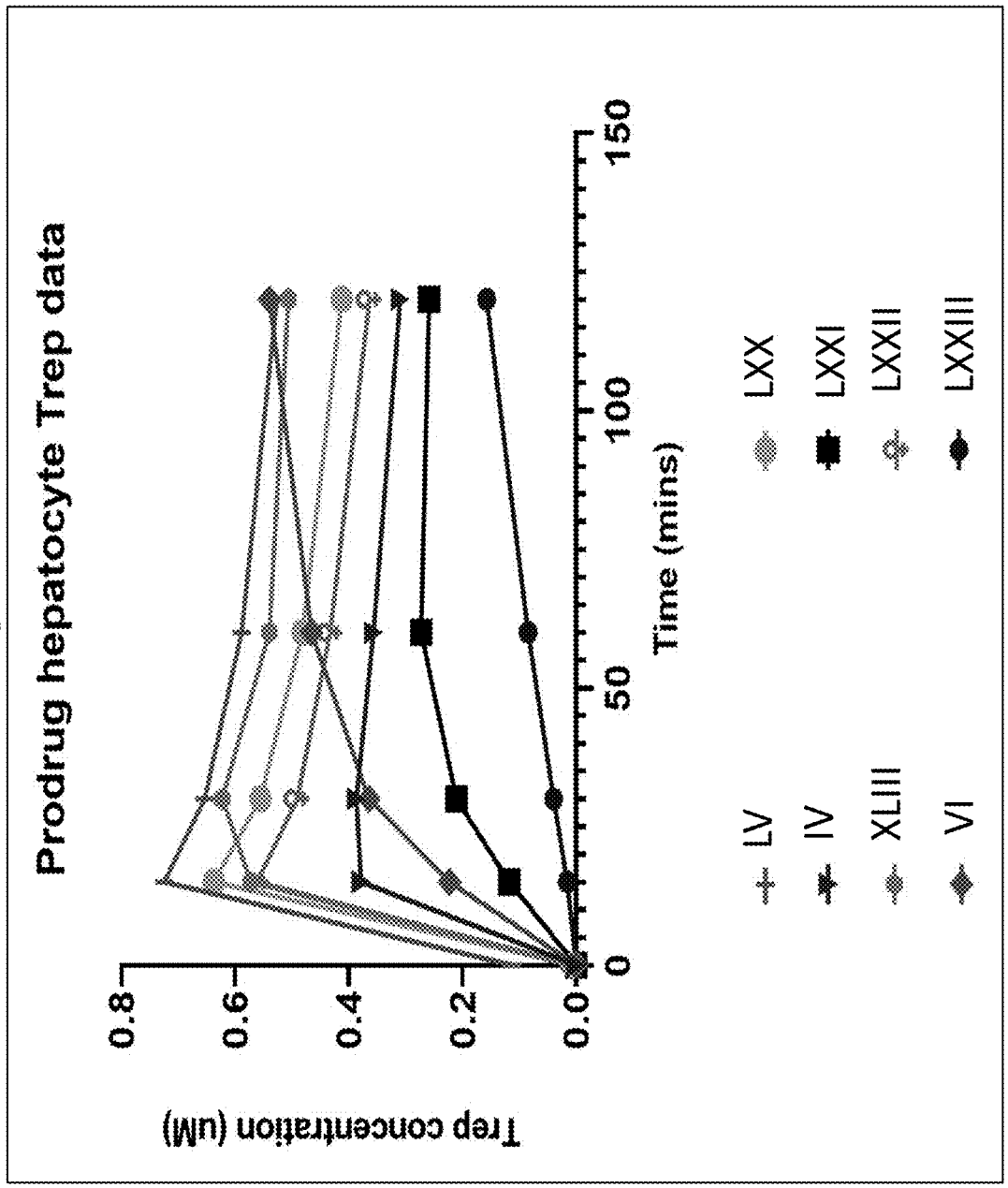
FIG. 2 is a plot presenting data for conversion to treprostinil in hepatocytes for selected treprostinil prodrugs.

Data for prodrug conversion in hepatocytes is also presented in Table 19 and in FIG. 2.

TABLE 19

Prodrug conversion in hepatocytes

| Test Article Dosed | Species | Treprostinil Concentration (μM) | | | | | Mono AUC (umoles · min/L) | Dual AUC (umoles · min/L) |
|---|---|---|---|---|---|---|---|---|
| | | 0 min | 15 min | 30 min | 60 min | 120 min | | |
| Prodrug IV | Human | 0 | 0.379 | 0.387 | 0.357 | 0.310 | 39.8 | 26.6 |
| | Rat | 0.0652 | 0.714 | 0.652 | 0.598 | 0.575 | 70.0 | 39.8 |
| | Dog | 0 | 0.513 | 0.462 | 0.399 | 0.398 | 48.0 | 41.5 |
| Prodrug VI | Human | 0 | 0.223 | 0.365 | 0.466 | 0.540 | 48.7 | 9.7 |
| | Rat | 0.128 | 0.693 | 0.635 | 0.564 | 0.53 | 66.9 | 5.3 |
| | Dog | 0.0124 | 0.581 | 0.609 | 0.533 | 0.548 | 62.9 | 20.2 |
| Prodrug XLIII | Human | 0.00744 | 0.573 | 0.623 | 0.54 | 0.507 | 62.2 | 49.9 |
| | Rat | 0.00292 | 0.161 | 0.266 | 0.397 | 0.503 | 41.4 | 32.0 |
| | Dog | 0.0381 | 0.628 | 0.543 | 0.446 | 0.4 | 54.0 | 55.7 |
| Prodrug LV | Human | 0.113 | 0.725 | 0.654 | 0.589 | 0.527 | 68.8 | 56.2 |
| | Rat | 0.0159 | 0.506 | 0.48 | 0.424 | 0.391 | 49.3 | 56.1 |
| | Dog | 0.124 | 0.781 | 0.698 | 0.599 | 0.53 | 71.2 | 61.5 |
| Prodrug LXX | Human | 0.00542 | 0.638 | 0.556 | 0.482 | 0.413 | 56.2 | |
| | Rat | 0 | 0.606 | 0.579 | 0.484 | 0.405 | 56.1 | |
| | Dog | 0.0959 | 0.736 | 0.597 | 0.511 | 0.445 | 61.5 | |
| Prodrug LXXI | Human | 0 | 0.118 | 0.211 | 0.273 | 0.259 | 26.6 | |
| | Rat | 0 | 0.422 | 0.403 | 0.347 | 0.292 | 39.8 | |
| | Dog | 0.00293 | 0.501 | 0.408 | 0.348 | 0.303 | 41.5 | |
| Prodrug LXXII | Human | 0.00458 | 0.562 | 0.491 | 0.433 | 0.364 | 49.9 | |
| | Rat | 0 | 0.24 | 0.301 | 0.298 | 0.274 | 32.0 | |
| | Dog | 0.0636 | 0.671 | 0.541 | 0.465 | 0.401 | 55.7 | |
| Prodrug LXXIII | Human | 0 | 0.0163 | 0.0399 | 0.0848 | 0.158 | 9.7 | |
| | Rat | 0 | 0.0097 | 0.0208 | 0.0431 | 0.0925 | 5.3 | |
| | Dog | 0 | 0.0506 | 0.112 | 0.195 | 0.272 | 20.2 | |

Figure 3:
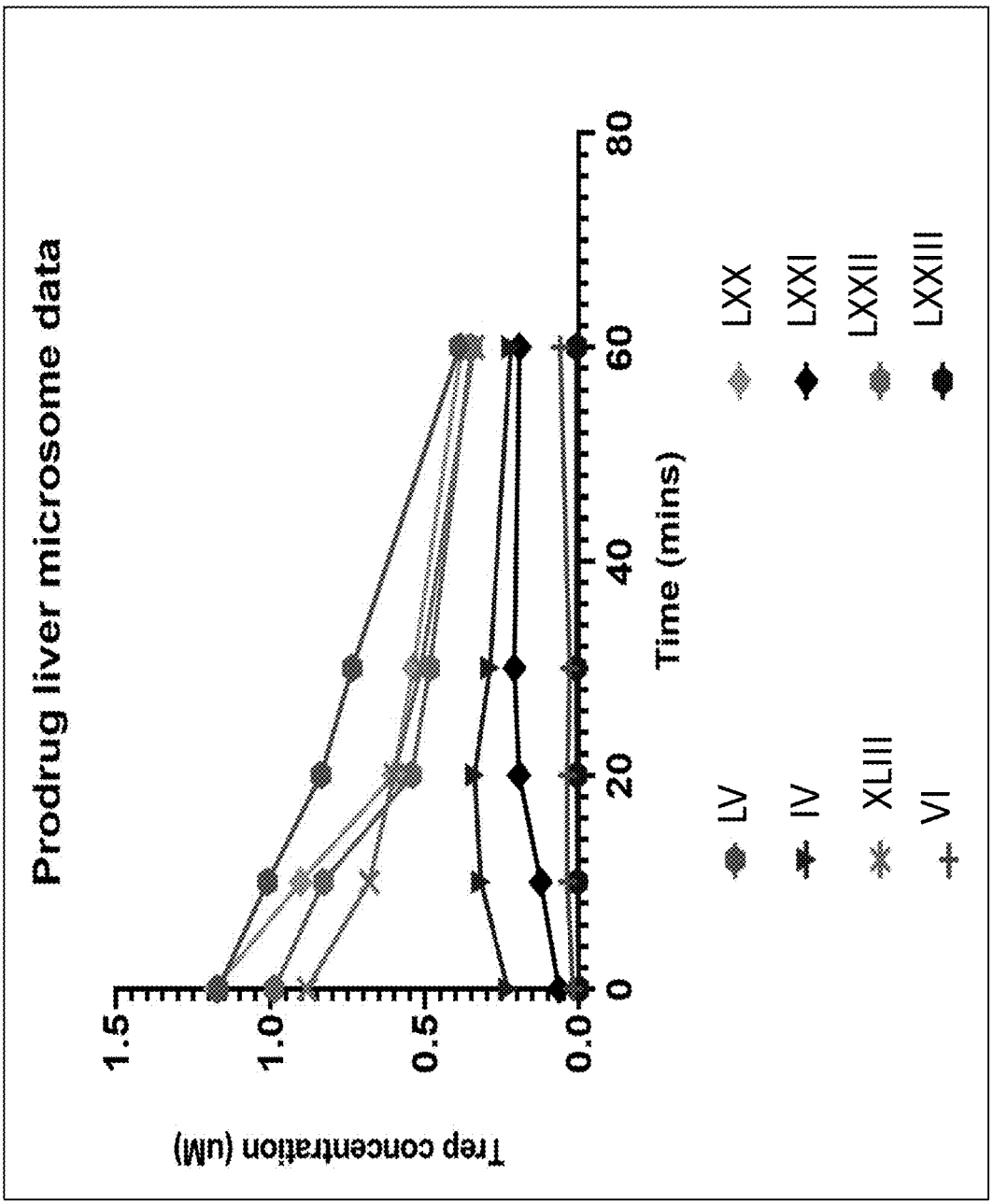
FIG. 3 is a plot presenting data for conversion to treprostinil in liver microsomes for selected treprostinil prodrugs.

Data for prodrug conversion in liver microsomes is also presented in Table 20 and in FIG. 3.

TABLE 20

Prodrug conversion in liver microsomes.

| Test Article Dosed | Species | Treprostinil Concentration (uM) | | | | | Mono AUC (umoles · min/L) | Dual AUC (umoles · min/L] |
|---|---|---|---|---|---|---|---|---|
| | | 0 min | 15 min | 30 min | 60 min | 120 min | | |
| Prodrug IV | Human | 0.23 | 0.32 | 0.34 | 0.29 | 0.22 | 16.9 | 10.6 |
| | Rat | 0.89 | 0.88 | 0.85 | 0.82 | 0.77 | 49.7 | 33.5 |
| | Dog | 0.74 | 0.95 | 0.94 | 0.94 | 0.97 | 56.0 | 56.2 |
| Prodrug VI | Human | 0.02 | 0.038 | 0.038 | 0.03 | 0.061 | 2.4 | 0.4 |
| | Rat | 0.27 | 0.39 | 0.46 | 0.53 | 0.73 | 31.4 | 0.6 |
| | Dog | 0.21 | 0.32 | 0.43 | 0.48 | 0.75 | 29.4 | 33.6 |
| Prodrug XLIII | Human | 0.883 | 0.681 | 0.602 | 0.513 | 0.341 | 32.6 | 10.0 |
| | Rat | 0.035 | 0.0741 | 0.111 | 0.145 | 0.206 | 8.0 | 60.9 |
| | Dog | 0.964 | 0.917 | 0.899 | 0.932 | 0.873 | 54.7 | 60.9 |

TABLE 20-continued

Prodrug conversion in liver microsomes.

| Test Article Dosed | Species | Treprostinil Concentration (uM) | | | | | Mono AUC (umoles · min/L) | Dual AUC (umoles · min/L] |
|---|---|---|---|---|---|---|---|---|
| | | 0 min | 15 min | 30 min | 60 min | 120 min | | |
| Prodrug LV | Human | 1.17 | 1.01 | 0.837 | 0.736 | 0.389 | 44.9 | 37.4 |
| | Rat | 0.26 | 0.43 | 0.525 | 0.586 | 0.553 | 30.9 | 38.8 |
| | Dog | 0.971 | 0.961 | 0.934 | 0.915 | 0.743 | 53.3 | 71.9 |
| Prodrug LXX | Human | 1.18 | 0.903 | 0.602 | 0.538 | 0.381 | 37.4 | |
| | Rat | 0.336 | 0.595 | 0.764 | 0.653 | 0.699 | 38.8 | |
| | Dog | 1.24 | 1.26 | 1.24 | 1.23 | 1.07 | 71.9 | |
| Prodrug LXXI | Human | 0.0646 | 0.124 | 0.194 | 0.209 | 0.192 | 10.6 | |
| | Rat | 0.301 | 0.49 | 0.638 | 0.59 | 0.595 | 33.5 | |
| | Dog | 0.875 | 0.985 | 0.979 | 0.97 | 0.853 | 56.2 | |
| Prodrug LXXII | Human | 0.989 | 0.829 | 0.543 | 0.485 | 0.349 | 33.6 | |
| | Rat | 0.0413 | 0.095 | 0.182 | 0.19 | 0.216 | 10.0 | |
| | Dog | 1.07 | 1.07 | 1.04 | 1.05 | 0.897 | 60.9 | |
| Prodrug LXXIII | Human | 0 | 0.00471 | 0.00629 | 0.00835 | 0.00762 | 0.4 | |
| | Rat | 0 | 0.00495 | 0.00898 | 0.0117 | 0.0171 | 0.6 | |
| | Dog | 0 | 0.00908 | 0.0186 | 0.0236 | 0.0294 | 1.2 | |

Table 21 presents data for conversion in skin homogenate for selected treprostinil prodrugs.

TABLE 21

Prodrug conversion in skin homogenate

| Test Article Dosed | Species | Treprostinil Concentration (µM) | | | | Mono AUC (umoles · min/L) | Dual AUC (umoles · min/L) |
|---|---|---|---|---|---|---|---|
| | | 0 min | 30 min | 60 min | 120 min | | |
| Prodrug IV | Human | 0 | 0.0443 | 0.0795 | 0.156 | 9.59 | 0.3108 |
| Prodrug VI | Human | 0 | 0.6 | 0.93 | 1.07 | 91.95 | 2.744 |
| Prodrug XLIII | Human | 0.0034 | 0.382 | 0.583 | 0.839 | 62.92 | 7.512 |
| Prodrug LV | Human | 0.0045 | 0.545 | 0.741 | 0.954 | 78.38 | 5.303 |
| Prodrug LXX | Human | 0 | 0.0179 | 0.0411 | 0.0972 | 5.303 | |
| Prodrug LXXI | Human | 0 | 0 | 0.00262 | 0.00643 | 0.3108 | |
| Prodrug LXXII | Human | 0 | 0.02 | 0.0556 | 0.147 | 7.512 | |
| Prodrug LXXIII | Human | 0 | 0.00817 | 0.0216 | 0.0509 | 2.744 | |

Tables 22-23 and FIGS. 4-5 present data for activity of selected treprostinil prodrugs against IP, EP1, EP2 and DP receptors in comparison to those of treprostinil.

TABLE 22

| | Activity | | | |
|---|---|---|---|---|
| | IP Relative to Tre | EP2 Relative to Tre | DP1 Relative to Tre | EP1 Relative to Tre |
| Prodrug VII | 875x | 110,000x | 600x | Not tested |
| Prodrug IV | 175x | 674x | 204x | Not tested |
| Prodrug VI | 5x | 4x | 2x | 5x |
| Prodrug VI repeat | 1.5x | 9x | 2x | 42x |
| Prodrug XLIII | 632x | 461x | 272x | 20x* |
| Prodrug LV | 54x | 50x | 94x | 122x* |
| Treprostinil ethyl ester | 35x | 11x | 18x | 30x |
| Prodrug LII | 27x | 26x | 73x | 133x* |
| Prodrug LXIV | 162x* | 24x* | 38x | 0.03x* |
| Prodrug LXV | 99x | 187x* | 89x | 64x* |
| Prodrug LXVI | 1803x* | ☹ | 1527x | 0.01x* |
| Prodrug LXVII | 148x | 34x* | 184x | ☹ |
| Prodrug LXVIII | ☹ | 2619x | 1048x | ☹ |
| Prodrug LXIX | 1470x* | 236x* | 1897x | ☹ |
| Di-Substituted | | | | |
| Prodrug LXX | ☹ | ☹ | 410x | ☹ |
| Prodrug LXXI | ☹ | ☹ | 2181x | ☹ |

TABLE 22-continued

| | Activity | | | |
|---|---|---|---|---|
| | IP Relative to Tre | EP2 Relative to Tre | DP1 Relative to Tre | EP1 Relative to Tre |
| Prodrug LXXII | ☹ | 133x* | 561x | ☹ |
| Prodrug LXXIII | 208x | ☹ | 217x | ☹ |

Relative to treprostinil $EC_{50}$ values
*Partial agonists or ambiguous dose-response curves
☹ = too high to realistically calculate

TABLE 23

| | Activity | | | |
|---|---|---|---|---|
| | IP Relative to Tre | EP2 Relative to Tre | DP1 Relative to Tre | EP1 Relative to Tre |
| Prodrug VII | 875x | 110,000x | 600x | Not tested |
| Prodrug IV | 175x | 674x | 204x | Not tested |
| Prodrug LXX | ☹ | ☹ | 410x | ☹ |
| Prodrug LXXI | ☹ | ☹ | 2181x* | ☹ |
| Prodrug LXXII | ☹ | 133x* | 561x | ☹ |
| Prodrug LXXIII | 208x | ☹ | 217x | ☹ |

Relative to treprostinil $EC_{50}$ values
*Partial agonists or ambiguous dose-response curves
☹ = too high to realistically calculate Tables 24, 25 and 26 present data for hydrolysis of selected treprostinil prodrugs at pH 6, 7 and 8, respectively, and 40 C.

TABLE 24

Hydrolysis of selected treprostinil prodrugs to treprostinil at pH 6 and 40 C.

| Prodrug | % Area, t = 1 week | % Area, t = 2 weeks | % Area, t = 3 weeks |
|---|---|---|---|
| Prodrug LXIV | 0.72 | 1.2 | 1.5 |
| Prodrug LXV | 0.13 | 0.29 | 0.39 |
| Prodrug LXVI | 0.47 | 1.2 | 1.9 |
| Prodrug LXVII | 0.00 | 0.00 | 0.00 |
| Prodrug LXVIII | 0.00 | 0.00 | 0.00 |
| Prodrug LXIX | 0.00 | 0.00 | 0.00 |
| Prodrug LXX | 0.00 | 0.00 | 0.00 |
| Prodrug LXXI | 0.00 | 0.00 | 0.00 |
| Prodrug LXXII | 0.00 | 0.00 | 0.00 |
| Prodrug LXXIII | 0.00 | 0.00 | 0.00 |

TABLE 25

Hydrolysis of selected treprostinil prodrugs to treprostinil at pH 7 and 40 C.

| Prodrug | % Area t = 1 week | % Area t = 2 weeks | % Area t = 3 weeks |
|---|---|---|---|
| Prodrug LXIV | 0.46 | 0.93 | 1.2 |
| Prodrug LXV | 0.96 | 1.9 | 2.7 |
| Prodrug LXVI | 0.05 | 1.0 | 1.5 |
| Prodrug LXVII | 0.00 | 0.00 | 0.00 |
| Prodrug LXVIII | 0.00 | 0.00 | 0.00 |
| Prodrug LXIX | 0.00 | 0.00 | 0.00 |
| Prodrug LXX | 0.00 | 0.00 | 0.00 |
| Prodrug LXXI | 0.00 | 0.00 | 0.00 |
| Prodrug LXXII | 0.00 | 0.00 | 0.00 |
| Prodrug LXXIII | 0.00 | 0.00 | 0.00 |

TABLE 26

Hydrolysis of selected treprostinil prodrugs to treprostinil at pH 8 and 40 C.

| Prodrug | % Area (t = 1 week) | % Area (t = 2 weeks) | % Area (t = 3 weeks) |
|---|---|---|---|
| Prodrug LXIV | 1.8 | 3.9 | 5.8 |
| Prodrug LXV | 6.0 | 11.4 | 16.9 |
| Prodrug LXVI | 0.73 | 1.6 | 2.6 |
| Prodrug LXVII | 0.00 | 0.23 | 0.27 |
| Prodrug LXVIII | 0.00 | 0.00 | 0.00 |
| Prodrug LXIX | 0.00 | 0.00 | 0.00 |
| Prodrug LXX | 0.00 | 0.00 | 0.00 |
| Prodrug LXXI | 0.00 | 0.00 | 0.38 |
| Prodrug LXXII | 0.00 | 0.00 | 0.00 |
| Prodrug LXXIII | 0.00 | 0.00 | 0.00 |

Table 27 present the data similar to Table 19, while including additional prodrugs.

TABLE 27

| Test Article Dosed | Species | Hepatocytes Trep Concentration (µM) | | | | | AUC (umoles · min/L) |
|---|---|---|---|---|---|---|---|
| | | 0 min | 15 min | 30 min | 60 min | 120 min | |
| VII | Human | 0 | 0 | 0 | 0 | 0 | 0.00 |
| | Rat | 0 | 0.0533 | 0.0793 | 0.101 | 0.122 | 10.79 |
| | Dog | 0 | 0 | 0 | 0 | 0 | 0.00 |
| IV | Human | 0 | 0.379 | 0.387 | 0.357 | 0.310 | 39.76 |
| | Rat | 0.0652 | 0.714 | 0.652 | 0.598 | 0.575 | 70.03 |
| | Dog | 0 | 0.513 | 0.462 | 0.399 | 0.398 | 47.99 |
| VIII | Human | 0 | 0 | 0 | 0.00464 | 0 | 0.21 |
| | Rat | 0 | 0 | 0 | 0.00511 | 0 | 0.23 |
| | Dog | 0 | 0 | 0 | 0 | 0 | 0.00 |
| VI | Human | 0 | 0.223 | 0.365 | 0.466 | 0.540 | 48.73 |
| | Rat | 0.128 | 0.693 | 0.635 | 0.564 | 0.53 | 66.92 |
| | Dog | 0.0124 | 0.581 | 0.609 | 0.533 | 0.548 | 62.94 |

TABLE 27-continued

| Hepatocytes | | | | | | | |
|---|---|---|---|---|---|---|---|
| Test Article Dosed | Species | Trep Concentration (µM) | | | | | AUC (umoles · min/L) |
| | | 0 min | 15 min | 30 min | 60 min | 120 min | |
| XX | Human | 0 | 0.1 | 0.16 | 0.246 | 0.344 | 26.49 |
| | Rat | 0.0112 | 0.441 | 0.542 | 0.594 | 0.609 | 63.89 |
| | Dog | 0 | 0.0459 | 0.0824 | 0.136 | 0.198 | 14.60 |
| XXIV | Human | 0.041 | 0.228 | 0.264 | 0.312 | 0.328 | 33.55 |
| | Rat | 0.365 | 0.581 | 0.531 | 0.482 | 0.431 | 58.02 |
| | Dog | 0.0779 | 0.461 | 0.438 | 0.349 | 0.296 | 41.94 |
| XXVIII | Human | 0 | 0 | 0 | 0 | 0 | 0.00 |
| | Rat | 0 | 0 | 0 | 0 | 0 | 0.00 |
| | Dog | 0 | 0 | 0 | 0 | 0.00339 | 0.10 |
| XXXII | Human | 0 | 0.0291 | 0.0508 | 0.0925 | 0.112 | 9.10 |
| | Rat | 0 | 0.0578 | 0.0983 | 0.14 | 0.199 | 15.35 |
| | Dog | 0 | 0.0344 | 0.0621 | 0.0757 | 0.105 | 8.47 |
| XXXIII | Human | 0 | 0.0192 | 0.0265 | 0.0464 | 0.0728 | 5.16 |
| | Rat | 0 | 0.0753 | 0.132 | 0.18 | 0.238 | 19.34 |
| | Dog | 0 | 0.0287 | 0.03796 | 0.0584 | 0.0754 | 6.18 |
| XXXIV | Human | 0 | 0 | 0.0107 | 0.0174 | 0.0293 | 1.90 |
| | Rat | 0 | 0.023 | 0.0447 | 0.0915 | 0.105 | 8.62 |
| | Dog | 0 | 0 | 0.0101 | 0.0153 | 0.0127 | 1.30 |
| XXXV | Human | 0 | 0.0481 | 0.0749 | 0.123 | 0.194 | 13.76 |
| | Rat | 0 | 0.0876 | 0.129 | 0.169 | 0.239 | 18.99 |
| | Dog | 0 | 0.0601 | 0.0885 | 0.127 | 0.139 | 12.78 |
| XXXVI | Human | 0 | 0.502 | 0.512 | 0.45 | 0.482 | 53.76 |
| | Rat | 0.00925 | 0.494 | 0.511 | 0.505 | 0.499 | 56.67 |
| | Dog | 0 | 0.229 | 0.276 | 0.264 | 0.279 | 29.90 |
| XXXVII | Human | 0 | 0.0481 | 0.041 | 0.0715 | 0.115 | 8.31 |
| | Rat | 0 | 0.0136 | 0.0199 | 0.106 | 0.0527 | 7.00 |
| | Dog | 0 | 0.0424 | 0.0879 | 0.147 | 0.248 | 16.67 |
| XLII | Human | 0.297 | 0.274 | 0.298 | 0.275 | 0.217 | 31.93 |
| | Rat | 0.33 | 0.309 | 0.299 | 0.307 | 0.3 | 36.65 |
| | Dog | 0.296 | 0.242 | 0.197 | 0.155 | 0.137 | 21.37 |
| XLIII | Human | 0.00744 | 0.573 | 0.623 | 0.54 | 0.507 | 62.18 |
| | Rat | 0.00292 | 0.161 | 0.266 | 0.397 | 0.503 | 41.38 |
| | Dog | 0.0381 | 0.628 | 0.543 | 0.446 | 0.4 | 53.99 |
| XLIV | Human | 0.0377 | 0.406 | 0.534 | 0.553 | 0.506 | 58.45 |
| | Rat | 0.0352 | 0.186 | 0.307 | 0.393 | 0.514 | 43.07 |
| | Dog | 0.0501 | 0.587 | 0.545 | 0.475 | 0.404 | 54.94 |
| XLV | Human | 0 | 0.0417 | 0.0533 | 0.0724 | 0.0734 | 7.29 |
| | Rat | 0 | 0.00378 | 0.00483 | 0.00537 | 0.00521 | 0.56 |
| | Dog | 0 | 0 | 0 | 0 | 0 | 0.00 |
| XLVI | Human | 0 | 0.00507 | 0.00509 | 0.00568 | 0.0061 | 0.63 |
| | Rat | 0 | 0.0144 | 0.0194 | 0.0209 | 0.0224 | 2.27 |
| | Dog | 0 | 0.00361 | 0.00376 | 0.00437 | 0.00465 | 0.47 |
| XLVII | Human | 0 | 0.0152 | 0.0199 | 0.0215 | 0.0212 | 2.28 |
| | Rat | 0 | 0.0168 | 0.0209 | 0.0231 | 0.0216 | 2.41 |
| | Dog | 0 | 0 | 0 | 0.00355 | 0.00371 | 0.27 |
| XLVIII | Human | 0 | 0.342 | 0.304 | 0.345 | 0.347 | 37.91 |
| | Rat | 0 | 0.1 | 0.141 | 0.221 | 0.318 | 24.16 |
| | Dog | 0 | 0.0841 | 0.115 | 0.177 | 0.214 | 18.23 |
| XLIX | Human | 0 | 0.192 | 0.179 | 0.217 | 0.237 | 23.78 |
| | Rat | 0 | 0.00943 | 0.0122 | 0.0182 | 0.0273 | 2.05 |
| | Dog | 0 | 0.0727 | 0.111 | 0.19 | 0.258 | 19.88 |
| L | Human | 0.00177 | 0.00195 | 0.00202 | 0.00194 | 0.00197 | 0.23 |
| | Rat | 0 | 0.00347 | 0.00366 | 0.00352 | 0.0034 | 0.39 |
| | Dog | 0.00247 | 0.00312 | 0.0106 | 0.00355 | 0.00568 | 0.63 |
| LI | Human | 0.0425 | 0.647 | 0.626 | 0.608 | 0.55 | 67.97 |
| | Rat | 0.327 | 0.703 | 0.61 | 0.523 | 0.464 | 64.18 |
| | Dog | 0.0214 | 0.627 | 0.605 | 0.537 | 0.482 | 61.80 |
| LXIII | Human | 0.0167 | 0.0193 | 0.0179 | 0.0183 | 0.0185 | 2.20 |
| | Rat | 0.0132 | 0.0112 | 0.0132 | 0.00957 | 0.00865 | 1.25 |
| | Dog | 0.0147 | 0.0171 | 0.0158 | 0.0103 | 0.00943 | 1.47 |
| LIV | Human | 0.0156 | 0.58 | 0.47 | 0.475 | 0.461 | 54.60 |
| | Rat | 0.0862 | 0.512 | 0.426 | 0.441 | 0.455 | 51.41 |
| | Dog | 0.00351 | 0.295 | 0.273 | 0.262 | 0.262 | 30.24 |
| LV | Human | 0.113 | 0.725 | 0.654 | 0.589 | 0.527 | 68.75 |
| | Rat | 0.0159 | 0.506 | 0.48 | 0.424 | 0.391 | 49.32 |
| | Dog | 0.124 | 0.781 | 0.698 | 0.599 | 0.53 | 71.21 |
| LVI | Human | 0 | 0 | 0 | 0 | 0 | 0.00 |
| | Rat | 0 | 0 | 0 | 0 | 0 | 0.00 |
| | Dog | 0 | 0.005 | 0.005 | 0.003 | 0 | 0.00 |
| LVII | Human | 0 | 0 | 0 | 0 | 0 | 0.00 |
| | Rat | 0 | 0 | 0 | 0 | 0 | 0.00 |
| | Dog | 0 | 0 | 0 | 0 | 0 | 0.00 |

TABLE 27-continued

| | Hepatocytes | | | | | | |
|---|---|---|---|---|---|---|---|
| Test Article | | Trep Concentration (μM) | | | | | AUC (umoles · |
| Dosed | Species | 0 min | 15 min | 30 min | 60 min | 120 min | min/L) |
| LVIII | Human | 0 | 0 | 0 | 0 | 0 | 0.00 |
| | Rat | 0 | 0 | 0 | 0 | 0 | 0.00 |
| | Dog | 0 | 0 | 0.00519 | 0.00214 | 0.00344 | 0.32 |
| LIX | Human | 0 | 0 | 0 | 0 | 0 | 0.00 |
| | Rat | 0 | 0 | 0 | 0 | 0 | 0.00 |
| | Dog | 0 | 0 | 0.00416 | 0.00836 | 0.00907 | 0.74 |
| LX | Human | 0 | 0.0671 | 0.102 | 0.123 | 0.137 | 12.95 |
| | Rat | 0 | 0.021 | 0.0343 | 0.0477 | 0.0634 | 5.14 |
| | Dog | 0 | 0.00428 | 0.00492 | 0.00784 | 0.0117 | 0.88 |
| LXI | Human | 0 | 0.0213 | 0.0378 | 0.0556 | 0.0701 | 5.78 |
| | Rat | 0 | 0 | 0.00373 | 0.00634 | 0.00941 | 0.65 |
| | Dog | 0 | 0 | 0.00299 | 0.00396 | 0.00663 | 0.44 |
| LXII | Human | 0 | 0.0881 | 0.14 | 0.194 | 0.222 | 19.86 |
| | Rat | 0.00378 | 0.0946 | 0.156 | 0.227 | 0.264 | 23.09 |
| | Dog | 0 | 0.0486 | 0.0833 | 0.128 | 0.166 | 13.34 |
| LXIII | Human | 0 | 0.0907 | 0.166 | 0.242 | 0.281 | 24.42 |
| | Rat | 0 | 0.0539 | 0.0952 | 0.157 | 0.227 | 16.83 |
| | Dog | 0 | 0.038 | 0.0746 | 0.114 | 0.168 | 12.42 |
| LXIV | Human | 0.0116 | 0.521 | 0.509 | 0.458 | 0.411 | 52.29 |
| | Rat | 0.0456 | 0.374 | 0.291 | 0.234 | 0.206 | 29.21 |
| | Dog | 0.0196 | 0.466 | 0.514 | 0.485 | 0.451 | 54.06 |
| LXV | Human | 0.0193 | 0.559 | 0.515 | 0.452 | 0.39 | 52.16 |
| | Rat | 0.0517 | 0.379 | 0.289 | 0.237 | 0.2 | 29.24 |
| | Dog | 0.0135 | 0.484 | 0.465 | 0.406 | 0.373 | 47.28 |
| LXVI | Human | 0 | 0.0209 | 0.0147 | 0.0184 | 0.0237 | 2.18 |
| | Rat | 0 | 0 | 0 | 0 | 0 | 0.00 |
| | Dog | 0 | 0 | 0 | 0 | 0.00519 | 0.16 |
| LXVII | Human | 0.0174 | 0.631 | 0.572 | 0.506 | 0.446 | 58.62 |
| | Rat | 0 | 0.215 | 0.217 | 0.189 | 0.172 | 21.77 |
| | Dog | 0.09 | 0.616 | 0.554 | 0.459 | 0.42 | 55.64 |
| LXVIII | Human | 0 | 0.147 | 0.194 | 0.195 | 0.17 | 20.45 |
| | Rat | 0 | 0 | 0.00403 | 0.00545 | 0.00743 | 0.56 |
| | Dog | 0 | 0.0142 | 0.00583 | 0.00715 | 0.0129 | 1.05 |
| LXIX | Human | 0 | 0.198 | 0.294 | 0.338 | 0.335 | 34.85 |
| | Rat | 0 | 0.0238 | 0.0421 | 0.0712 | 0.119 | 8.08 |
| | Dog | 0.00877 | 0.227 | 0.262 | 0.263 | 0.236 | 28.28 |
| LXX | Human | 0.00542 | 0.638 | 0.556 | 0.482 | 0.413 | 56.2 |
| | Rat | 0 | 0.606 | 0.579 | 0.484 | 0.405 | 56.05 |
| | Dog | 0.0959 | 0.736 | 0.597 | 0.511 | 0.445 | 61.54 |
| LXXI | Human | 0 | 0.118 | 0.211 | 0.273 | 0.259 | 26.57 |
| | Rat | 0 | 0.422 | 0.403 | 0.347 | 0.292 | 39.77 |
| | Dog | 0.00293 | 0.501 | 0.408 | 0.348 | 0.303 | 41.47 |
| LXXII | Human | 0.00458 | 0.562 | 0.491 | 0.433 | 0.364 | 49.92 |
| | Rat | 0 | 0.24 | 0.301 | 0.298 | 0.274 | 32 |
| | Dog | 0.0636 | 0.671 | 0.541 | 0.465 | 0.401 | 55.67 |
| LXXIII | Human | 0 | 0.0163 | 0.0399 | 0.0848 | 0.158 | 9.698 |
| | Rat | 0 | 0.0097 | 0.0208 | 0.0431 | 0.0925 | 5.328 |
| | Dog | 0 | 0.0506 | 0.112 | 0.195 | 0.272 | 20.21 |

Table 28 provides data similar to Table 20 while including additional prodrugs.

TABLE 28

| | Liver Microsomes | | | | | | |
|---|---|---|---|---|---|---|---|
| Test Article | | Trep Concentration (uM) | | | | | AUC (umoles · |
| Dosed | Species | 0 min | 10 min | 20 min | 30 min | 60 min | min/L) |
| VII | Human | 0 | 0 | 0 | 0 | 0 | 0.00 |
| | Rat | 0 | 0 | 0 | 0 | 0.026 | 0.39 |
| | Dog | 0 | 0 | 0 | 0 | 0 | 0.00 |
| IV | Human | 0.23 | 0.32 | 0.34 | 0.29 | 0.22 | 16.85 |
| | Rat | 0.89 | 0.88 | 0.85 | 0.82 | 0.77 | 49.70 |
| | Dog | 0.74 | 0.95 | 0.94 | 0.94 | 0.97 | 55.95 |
| XVI | Human | 0.69 | 0.6 | 0.49 | 0.41 | 0.25 | 26.30 |
| | Rat | 0.98 | 0.97 | 0.92 | 0.91 | 0.86 | 54.90 |
| | Dog | 0.66 | 0.95 | 1.01 | 1.01 | 0.92 | 56.90 |

TABLE 28-continued

| | | Liver Microsomes | | | | | |
|---|---|---|---|---|---|---|---|
| Test Article Dosed | Species | Trep Concentration (uM) | | | | | AUC (umoles · min/L) |
| | | 0 min | 10 min | 20 min | 30 min | 60 min | |
| XVII | Human | 0.55 | 0.55 | 0.5 | 0.39 | 0.27 | 25.10 |
| | Rat | 0.29 | 0.46 | 0.48 | 0.53 | 0.53 | 29.40 |
| | Dog | 0.45 | 0.57 | 0.66 | 0.74 | 0.85 | 42.10 |
| VI | Human | 0.02 | 0.038 | 0.038 | 0.03 | 0.061 | 2.38 |
| | Rat | 0.27 | 0.39 | 0.46 | 0.53 | 0.73 | 31.40 |
| | Dog | 0.21 | 0.32 | 0.43 | 0.48 | 0.75 | 29.40 |
| XIX | Human | 0 | 0 | 0.014 | 0.018 | 0.022 | 0.83 |
| | Rat | 0 | 0 | 0 | 0 | 0 | 0.00 |
| | Dog | 0 | 0 | 0 | 0 | 0 | 0.00 |
| XX | Human | 0.048 | 0.087 | 0.092 | 0.1 | 0.16 | 6.43 |
| | Rat | 0.12 | 0.24 | 0.29 | 0.38 | 0.54 | 21.60 |
| | Dog | 0.019 | 0.044 | 0.087 | 0.11 | 0.2 | 6.61 |
| XXII | Human | 0 | 0 | 0 | 0 | 0 | 0.00 |
| | Rat | 0 | 0 | 0 | 0 | 0.016 | 0.24 |
| | Dog | 0 | 0 | 0 | 0 | 0 | 0.00 |
| XXIV | Human | 0.326 | 0.342 | 0.341 | 0.326 | 0.23 | 18.43 |
| | Rat | 0.779 | 0.791 | 0.79 | 0.802 | 0.681 | 45.96 |
| | Dog | 0.892 | 0.975 | 0.948 | 0.945 | 0.86 | 55.49 |
| XXVIII | Human | 0 | 0 | 0 | 0 | 0 | 0.00 |
| | Rat | 0 | 0 | 0 | 0 | 0 | 0.00 |
| | Dog | 0 | 0 | 0.00553 | 0.003 | 0 | 0.11 |
| XXIX | Human | 0.00482 | 0.0117 | 0.0168 | 0.0173 | 0.0265 | 1.05 |
| | Rat | 0 | 0.00463 | 0.00443 | 0.0102 | 0.0178 | 0.56 |
| | Dog | 0 | 0.012 | 0.0177 | 0.025 | 0.0334 | 1.30 |
| XXX | Human | 0.036 | 0.132 | 0.227 | 0.31 | 0.429 | 16.41 |
| | Rat | 0.011 | 0.0524 | 0.0901 | 0.122 | 0.196 | 6.86 |
| | Dog | 0.0977 | 0.347 | 0.495 | 0.562 | 0.664 | 30.11 |
| XXXI | Human | 0.0531 | 0.193 | 0.31 | 0.327 | 0.383 | 17.58 |
| | Rat | 0.00504 | 0.0179 | 0.0351 | 0.0465 | 0.107 | 3.09 |
| | Dog | 0.134 | 0.479 | 0.63 | 0.674 | 0.694 | 35.65 |
| XXXII | Human | 0 | 0.0136 | 0.01961 | 0.0164 | 0.0215 | 0.98 |
| | Rat | 0.0104 | 0.0192 | 0.0243 | 0.0207 | 0.0338 | 1.41 |
| | Dog | 0.0347 | 0.0738 | 0.111 | 0.124 | 0.183 | 7.25 |
| XXXIII | Human | 0 | 0 | 0 | 0 | 0 | 0.00 |
| | Rat | 0.0107 | 0.0193 | 0.0291 | 0.0305 | 0.0498 | 1.90 |
| | Dog | 0.0247 | 0.0494 | 0.0751 | 0.0888 | 0.13 | 5.10 |
| XXXIV | Human | 0 | 0 | 0 | 0 | 0 | 0.00 |
| | Rat | 0 | 0 | 0.0132 | 0.0158 | 0.0224 | 0.78 |
| | Dog | 0 | 0 | 0 | 0 | 0.0104 | 0.16 |
| XXXV | Human | 0.0227 | 0.0216 | 0.0492 | 0.0352 | 0.0539 | 2.33 |
| | Rat | 0.0254 | 0.0305 | 0.0389 | 0.0458 | 0.079 | 2.92 |
| | Dog | 0.0159 | 0.0246 | 0.0405 | 0.0449 | 0.0788 | 2.81 |
| XXXVI | Human | 0.443 | 0.502 | 0.478 | 0.379 | 0.316 | 24.34 |
| | Rat | 0.154 | 0.242 | 0.326 | 0.342 | 0.463 | 20.24 |
| | Dog | 0.102 | 0.199 | 0.309 | 0.353 | 0.483 | 19.90 |
| XXXVII | Human | 0 | 0.0147 | 0 | 0.0153 | 0.00987 | 0.60 |
| | Rat | 0 | 0 | 0 | 0 | 0 | 0.00 |
| | Dog | 0.0163 | 0.0171 | 0.0295 | 0.0273 | 0.0415 | 1.72 |
| XXXVIII | Human | 0 | 0 | 0 | 0 | 0 | 0.00 |
| | Rat | 0 | 0 | 0 | 0 | 0 | 0.00 |
| | Dog | 0 | 0 | 0 | 0 | 0 | 0.00 |
| XXXIX | Human | 0 | 0 | 0 | 0 | 0 | 0.00 |
| | Rat | 0 | 0 | 0 | 0 | 0 | 0.00 |
| | Dog | 0 | 0 | 0 | 0 | 0 | 0.00 |
| XLII | Human | 0.361 | 0.297 | 0.293 | 0.273 | 0.219 | 16.45 |
| | Rat | 0.322 | 0.296 | 0.314 | 0.308 | 0.29 | 18.22 |
| | Dog | 0.335 | 0.312 | 0.311 | 0.308 | 0.323 | 18.91 |
| XLIII | Human | 0.883 | 0.681 | 0.602 | 0.513 | 0.341 | 32.62 |
| | Rat | 0.035 | 0.0741 | 0.111 | 0.145 | 0.206 | 8.02 |
| | Dog | 0.964 | 0.917 | 0.899 | 0.932 | 0.873 | 54.72 |
| XLIV | Human | 0.624 | 0.632 | 0.549 | 0.52 | 0.307 | 29.94 |
| | Rat | 0.0772 | 0.114 | 0.157 | 0.197 | 0.284 | 11.30 |
| | Dog | 0.913 | 0.884 | 0.828 | 0.894 | 0.899 | 53.05 |
| XLV | Human | 0.00583 | 0.104 | 0.156 | 0.21 | 0.292 | 11.21 |
| | Rat | 0 | 0.00607 | 0.00992 | 0.0162 | 0.023 | 0.83 |
| | Dog | 0 | 0 | 0.00323 | 0.00529 | 0.00637 | 0.23 |
| XLVI | Human | 0 | 0.0342 | 0.0556 | 0.0656 | 0.0835 | 3.46 |
| | Rat | 0 | 0.0425 | 0.0633 | 0.0882 | 0.123 | 4.67 |
| | Dog | 0 | 0.0211 | 0.0334 | 0.0485 | 0.0841 | 2.78 |
| XLVII | Human | 0 | 0.0448 | 0.0686 | 0.0816 | 0.124 | 4.63 |
| | Rat | 0 | 0.0292 | 0.0421 | 0.0553 | 0.0719 | 2.90 |
| | Dog | 0 | 0.0118 | 0.0187 | 0.0285 | 0.0499 | 1.62 |

TABLE 28-continued

| | Liver Microsomes | | | | | | |
|---|---|---|---|---|---|---|---|
| Test Article Dosed | Species | Trep Concentration (uM) | | | | | AUC (umoles · min/L) |
| | | 0 min | 10 min | 20 min | 30 min | 60 min | |
| XLVIII | Human | 0.202 | 0.302 | 0.322 | 0.337 | 0.352 | 19.27 |
| | Rat | 0.0583 | 0.0944 | 0.0864 | 0.0909 | 0.123 | 5.76 |
| | Dog | 0.119 | 0.219 | 0.322 | 0.366 | 0.475 | 20.45 |
| XLIX | Human | 0.137 | 0.171 | 0.174 | 0.163 | 0.125 | 9.27 |
| | Rat | 0 | 0.00512 | 0.00637 | 0.009 | 0.0074 | 0.41 |
| | Dog | 0.17 | 0.325 | 0.433 | 0.451 | 0.558 | 25.82 |
| L | Human | 0.00327 | 0.00286 | 0.00309 | 0.00264 | 0.00244 | 0.17 |
| | Rat | 0.00345 | 0.00356 | 0.00419 | 0.00488 | 0.00552 | 0.28 |
| | Dog | 0.00302 | 0.00333 | 0.00398 | 0.00409 | 0.00389 | 0.23 |
| LII | Human | 0.948 | 0.798 | 0.679 | 0.538 | 0.346 | 35.46 |
| | Rat | 0.937 | 0.938 | 0.892 | 0.838 | 0.802 | 51.78 |
| | Dog | 0.758 | 0.885 | 0.868 | 0.834 | 0.84 | 50.60 |
| LIII | Human | 0.0216 | 0.0336 | 0.0343 | 0.0459 | 0.0354 | 2.24 |
| | Rat | 0.0196 | 0.0177 | 0.024 | 0.0274 | 0.0271 | 1.47 |
| | Dog | 0.0189 | 0.0224 | 0.0209 | 0.0236 | 0.0222 | 1.33 |
| LIV | Human | 0.908 | 0.679 | 0.564 | 0.463 | 0.338 | 31.30 |
| | Rat | 0.849 | 0.784 | 0.765 | 0.709 | 0.811 | 46.08 |
| | Dog | 0.307 | 0.544 | 0.678 | 0.729 | 0.777 | 39.99 |
| LV | Human | 1.17 | 1.01 | 0.837 | 0.736 | 0.389 | 44.88 |
| | Rat | 0.26 | 0.43 | 0.525 | 0.586 | 0.553 | 30.87 |
| | Dog | 0.971 | 0.961 | 0.934 | 0.915 | 0.743 | 53.25 |
| LVI | Human | 0 | 0 | 0 | 0 | 0 | 0.00 |
| | Rat | 0 | 0 | 0 | 0 | 0 | 0.00 |
| | Dog | 0 | 0 | 0.003 | 0 | 0 | 0.00 |
| LVII | Human | 0 | 0 | 0 | 0 | 0 | 0.00 |
| | Rat | 0 | 0 | 0 | 0 | 0 | 0.00 |
| | Dog | 0 | 0 | 0 | 0 | 0 | 0.00 |
| LVIII | Human | 0 | 0 | 0 | 0 | 0 | 0.00 |
| | Rat | 0 | 0 | 0 | 0 | 0 | 0.00 |
| | Dog | 0 | 0 | 0 | 0 | 0 | 0.00 |
| LIX | Human | 0 | 0 | 0 | 0 | 0 | 0.00 |
| | Rat | 0 | 0 | 0 | 0 | 0 | 0.00 |
| | Dog | 0 | 0 | 0 | 0 | 0 | 0.00 |
| LX | Human | 0.105 | 0.14 | 0.137 | 0.126 | 0.0865 | 7.11 |
| | Rat | 0.0226 | 0.033 | 0.0396 | 0.0481 | 0.0609 | 2.72 |
| | Dog | 0.0189 | 0.0283 | 0.0363 | 0.044 | 0.059 | 2.51 |
| LXI | Human | 0.0209 | 0.0312 | 0.0361 | 0.0389 | 0.0332 | 2.05 |
| | Rat | 0 | 0 | 0.00316 | 0.00337 | 0.00402 | 0.16 |
| | Dog | 0.00725 | 0.0115 | 0.0157 | 0.0196 | 0.0259 | 1.09 |
| LXII | Human | 0.0917 | 0.141 | 0.174 | 0.2 | 0.206 | 10.70 |
| | Rat | 0.0741 | 0.0998 | 0.124 | 0.139 | 0.139 | 7.47 |
| | Dog | 0.127 | 0.188 | 0.254 | 0.3 | 0.372 | 16.64 |
| LXIII | Human | 0.12 | 0.184 | 0.24 | 0.268 | 0.275 | 14.33 |
| | Rat | 0.0393 | 0.0539 | 0.0653 | 0.0747 | 0.0824 | 4.12 |
| | Dog | 0.104 | 0.16 | 0.222 | 0.243 | 0.342 | 14.33 |
| LXIV | Human | 0.911 | 0.752 | 0.667 | 0.596 | 0.351 | 35.93 |
| | Rat | 0.803 | 0.882 | 0.91 | 0.902 | 0.753 | 51.27 |
| | Dog | 0.453 | 0.548 | 0.592 | 0.603 | 0.627 | 35.13 |
| LXV | Human | 0.921 | 0.762 | 0.67 | 0.594 | 0.351 | 36.07 |
| | Rat | 0.889 | 0.898 | 0.885 | 0.888 | 0.738 | 51.11 |
| | Dog | 0.903 | 0.912 | 0.864 | 0.801 | 0.728 | 49.22 |
| LXVI | Human | 0.0131 | 0.0155 | 0.0171 | 0.0168 | 0.0141 | 0.94 |
| | Rat | 0 | 0.00332 | 0.00368 | 0.00422 | 0.00722 | 0.26 |
| | Dog | 0 | 0 | 0 | 0.00396 | 0.00602 | 0.17 |
| LXVII | Human | 1.02 | 0.877 | 0.755 | 0.664 | 0.393 | 40.60 |
| | Rat | 0.281 | 0.369 | 0.419 | 0.471 | 0.433 | 25.20 |
| | Dog | 0.987 | 0.972 | 0.982 | 0.993 | 0.816 | 56.58 |
| LXVIII | Human | 0.201 | 0.237 | 0.246 | 0.252 | 0.178 | 13.55 |
| | Rat | 0.00607 | 0.00792 | 0.0105 | 0.0127 | 0.0145 | 0.69 |
| | Dog | 0.0171 | 0.0246 | 0.0324 | 0.0375 | 0.0382 | 1.98 |
| LXIX | Human | 0.321 | 0.365 | 0.367 | 0.36 | 0.252 | 19.91 |
| | Rat | 0.0251 | 0.0344 | 0.0421 | 0.0483 | 0.0527 | 2.65 |
| | Dog | 0.517 | 0.57 | 0.609 | 0.696 | 0.657 | 38.15 |
| LXX | Human | 1.18 | 0.903 | 0.602 | 0.538 | 0.381 | 37.43 |
| | Rat | 0.336 | 0.595 | 0.764 | 0.653 | 0.699 | 38.82 |
| | Dog | 1.24 | 1.26 | 1.24 | 1.23 | 1.07 | 71.85 |
| LXXI | Human | 0.0646 | 0.124 | 0.194 | 0.209 | 0.192 | 10.56 |
| | Rat | 0.301 | 0.49 | 0.638 | 0.59 | 0.595 | 33.51 |
| | Dog | 0.875 | 0.985 | 0.979 | 0.97 | 0.853 | 56.21 |
| LXXII | Human | 0.989 | 0.829 | 0.543 | 0.485 | 0.349 | 33.6 |
| | Rat | 0.0413 | 0.095 | 0.182 | 0.19 | 0.216 | 10.02 |
| | Dog | 1.07 | 1.07 | 1.04 | 1.05 | 0.897 | 60.91 |

TABLE 28-continued

Liver Microsomes

| Test Article Dosed | Species | Trep Concentration (uM) | | | | | AUC (umoles · min/L) |
|---|---|---|---|---|---|---|---|
| | | 0 min | 10 min | 20 min | 30 min | 60 min | |
| LXXIII | Human | 0 | 0.00471 | 0.00629 | 0.00835 | 0.00762 | 0.3913 |
| | Rat | 0 | 0.00495 | 0.00898 | 0.0117 | 0.0171 | 0.6298 |
| | Dog | 0 | 0.00908 | 0.0186 | 0.0236 | 0.0294 | 1.19 |

Table 29 provides data similar to Table 21 while providing data for additional prodrugs

TABLE 29

| Test Article Dosed | Species | Skin Homogenate Trep Concentration (μM) | | | | AUC (umoles · min/L) |
|---|---|---|---|---|---|---|
| | | 0 min | 30 min | 60 min | 120 min | |
| VII orig | Human | 0 | 0 | 0 | 0.0047 | 0.14 |
| VII new | Human | 0 | 0 | 0 | 0 | 0.00 |
| IV 1st | Human | 0 | 0.032 | 0.069 | 0.1 | 7.07 |
| IV 2nd | Human | 0 | 0.364 | 0.575 | 0.863 | 62.69 |
| IV 3rd | Human | 0 | 0.0443 | 0.0795 | 0.156 | 9.59 |
| VIII | Human | 0 | 0 | 0 | 0 | 0.00 |
| XVI | Human | 0 | 0.17 | 0.31 | 0.53 | 34.95 |
| XVII | Human | 0 | 0.064 | 0.12 | 0.22 | 13.92 |
| VI | Human | 0 | 0.6 | 0.93 | 1.07 | 91.95 |
| XIX | Human | 0 | 0 | 0 | 0 | 0.00 |
| XX | Human | 0 | 0 | 0.019 | 0.03 | 1.76 |
| XX new | Human | 0 | 0.00878 | 0.0149 | 0.0271 | 1.75 |
| XXII | Human | 0 | 0 | 0 | 0 | 0.00 |
| XXIV | Human | | | | | |
| XXVIII | Human | | | | | |
| XXIX | Human | 0 | 0.0333 | 0.0488 | 0.0759 | 5.47 |
| XXX | Human | 0 | 0.206 | 0.369 | 0.533 | 38.78 |
| XXXI | Human | 0 | 0.112 | 0.204 | 0.323 | 22.23 |
| XXXII | Human | 0 | 0 | 0 | 0 | 0.00 |
| XXXIII | Human | 0 | 0 | 0 | 0 | 0.00 |
| XXXIV | Human | 0 | 0 | 0 | 0 | 0.00 |
| XXXV | Human | 0 | 0.857 | 0.82 | 0.929 | 90.48 |
| XXXVI | Human | 0 | 0.328 | 0.559 | 0.852 | 60.56 |
| XXXVII | Human | 0 | 0 | 0.0137 | 0.0304 | 1.53 |
| XXXVIII | Human | 0 | 0 | 0 | 0 | 0.00 |
| XXXIX | Human | 0 | 0 | 0 | 0 | 0.00 |
| XL | Human | 0 | 0.202 | 0.329 | 0.59 | 38.57 |
| XLI | Human | 0 | 0.0526 | 0.091 | 0.19 | 11.37 |
| XLII | Human | 0 | 0 | 0 | 0 | 0.00 |
| XLIII | Human | 0 | 0.0528 | 0.0955 | 0.171 | 11.01 |
| XLIII | Human | 0.0034 | 0.382 | 0.583 | 0.839 | 62.92 |
| XLIV | Human | 0 | 0.0277 | 0.0597 | 0.106 | 6.70 |
| XLV | Human | 0 | 0 | 0 | 0 | 0.00 |
| XLVI | Human | 0 | 0 | 0 | 0 | 0.00 |
| XLVII | Human | 0 | 0 | 0 | 0 | 0.00 |
| XLVII | Human | 0 | 0.0418 | 0.0769 | 0.156 | 9.40 |
| XLIX | Human | 0 | 0.0159 | 0.0303 | 0.0592 | 3.62 |
| LII | Human | 0.0201 | 1.05 | 1.22 | 1.3 | 125.70 |
| LIII | Human | 0.0159 | 0.0165 | 0.0165 | 0.0171 | 1.99 |
| LIV | Human | 0 | 0.486 | 0.694 | 0.848 | 71.25 |
| LV | Human | 0.0045 | 0.545 | 0.741 | 0.954 | 78.38 |
| LXIV | Human | 0 | 0.0793 | 0.155 | 0.283 | 17.84 |
| LXVII | Human | 0 | 0.224 | 0.408 | 0.657 | 44.79 |
| LXX | Human | 0 | 0.0179 | 0.0411 | 0.0972 | 5.303 |
| LXXI | Human | 0 | 0 | 0.00262 | 0.00643 | 0.3108 |
| LXXII | Human | 0 | 0.02 | 0.0556 | 0.147 | 7.512 |
| LXXIII | Human | 0 | 0.00817 | 0.0216 | 0.0509 | 2.744 |

Example 2

Syntheses of Treprostinil Disubstituted Prodrugs LXX-LXXIII

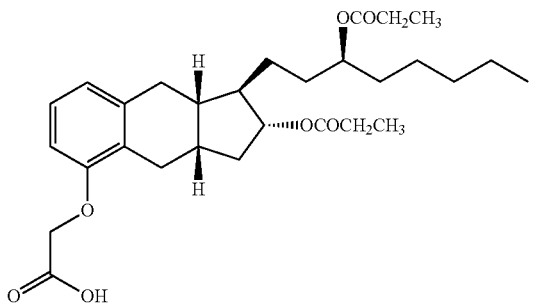

LXX

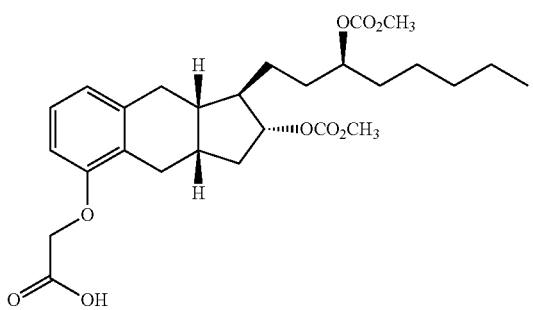

LXXI

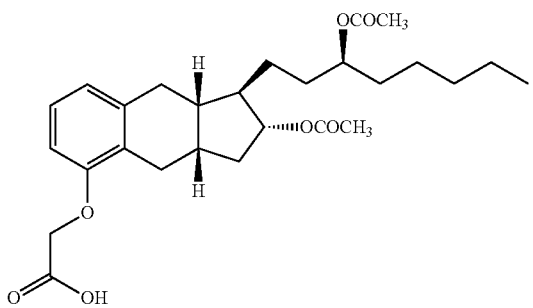

LXXII

75

-continued

LXXIII

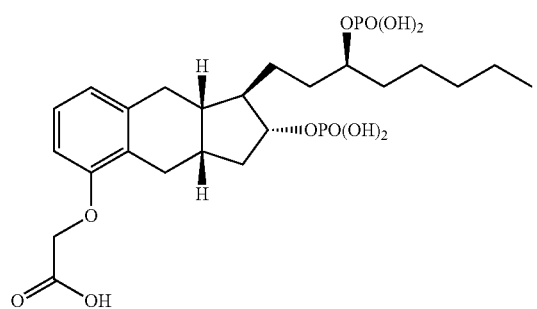

Scheme 1: Synthesis of Treprostinil Disubstituted Prodrugs LXX-LXXIII

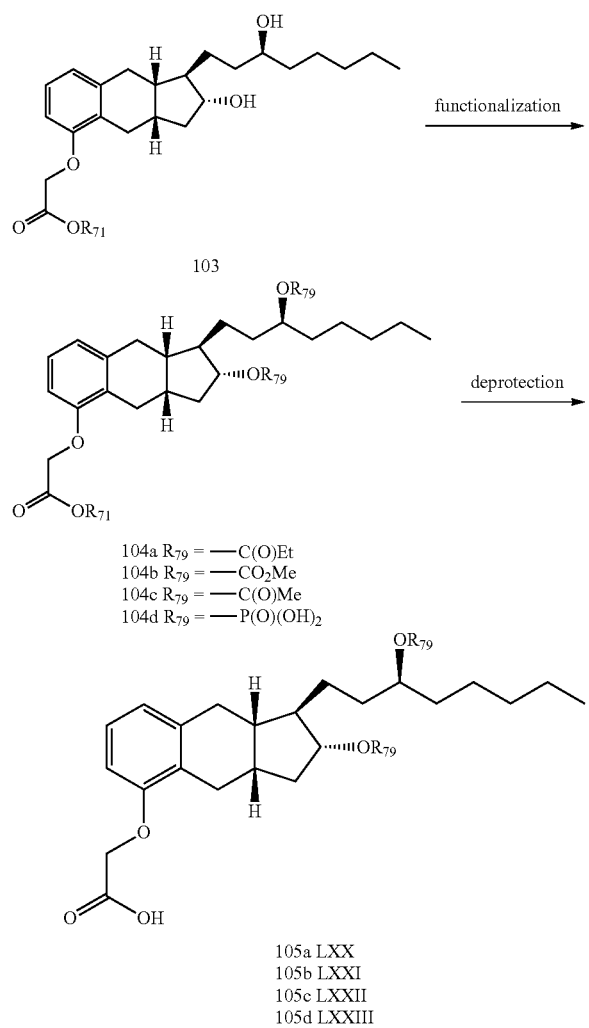

104a $R_{79}$ = —C(O)Et
104b $R_{79}$ = —CO$_2$Me
104c $R_{79}$ = —C(O)Me
104d $R_{79}$ = —P(O)(OH)$_2$

105a LXX
105b LXXI
105c LXXII
105d LXXIII

In Scheme 1, $R_{71}$ may be may be benzyl or a substituted benzyl, i.e. a benzyl group substituted at one or more meta, ortho or para positions with one or more substituents, which may be independently selected from the group consisting of —NO2, —CN, halogen (e.g., —F, —Cl, —Br or —I), ($C_1$-$C_3$)alkyl, halo($C_1$-$C_3$)alkyl, ($C_1$-$C_3$)alkoxy and halo($C_1$-$C_3$)alkoxy. The functionalization reaction may be, for example, acylation, carbonylation or phosphorylation.

76

EXPERIMENTAL

General Procedure for the Synthesis of Treprostinil Benzyl Ester Diacylate (104a and 104c)

Acylation

To a stirring solution of treprostinil benzyl ester (103) (1.0 eq.) and DMAP (4.0 eq) in dichloromethane (DCM) (20 v/wt) was added propionic anhydride (2.5 eq) (for 104a) or acetic anhydride (2.5 eq) (for 104c). The resulting mixture was stirred at room temperature for 1 h. The solvent was removed in vacuo to give crude product. It was purified on silica gel column chromatography to give treptostinil benzyl ester diacylate (104a or 104c). These compounds (104a, 104c) were characterized by $^1$H NMR and LCMS. The purities were determined by HPLC.

Procedure for the Synthesis of Treprostinil Benzyl Ester Dicarbonate (104b)

To a solution of treprostinil benzyl ester (103) (1.0 eq) in anhydrous pyridine (5 v/wt) at 0 to 5° C. under argon was added dropwise a solution of methyl chloroformate (6.0 eq) in anhydrous dichloromethane (5 v/wt) over a period of 5 min. After complete addition, the reaction mixture was stirred at 0° C. to room temperature for 2 h. The mixture was treated with water and then extracted with dichloromethane. The dichloromethane extracts were washed with water, brine, dried over Na$_2$SO$_4$, filtered, and concentrated in vacuo to give crude oil. The crude product was purified by silica gel column chromatography to give the pure treprostinil benzyl ester dicarbonate (104b) as white solid. The pure product was characterized by IR, $^1$H NMR, $^{13}$C NMR, DEPT-135 and LC-MS. The purity was determined by HPLC.

Procedure for the Synthesis of Treprostinil Benzyl Ester di(dibenzyl)phosphate (104d)

To a stirring solution of treprostinil benzyl ester (103) (1.0 eq) was added 1H-tetrazole (4.0 eq) (0.45 M in acetonitrile) through addition funnel under argon. The resulting mixture was stirred at room temperature for 10 min and dibenzyl-N,N-diisopropylphosphoramidite (3.0 eq) in DCM (7 v/wt) was added dropwise. The mixture was stirred at room temperature for 2 h. The reaction at this stage was complete and the system was cooled to −78° C. (dry ice-acetone). 3-Chloroperoxybenzoic acid (mCPBA) (70-75%) (4.2 eq) was added in one portion and stirred at that temperature for 2 h. The reaction was complete and sodium sulfite solution (10%) was added and stirred overnight (slowly warm up to room temperature). The DCM layer was checked by peroxide 100 test tip to make sure that there is no peroxide in solution (wash more time with sodium sulfite solution (10%) if peroxide exists). The DCM layer was washed with brine, dried over sodium sulfate, filtered, and concentrated in vacuo to give crude product. It was purified by silica gel column chromatography to give treprostinil benzyl ester di(dibenzyl)phosphate (104d). The compound 104d was characterized by $^1$H NMR and LCMS. The purity was determined by HPLC.

General Procedure for the Synthesis of Treprostinil Disubstituted Prodrugs (105a-d) (Deprotection or Debenzylation)

To a solution of treprostinil benzyl ester disubstituted prodrugs (104a-d) (1.0 eq) in ethyl acetate (20 v/wt) (and 1 v/wt water in case of 104d) was added 5% palladium on carbon (~50% water) (25 wt %) under argon. The mixture was evacuated under house vacuum and replaced by hydrogen (filled in a balloon) at room temperature and this process was repeated three times. The reaction mixture was stirred under the atmosphere of hydrogen at room temperature for 2.5 h. The mixture was filtered through Celite pad and washed with EtOAc. The filtrate was evaporated in vacuo to give pure treprostinil disubstituted prodrugs (105a-d) The pure products were characterized by IR, $^1$H NMR, $^{13}$C NMR, DEPT-135 ($^{31}$P NMR for 105d) and LC-MS. The purities were determined by HPLC.

Similarly following the general procedure described above, treprostinil disubstituted prodrugs LXX-LXXIII were synthesized. LXX, treprostinil dipropionate (105a); LXXI, treprostinil dicarbonate (105b), LXXII, treprostinil diacetate (105c), LXXIII, treprostinil diphosphate (105d).

Example 3

A Single Dose Subcutaneous Infusion Pharmacokinetic Study of Prodrugs LXX, LXXI, LXXII and LXXIII in Rats Objective(s)

The objectives of this study are to evaluate the pharmacokinetic profile of prodrugs LXX, LXXI, LXXII and LXXIII when administered by continuous subcutaneous infusion (24 hours) to Sprague Dawley rats.

Test Materials

| Test Article Identification | | | | |
|---|---|---|---|---|
| | Test Article | Test Article | Test Article | Test Article |
| Identification: | LXX | LXXI | LXXII | LXXIII |
| Storage Conditions: | Set to maintain a target temperature of 5° C., protected from light | Set to maintain a target temperature of 5° C., protected from light | Set to maintain a target temperature of 5° C., protected from light | Set to maintain a target temperature of 5° C., protected from light |

| Vehicle Identification | | |
|---|---|---|
| | Vehicle for LXX and LXXI | Vehicle for LXXII and LXXIII |
| Identification: | 15-mM phosphate buffer with 0.3% m-cresol and mannitol | 15-mM phosphate buffer with 0.3% m-cresol and sodium chloride |
| Storage Conditions: | Set to maintain a target temperature of 5° C. | Set to maintain a target temperature of 5° C. |

Dose Formulation and Analysis

Preparation of Formulations

Dose formulations divided into aliquots where required to allow them to be dispensed on each dosing occasion.

| Preparation Details | | |
|---|---|---|
| Dose Formulation | Frequency of Preparation | Storage Conditions |
| Vehicle | Prepared on day of dosing | Set to maintain 18° C. to 24° C. |
| Test Article | Prepared on day of dosing | Set to maintain 18° C. to 24° C. |

Test System

Species: Rat
Strain: Crl:CD(SD) Sprague Dawley rat
Condition: Purpose-bred, naïve, surgically catheterized (subcutaneous) with vascular access buttons
Number of Males: 108 (plus 10 alternates)
Target Age at the Initiation of Dosing:
Target Weight at the
7 to 8 weeks 200 to 320 g (males) Animal Identification
Method: A subcutaneously implanted electronic identification chip. Animals be received with microchips implanted.

Environmental Acclimation

Method: Each animal be inspected upon receipt.
Animals judged to be in good health be placed in acclimation for at least 7 days.

Surgical Preparation

Method: Animals be implanted with subcutaneous catheters with vascular access buttons prior to receipt (for subcutaneous dosing) and be maintained per CRL SOPs. In the event of a damaged port, an attempt may be made to surgically repair the port. The animals be anesthetized and surgically prepared per CRL SOPs.

Catheter Maintenance

Method: Shortly after receipt, the animals be connected to a tether infusion system. Catheter patency be maintained using 0.9% sodium chloride for injection (i.e., saline) at a rate of 0.03 mL/hr until the start of dosing. At least every other day, the infusion system be flushed with a bolus (approximately 0.5 mL) of saline.

Selection, Assignment, Replacement, and Disposition of Animals

Selection: Animals be assigned to groups by a stratified randomization scheme designed to achieve similar group mean body weights. Animals in poor health or at extremes of body weight range not be assigned to groups. Individual body weights at randomization within ±20% of the mean.

Replacement: Before the initiation of dosing, any assigned animals considered unsuitable for use in the study be replaced by alternate animals obtained from the same shipment and maintained under the same environmental conditions. After initiation of dosing, study animals may be replaced during the replacement period with alternate animals in the event of accidental injury, non-test article-related health issues, or similar circumstances.

| EXPERIMENTAL DESIGN | | | | | | |
|---|---|---|---|---|---|---|
| Group No. | Test Material | Dose Level (mg/kg) | Dose Volume$^a$ (mL/kg) | Dose Concentration (mg/mL) | Dose Rate (mL/kg/hr) | No. of Male Animals |
| 1 | LXX | 1 | 12 | 0.083 | 0.5 | 9 |
| 2 | LXX | 3 | 12 | 0.25 | 0.5 | 9 |
| 3 | LXX | 10 | 12 | 0.83 | 0.5 | 9 |
| 4 | LXXI | 1 | 12 | 0.083 | 0.5 | 9 |
| 5 | LXXI | 3 | 12 | 0.25 | 0.5 | 9 |
| 6 | LXXI | 10 | 12 | 0.83 | 0.5 | 9 |
| 7 | LXXII | 1 | 12 | 0.083 | 0.5 | 9 |
| 8 | LXXII | 3 | 12 | 0.25 | 0.5 | 9 |
| 9 | LXXII | 10 | 12 | 0.83 | 0.5 | 9 |
| 10 | LXXIII | 1 | 12 | 0.083 | 0.5 | 9 |
| 11 | LXXIII | 3 | 12 | 0.25 | 0.5 | 9 |
| 12 | LXXIII | 10 | 12 | 0.83 | 0.5 | 9 |

Administration of Test and Control Articles

Dose Route: Continuous Subcutaneous infusion (VAB) into the dorsolumbar region. Frequency: Single 24-hour infusion Method: The day of dosing be designated as Day 1. Dose formulations be administered via subcutaneous infusion using programmed SAI infusion pumps with a tethered infusion system connected to the VABs. Infusion system be pre-filled with test article so that infusion begins at activation of the SAI infusion pump. The test article dose be administered over a 24-hour infusion period. Following the 24-hour infusion period, the tether systems be removed and a 0.5 ml bolus of saline be administered to the VAB.

Prior to dose administration, saline (0.5 ml) be administered in an effort to check catheter patency. Individual doses be withdrawn into appropriate syringes labeled with the animal number, study number, and date. The dosing syringes be filled with an appropriate volume of test article.

The infusion pumps be set for the appropriate infusion rate to deliver the proper dose volume over the required infusion duration. For dosing accountability purposes, the weight of the syringe containing the dose formulation be recorded prior to the start and at the end of infusion. Any dose accountability and/or total duration deviation greater than f 15% of target be documented.

Figure 6:
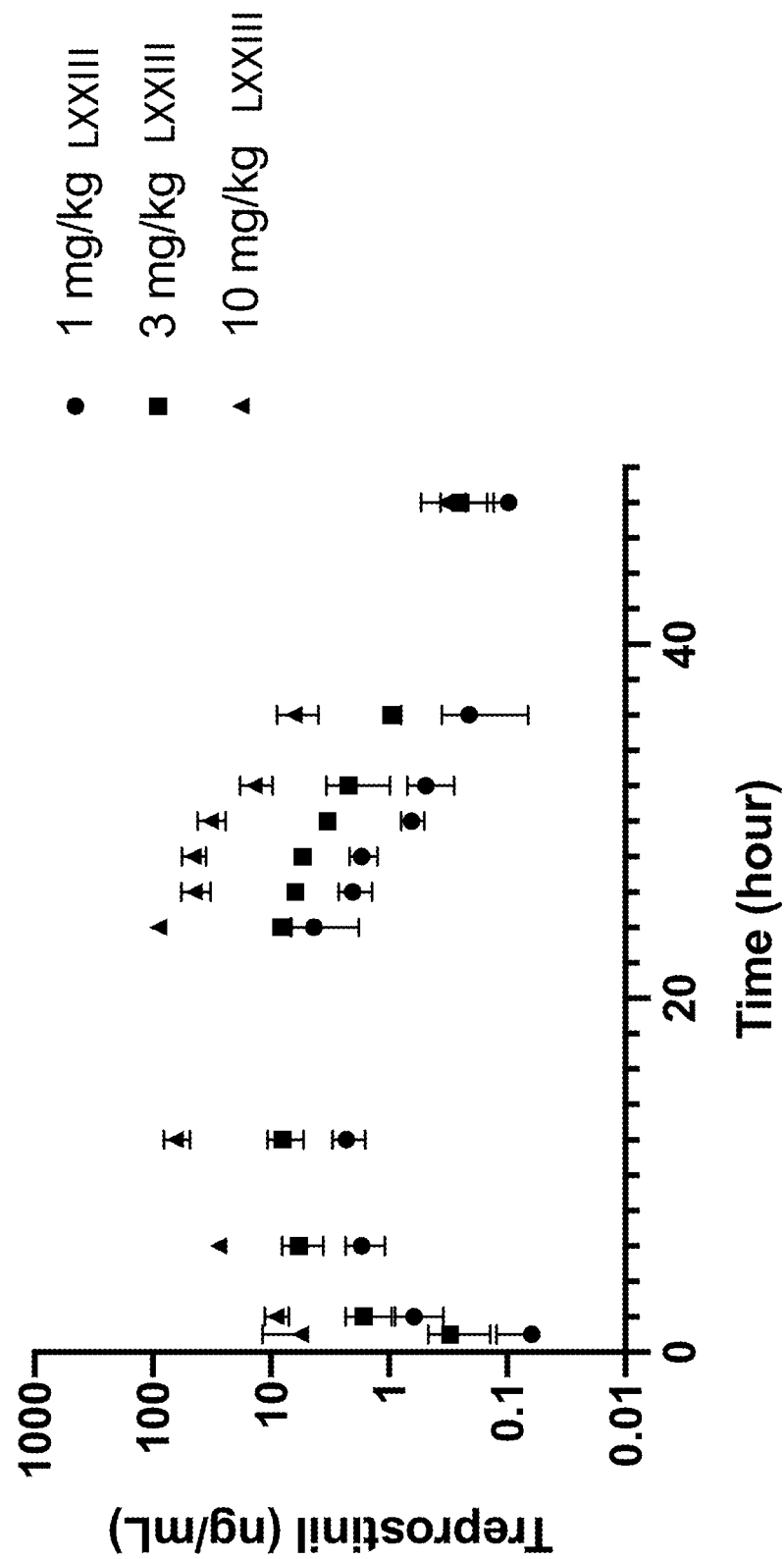
FIG. 6 presents a plot illustrating plasma concentrations of treprostinil in rats administered that were infused a solution containing prodrug LXXIII through an in-dwelling subcutaneous catheter at doses of 1, 3 and 10 mg/kg of prodrug LXXIII. Each dose was infused at a constant infusion rate and samples were collected at predetermined times.

Results of the study for prodrug LLXXIII are reported in FIG. 6.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of treating pulmonary hypertension comprising administering subcutaneously to a subject in need thereof an effective amount of a treprostinil prodrug, wherein said prodrug has a formula:

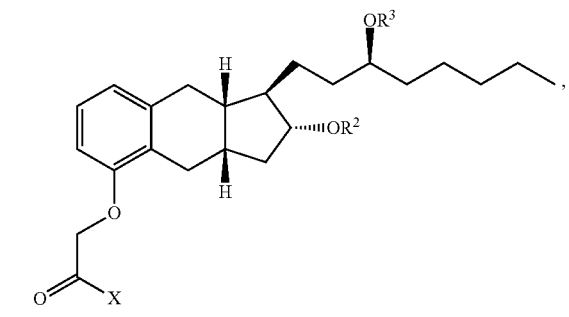

wherein X is OH; each of $R^2$ and $R^3$ is a phosphorus containing group and said administering results in no or less pain at a site of the subcutaneous injection compared to subcutaneously administered treprostinil.

2. The method of claim 1, wherein said prodrug has a liver half-time of 15 minutes or less.

3. The method of claim 1, wherein said prodrug has a half-time in a gastric and/or intestinal fluid of greater than 120 minutes.

4. The method of claim 1, wherein said prodrug has a liver half-time of 15 minutes or less and a half-time in a gastric and/or intestinal fluid of greater than 120 minutes.

5. The method of claim 1, wherein said prodrug is subcutaneously administered as a solution, wherein said solution has a pH ranging from 5 to 9 and said solution after being stored for at least 1 week at a temperature from 30 C to 45 C has a treprostinil per se concentration of less than 0.5%.

6. The method of claim 1, wherein said administering is continuous subcutaneous administering.

7. The method of claim 1, wherein the subject is a human.

8. The method of claim 1, wherein $R^2$ and $R^3$ are the same phosphorus containing group.

9. The method of claim 1, wherein the prodrug has the formula:
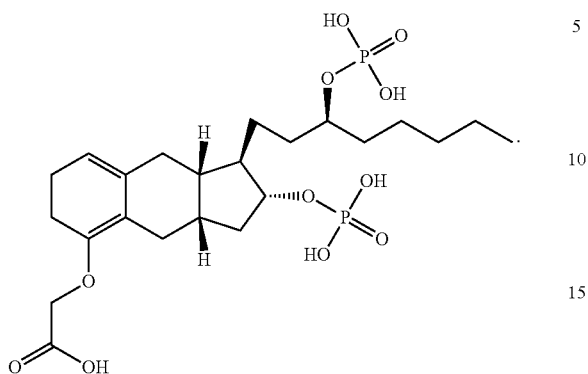
10. The method of claim 1, wherein the prodrug remains stable in plasma of the subject for at least 120 minutes.
* * * * *